(12) United States Patent
Globerman et al.

(10) Patent No.: US 9,370,388 B2
(45) Date of Patent: Jun. 21, 2016

(54) COMPOSITE MATERIAL BONE IMPLANT

(75) Inventors: Oren Globerman, Kfar-Shemaryahu (IL); Mordechay Beyar, Caesarea (IL); Elad Einav, Zikhron-Yaakov (IL); Hila Wachsler-Avrahami, Tel-Aviv (IL)

(73) Assignee: Carbofix Orthopedics Ltd., Herzlia Pituach (IL)

( * ) Notice: Subject to any disclaimer, the term of this patent is extended or adjusted under 35 U.S.C. 154(b) by 116 days.

(21) Appl. No.: 13/702,334

(22) PCT Filed: Jun. 7, 2011

(86) PCT No.: PCT/IB2011/052468
§ 371 (c)(1),
(2), (4) Date: Dec. 6, 2012

(87) PCT Pub. No.: WO2011/154891
PCT Pub. Date: Dec. 15, 2011

(65) Prior Publication Data
US 2013/0079829 A1    Mar. 28, 2013

Related U.S. Application Data

(60) Provisional application No. 61/344,182, filed on Jun. 7, 2010, provisional application No. 61/443,308, filed on Feb. 16, 2011, provisional application No. 61/486,280, filed on May 15, 2011.

(51) Int. Cl.
*A61B 17/80* (2006.01)
*A61B 17/86* (2006.01)
(Continued)

(52) U.S. Cl.
CPC ......... *A61B 17/8625* (2013.01); *A61B 17/1728* (2013.01); *A61B 17/7233* (2013.01);
(Continued)

(58) Field of Classification Search
CPC ............... A61B 17/80; A61B 17/1728; A61B 17/8052; A61B 17/8686; A61B 17/866
USPC ........................ 606/70, 71, 280–331, 96–98
See application file for complete search history.

(56) References Cited

U.S. PATENT DOCUMENTS 3,630,253 A    12/1971  Sherman
4,058,581 A    11/1977  Park
(Continued)

FOREIGN PATENT DOCUMENTS

CN    1170380    1/1998
CN    1324278    11/2001
(Continued)

OTHER PUBLICATIONS

Notification of Office Action Dated Mar. 7, 2014 From the State Intellectual Property Office of the People's Republic of China Re. Application No. 201080012276.1 and Its Translation Into English.
(Continued)

*Primary Examiner* — Christopher Beccia

(57) ABSTRACT

Radiolucent composite implants. Some embodiments include reconfiguration indicators. Some embodiments include radio-opaque markers, especially along contours. Some embodiments are provided in kit form with accessories such as radiolucent drill guides and/or drives. Some embodiments have fiber reinforcement adapted for various usage scenarios. Some embodiments include metal components, for example, to increase strength. Also described are manufacturing methods.

26 Claims, 33 Drawing Sheets

(51) Int. Cl.
- *A61B 17/72* (2006.01)
- *A61B 17/88* (2006.01)
- *A61B 17/17* (2006.01)
- *A61B 19/00* (2006.01)

(52) U.S. Cl.
CPC ............ *A61B17/80* (2013.01); *A61B 17/8052* (2013.01); *A61B 17/866* (2013.01); *A61B 17/8685* (2013.01); *A61B 17/88* (2013.01); *A61B 17/8863* (2013.01); *A61B 17/1717* (2013.01); *A61B 17/862* (2013.01); *A61B 17/863* (2013.01); *A61B 2019/5466* (2013.01)

(56) References Cited

U.S. PATENT DOCUMENTS

| | | |
|---|---|---|
| 4,220,187 A | 9/1980 | Holmes |
| 4,667,664 A | 5/1987 | Taylor et al. |
| 4,706,659 A | 11/1987 | Matthews et al. |
| 4,718,801 A | 1/1988 | Berecz |
| 4,750,905 A | 6/1988 | Koeneman et al. |
| 4,824,314 A | 4/1989 | Stencel |
| 4,863,330 A | 9/1989 | Olez et al. |
| 4,875,474 A | 10/1989 | Border |
| 4,978,360 A | 12/1990 | Devanathan |
| 4,988,350 A | 1/1991 | Herzberg |
| 5,009,664 A | 4/1991 | Sievers |
| 5,032,125 A | 7/1991 | Durham et al. |
| 5,041,113 A | 8/1991 | Biedermann et al. |
| 5,060,635 A | 10/1991 | Steur et al. |
| 5,064,439 A | 11/1991 | Chang et al. |
| 5,181,930 A | 1/1993 | Dumbleton et al. |
| 5,192,330 A | 3/1993 | Chang et al. |
| 5,197,966 A | 3/1993 | Sommerkamp |
| 5,292,215 A | 3/1994 | Roberts, III |
| 5,397,358 A | 3/1995 | Wenner et al. |
| 5,522,817 A | 6/1996 | Sander et al. |
| 5,824,079 A | 10/1998 | Siegler et al. |
| 5,879,352 A | 3/1999 | Filoso et al. |
| 5,961,524 A | 10/1999 | Crombie |
| 6,030,389 A | 2/2000 | Wagner et al. |
| 6,206,881 B1 | 3/2001 | Frigg et al. |
| 6,342,055 B1 * | 1/2002 | Eisermann et al. ........ 623/17.16 |
| 6,471,707 B1 | 10/2002 | Miller et al. |
| 6,605,090 B1 | 8/2003 | Trieu et al. |
| 6,692,497 B1 * | 2/2004 | Tormala et al. ............... 606/281 |
| 6,692,498 B1 | 2/2004 | Niiranen et al. |
| 6,730,091 B1 | 5/2004 | Pfefferle et al. |
| 6,916,321 B2 | 7/2005 | TenHuisen et al. |
| 6,921,402 B2 | 7/2005 | Contiliano et al. |
| 7,419,714 B1 | 9/2008 | Magerl et al. |
| 7,785,325 B1 | 8/2010 | Milbank |
| 7,896,599 B2 | 3/2011 | Stephen et al. |
| 7,914,244 B2 | 3/2011 | Bubulka et al. |
| 8,128,627 B2 | 3/2012 | Justin et al. |
| 8,323,321 B2 | 12/2012 | Gradl |
| 8,709,055 B2 | 4/2014 | Beyar et al. |
| 2002/0029043 A1 | 3/2002 | Ahrens et al. |
| 2002/0133172 A1 | 9/2002 | Lambrecht et al. |
| 2002/0156473 A1 | 10/2002 | Bramlet et al. |
| 2003/0057590 A1 | 3/2003 | Loher et al. |
| 2004/0073218 A1 | 4/2004 | Dahners |
| 2004/0260291 A1 | 12/2004 | Jensen |
| 2005/0096656 A1 * | 5/2005 | Behrens ........................ 606/64 |
| 2005/0131413 A1 | 6/2005 | O'Driscoll et al. |
| 2005/0177153 A1 | 8/2005 | Guzman et al. |
| 2005/0192578 A1 | 9/2005 | Horst |
| 2005/0234457 A1 | 10/2005 | James et al. |
| 2006/0004431 A1 | 1/2006 | Fuller et al. |
| 2006/0009771 A1 | 1/2006 | Orbay et al. |
| 2006/0015110 A1 | 1/2006 | Pepper |
| 2006/0041261 A1 | 2/2006 | Osypka |
| 2006/0079900 A1 | 4/2006 | Mathieu et al. |
| 2006/0116678 A1 | 6/2006 | Impellizzeri |
| 2006/0189996 A1 * | 8/2006 | Orbay et al. ................ 606/87 |
| 2006/0195085 A1 | 8/2006 | Happonen et al. |
| 2006/0200142 A1 | 9/2006 | Sohngen et al. |
| 2006/0235400 A1 | 10/2006 | Schneider |
| 2006/0259039 A1 | 11/2006 | Pitkanen et al. |
| 2006/0264948 A1 | 11/2006 | Williams |
| 2006/0282168 A1 | 12/2006 | Sherman et al. |
| 2007/0083207 A1 | 4/2007 | Ziolo et al. |
| 2007/0110544 A1 | 5/2007 | Friederich et al. |
| 2007/0123878 A1 | 5/2007 | Shaver |
| 2007/0162018 A1 * | 7/2007 | Jensen et al. .................. 606/69 |
| 2007/0167953 A1 * | 7/2007 | Prien et al. .................. 606/102 |
| 2007/0173843 A1 * | 7/2007 | Matityahu .................... 606/69 |
| 2007/0233105 A1 | 10/2007 | Nelson et al. |
| 2007/0260244 A1 | 11/2007 | Wolter |
| 2008/0046091 A1 | 2/2008 | Weiss et al. |
| 2008/0140130 A1 | 6/2008 | Chan et al. |
| 2008/0195157 A1 | 8/2008 | Orschler et al. |
| 2008/0208259 A1 | 8/2008 | Gilbert et al. |
| 2008/0234752 A1 | 9/2008 | Dahners |
| 2008/0234762 A1 | 9/2008 | Forstein et al. |
| 2008/0287951 A1 | 11/2008 | Stoneburner et al. |
| 2008/0294201 A1 * | 11/2008 | Huddleston, III ............ 606/280 |
| 2009/0018588 A1 | 1/2009 | Eckhof et al. |
| 2009/0088807 A1 | 4/2009 | Castaneda et al. |
| 2009/0228008 A1 | 9/2009 | Justin et al. |
| 2009/0228048 A1 | 9/2009 | Duncan et al. |
| 2009/0248089 A1 | 10/2009 | Jacofsky et al. |
| 2009/0312803 A1 | 12/2009 | Austin et al. |
| 2010/0016858 A1 | 1/2010 | Michel |
| 2010/0042215 A1 | 2/2010 | Stalcup et al. |
| 2010/0094423 A1 | 4/2010 | Foley et al. |
| 2010/0100134 A1 | 4/2010 | Mocanu |
| 2010/0190138 A1 | 7/2010 | Giorno |
| 2010/0217333 A1 | 8/2010 | McShane et al. |
| 2010/0234847 A1 | 9/2010 | Impellizzeri |
| 2010/0312286 A1 | 12/2010 | Dell'Oca |
| 2011/0015682 A1 | 1/2011 | Lewis et al. |
| 2011/0106086 A1 * | 5/2011 | Laird ............................ 606/70 |
| 2011/0218570 A1 * | 9/2011 | Felix et al. ................... 606/246 |
| 2011/0224737 A1 | 9/2011 | Lewis et al. |
| 2011/0282395 A1 | 11/2011 | Beyar et al. |
| 2011/0288598 A1 | 11/2011 | Moed et al. |
| 2012/0059376 A1 | 3/2012 | Rains et al. |
| 2012/0065638 A1 | 3/2012 | Moore |
| 2012/0083847 A1 | 4/2012 | Huebner et al. |
| 2012/0136396 A1 | 5/2012 | Baker et al. |
| 2012/0203285 A1 | 8/2012 | Rotini et al. |
| 2012/0283790 A1 | 11/2012 | Meyer, III |
| 2012/0330361 A1 | 12/2012 | Gepstein |
| 2013/0116693 A1 | 5/2013 | Nelson et al. |
| 2013/0184765 A1 | 7/2013 | Beyar et al. |
| 2013/0218214 A1 | 8/2013 | Beyar et al. |
| 2013/0237813 A1 | 9/2013 | Beyar et al. |
| 2013/0261675 A1 | 10/2013 | Fritzinger |
| 2013/0296863 A1 | 11/2013 | Globerman et al. |
| 2013/0296952 A1 | 11/2013 | Globerman et al. |
| 2013/0325007 A1 | 12/2013 | Beyar et al. |
| 2014/0222001 A1 | 8/2014 | Beyar et al. |
| 2015/0327893 A1 | 11/2015 | Beyar et al. |
| 2016/0067046 A1 | 3/2016 | Globerman et al. |
| 2016/0113695 | 4/2016 | Globerman et al. |

FOREIGN PATENT DOCUMENTS

| | | |
|---|---|---|
| CN | 1367669 | 9/2002 |
| CN | 1482890 | 3/2004 |
| CN | 1586416 | 3/2005 |
| CN | 2746884 | 12/2005 |
| CN | 1819799 | 8/2006 |
| CN | 101304695 | 11/2008 |
| DE | 4343117 | 6/1995 |
| EP | 1042989 | 10/2000 |
| EP | 1598028 | 11/2005 |
| EP | 1733704 | 12/2006 |
| EP | 1779796 | 5/2007 |
| EP | 1857066 | 11/2007 |
| EP | 2198792 | 6/2010 |
| EP | 2292176 | 3/2011 |
| FR | 2555902 | 6/1985 |

(56) References Cited

FOREIGN PATENT DOCUMENTS

| | | |
|---|---|---|
| FR | 2646767 | 11/1990 |
| FR | 2829378 | 3/2003 |
| GB | 2442706 | 4/2008 |
| JP | 02-198550 | 8/1990 |
| JP | 05-000137 | 1/1993 |
| JP | 05-092019 | 4/1993 |
| JP | 06-500945 | 2/1994 |
| JP | 2002-536048 | 10/2002 |
| JP | 2007-125387 | 5/2007 |
| JP | 2008-036094 | 2/2008 |
| SR | 1111748 | 9/1984 |
| WO | WO 92/18068 | 10/1992 |
| WO | WO 93/13713 | 7/1993 |
| WO | WO 94/07425 | 4/1994 |
| WO | WO 96/02203 | 2/1996 |
| WO | WO 96/09014 | 3/1996 |
| WO | WO 96/19336 | 6/1996 |
| WO | WO 01/15617 | 3/2001 |
| WO | WO 2006/090226 | 8/2006 |
| WO | WO 2007/009123 | 1/2007 |
| WO | WO 2007/010671 | 1/2007 |
| WO | WO 2007/035772 | 3/2007 |
| WO | WO 2008/033742 | 3/2008 |
| WO | WO 2008/064346 | 5/2008 |
| WO | WO 2008/092192 | 8/2008 |
| WO | WO 2009/002890 | 12/2008 |
| WO | WO 2009/143374 | 11/2009 |
| WO | WO 2009/152270 | 12/2009 |
| WO | WO 2009/152272 | 12/2009 |
| WO | WO 2010/045473 | 4/2010 |
| WO | WO 2010/082183 | 7/2010 |
| WO | WO 2011/042407 | 4/2011 |
| WO | WO 2011/154891 | 12/2011 |
| WO | WO 2012/107913 | 8/2012 |

OTHER PUBLICATIONS

Corrected Notice of Allowability Dated Feb. 14, 2014 From the US Patent and Trademark Office Re. U.S. Appl. No. 13/144,938.
Notification of Office Action Dated Oct. 18, 2013 From the State Intellectual Property Office of the People's Republic of China Re. Application No. 201080012276.1 and Its Translation Into English.
Translation of Search Report Dated Oct. 18, 2013 From the State Intellectual Property Office of the People's Republic of China Re. Application No. 201080012276.1.
Official Action Dated Jun. 27, 2013 From the US Patent and Trademark Office Re. U.S. Appl. No. 13/144,938.
Translation of Notification of Office Action Dated Apr. 12, 2013 From the State Intellectual Property Office of the People's Republic of China Re. Application No. 201080012276.1.
Translation of Search Report Dated Apr. 12, 2013 From the State Intellectual Property Office of the People's Republic of China Re. Application No. 201080012276.1.
European Search Report and the Written Opinion Dated Apr. 18, 2013 From the European Patent Office Re. Application No. 13151490.3.
Communication Relating to the Results of the Partial International Search Dated May 17, 2010 From the International Searching Authority Re.: Application No. PCT/IB2010/050225.
Communication Relating to the Results of the Partial International Search Dated May 29, 2012 From the International Searching Authority Re. Application No. PCT/IB2012/050645.
Communication Relating to the Results of the Partial International Search Dated Sep. 29, 2011 From the International Searching Authority Re. Application No. PCT/IB2011/052468.
International Preliminary Report on Patentability Dated Jul. 28, 2011 From the International Bureau of WIPO Re. Application No. PCT/IB2010/050225.
International Search Report and the Written Opinion Dated Nov. 10, 2010 From the International Searching Authority Re: Application No. PCT/IB2010/050225.
International Search Report and the Written Opinion Dated Aug. 24, 2012 From the International Searching Authority Re: Application No. PCT/IB2010/050225.
International Search Report and the Written Opinion Dated Dec. 29, 2011 From the International Searching Authority Re: Application No. PCT/IB2011/052468.
Communication Pursuant to Rules 70(2) and 70a(2) EPC and Reference to Rule 39(1) EPC Dated Jul. 22, 2013 From the European Patent Office Re. Application No. 13151490.3.
Communication Pursuant to Article 94(3) EPC Dated Jul. 2, 2013 From the European Patent Office Re. Application No. 10702750.0.
Restriction Official Action Dated Mar. 22, 2013 From the US Patent and Trademark Office Re. U.S. Appl. No. 13/144,938.
Communication Pursuant to Article 94(30 EPC Dated Jul. 11, 2014 From the European Patent Office Re. Application No. 13151490.3.
Restriction Official Action Dated Aug. 1, 2014 From the US Patent and Tradmark Office Re. U.S. Appl. No. 13/742,462.
International Preliminary Report on Patentability Dated Dec. 20, 2012 From the International Bureau of WIPO Re. Application No. PCT/IB2011/052468.
Office Action Dated Aug. 10, 2014 From the Israel Patent Office Re. Application No. 214105 and Its Translation Into English.
Official Action Dated Aug. 5, 2014 From the US Patent and Trademark Office Re. U.S. Appl. No. 13/935,497.
Applicant-Initiated Interview Summary Dated Oct. 17, 2013 From the US Patent and Trademark Office Re. U.S. Appl. No. 13/144,938.
Restriction Official Action Dated May 30, 2014 From the US Patent and Trademark Office Re. U.S. Appl. No. 14/246,161.
Notice of Reason for Rejection Dated Jun. 3, 2014 From the Japanese Patent Office Re. Application No. 2011-545832 and Its Translation Into English.
Office Action Dated Apr. 2, 2014 From the Israel Patent Office Re. Application No. 214105 and Its Translation Into English.
Corrected Notice of Allowability Dated Feb. 11, 2014 From the US Patent and Trademark Office Re. U.S. Appl. No. 13/144,938.
Official Action Dated Jan. 27, 2014 From the US Patent and Trademark Office Re. U.S. Appl. No. 13/935,501.
Notice of Allowance Dated Dec. 11, 2013 From the US Patent and Trademark Office Re. U.S. Appl. No. 13/144,938.
Official Action Dated Jul. 11, 2014 From the US Patent and Trademark Office Re. U.S. Appl. No. 13/935,501.
Official Action Dated Jul. 17, 2014 From the US Patent and Trademark Office Re. U.S. Appl. No. 14/246,161.
Notice of Reason for Rejection Dated Nov. 15, 2013 From the Japanese Patent Office Re. Application No. 2011-545832 and Its Translation Into English.
International Preliminary Report on Patentability Dated Aug. 22, 2013 From the International Bureau of WIPO Re. Application No. PCT/IB2012/050645.
Official Action Dated Dec. 19, 2014 From the US Patent and Trademark Office Re. U.S. Appl. No. 13/935,497.
Official Action Dated Dec. 19, 2014 From the US Patent and Trademark Office Re. U.S. Appl. No. 13/742,462. (Part I).
Official Action Dated Dec. 19, 2014 From the US Patent and Trademark Office Re. U.S. Appl. No. 13/742,462. (Part II).
Official Action Dated Dec. 23, 2014 From the US Patent and Trademark Office Re. U.S. Appl. No. 13/935,501.
Office Action Dated Jan. 22, 2015 From the Israel Patent Office Re. Application No. 223485.
Official Action Dated Jan. 22, 2015 From the US Patent and Trademark Office Re. U.S. Appl. No. 14/246,161.
Translation Dated Feb. 9, 2015 of Office Action Dated Jan. 22, 2015 From the Israel Patent Office Re. Application No. 223485.
Communication Pursuant to Article 94(3) EPC Dated Nov. 19, 2014 From the European Patent Office Re. Application No. 10702750.0.
Notification of Office Action Dated Oct. 29, 2014 From the State Intellectual Property Office of the People's Republic of China Re. Application No. 201180038951.2 and Its Translation Into English.
Search Report Dated Oct. 29, 2014 From the State Intellectual Property Office of the People's Republic of China Re. Application No. 201180038951.2 and Its Translation Into English.
Applicant-Initiated Interview Summary Dated Oct. 8, 2014 From the US Patent and Trademark Office Re. U.S. Appl. No. 13/935,501.

(56) References Cited

OTHER PUBLICATIONS

Applicant-Initiated Interview Summary Dated Nov. 21, 2014 From the US Patent and Trademark Office Re. U.S. Appl. No. 13/935,497.
Communication Pursuant to Article 94(3) EPC Dated Apr. 29, 2015 From the European Patent Office Re. Application No. 13151490.3.
Official Action Dated Apr. 1, 2015 From the US Patent and Trademark Office Re. U.S. Appl. No. 13/935,501.
Official Action Dated Apr. 29, 2015 From the US Patent and Trademark Office Re. U.S. Appl. No. 13/985,048.
Official Decision of Rejection Dated Mar. 3, 2015 From the Japanese Patent Office Re. Application No. 2011-545832 and Its Translation Into English.
Requisition by the Examiner and Examination Search Report Dated Mar. 17, 2015 From the Canadian Intellectual Property Office Re. Application No. 2,749,684.
Official Action Dated Jun. 12, 2015 From the US Patent and Trademark Office Re. U.S. Appl. No. 13/742,462.
Restriction Official Action Dated Jun. 25, 2015 From the US Patent and Trademark Office Re. U.S. Appl. No. 13/852,100.
Official Action Dated Sep. 28, 2015 From the US Patent and Trademark Office Re. U.S. Appl. No. 13/852,100.
Applicant-Initiated Interview Summary Dated Oct. 19, 2015 From the US Patent and Trademark Office Re. U.S. Appl. No. 13/742,462.
Notification of Office Action and Search Report Dated Dec. 2, 2015 From the State Intellectual Property Office of the People's Republic of China Re. Application No. 201410413164.7.
Translation Dated Dec. 20, 2015 of Notification of Office Action and Search Report Dated Dec. 2, 2015 From the State Intellectual Property Office of the People's Republic of China Re. Application No. 201410413164.7.
Notification of Office Action Dated Dec. 28, 2015 From the State Intellectual Property Office of the People's Republic of China Re. Application No. 201410413073.3.
Applicant-Initiated Interview Summary Dated Jan. 12, 2016 From the US Patent and Trademark Office Re. U.S. Appl. No. 13/852,100.
Notification of Office Action and Search Report Dated Jan. 13, 2016 From the State Intellectual Property Office of the People's Republic of China Re. U.S. Appl. No. 201410412613.6.
Translation Dated Jan. 17, 2016 of Notification of Office Action Dated Dec. 28, 2015 From the State Intellectual Property Office of the People's Republic of China Re. Application No. 201410413073.3.
Translation Dated Jan. 27, 2016 of Notification of Office Action Dated Jan. 13, 2016 From the State Intellectual Property Office of the People's Republic of China Re. Application No. 201410412613.6.
Advisory Action Before the Filing of an Appeal Brief Dated May 9, 2016 From the US Patent and Trademark Office Re. U.S. Appl. No. 13/985,048.

* cited by examiner

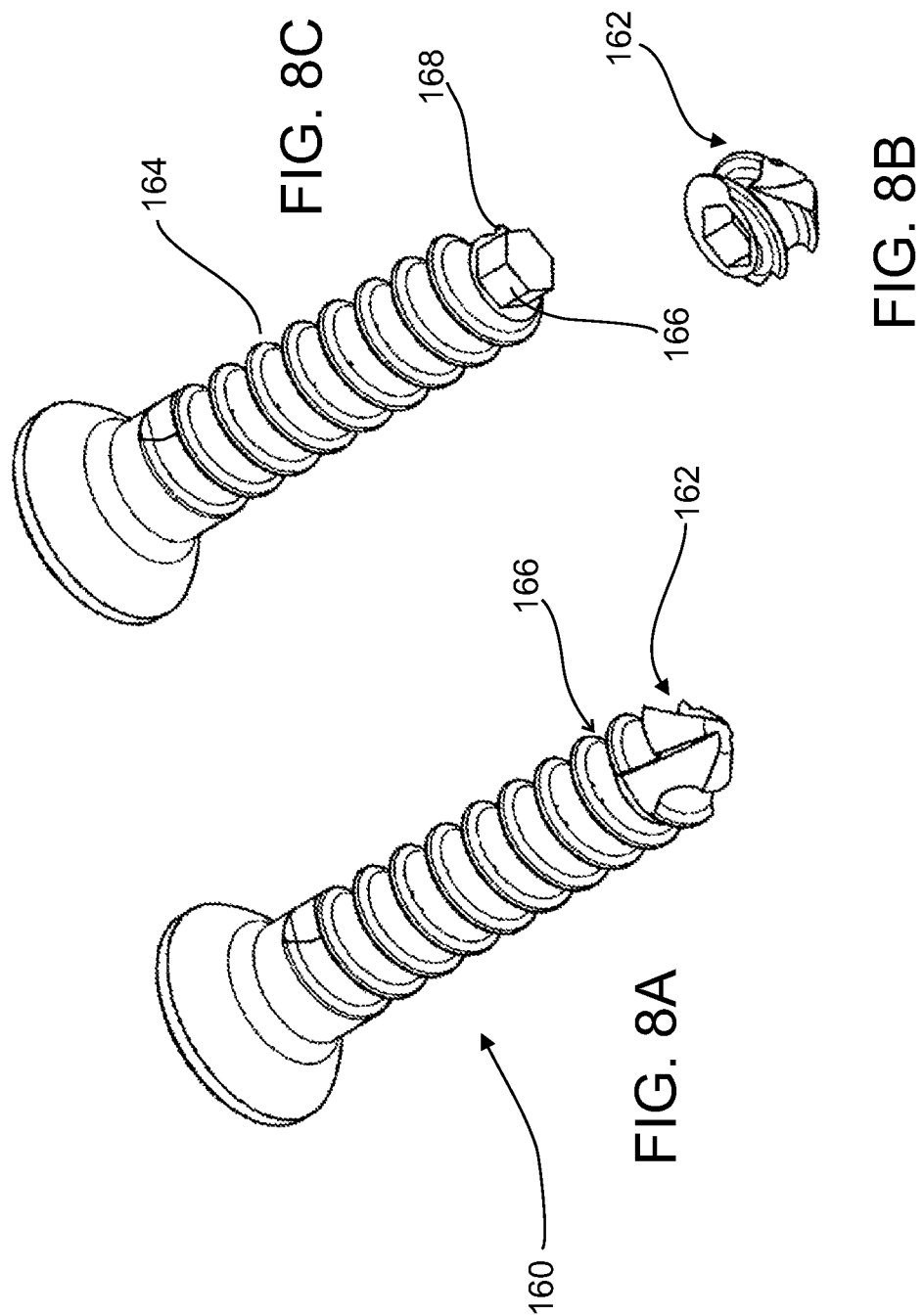

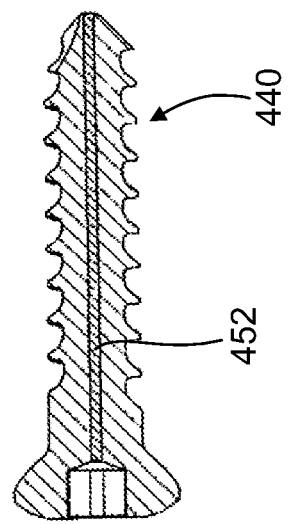
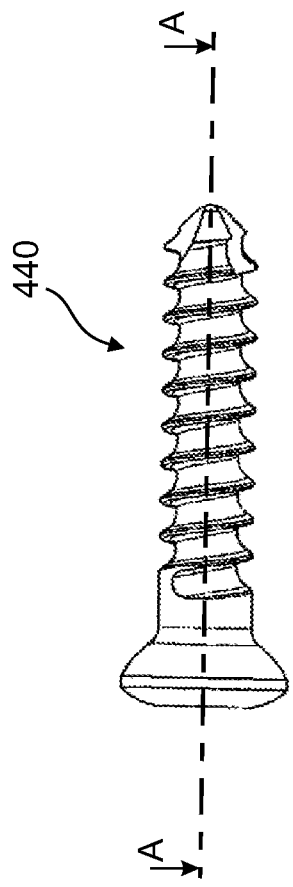
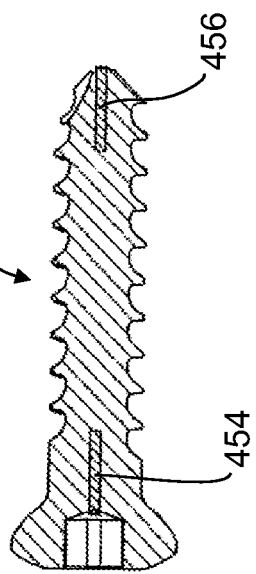
FIG. 16B
FIG. 16A
FIG. 16C

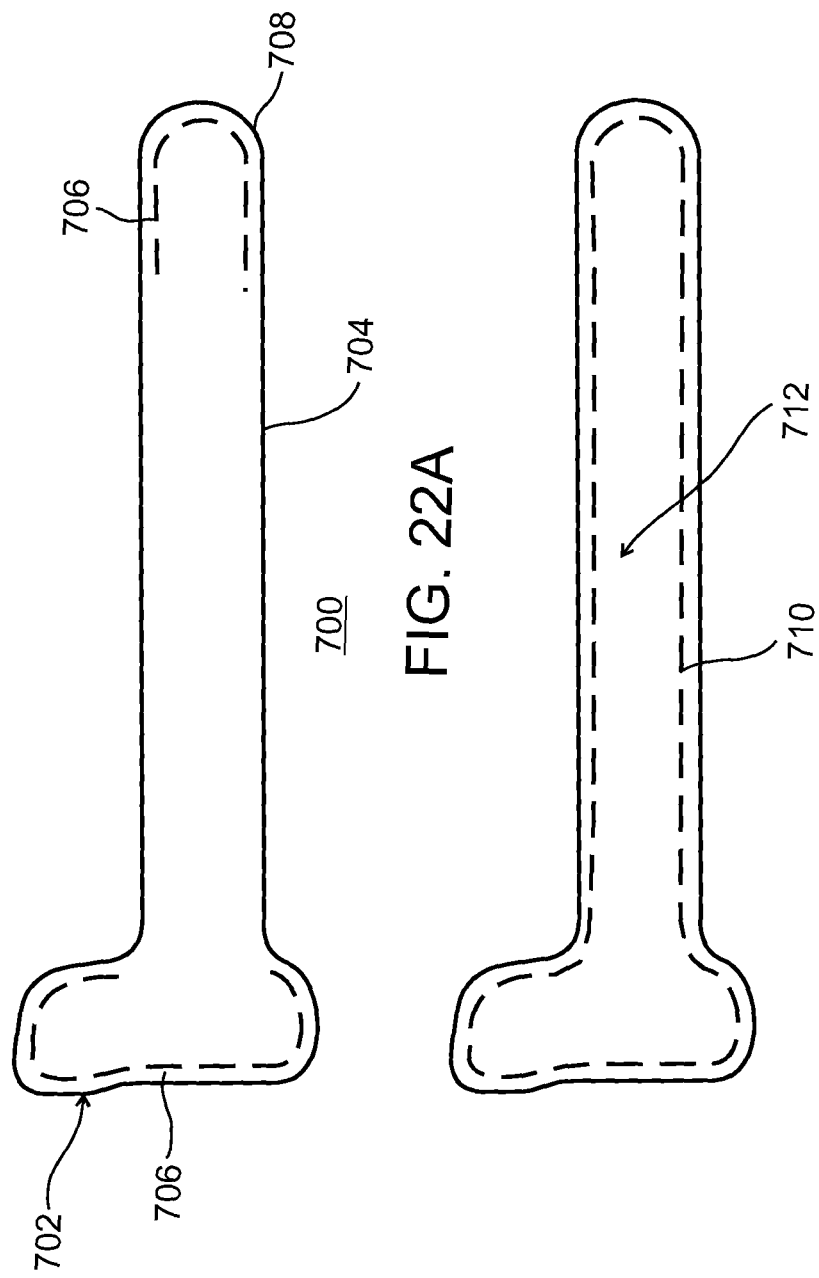

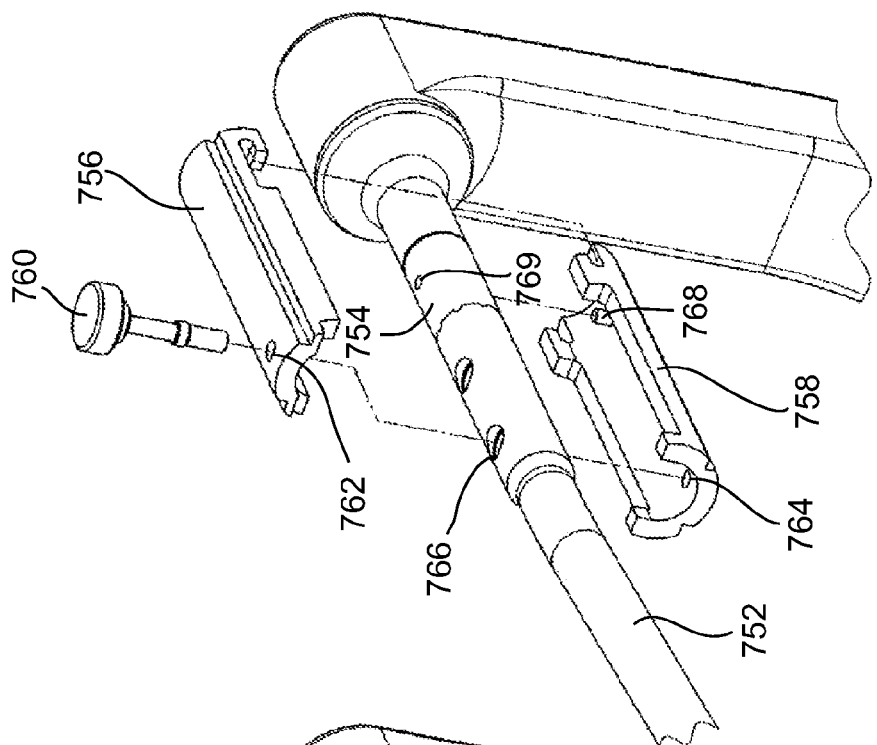
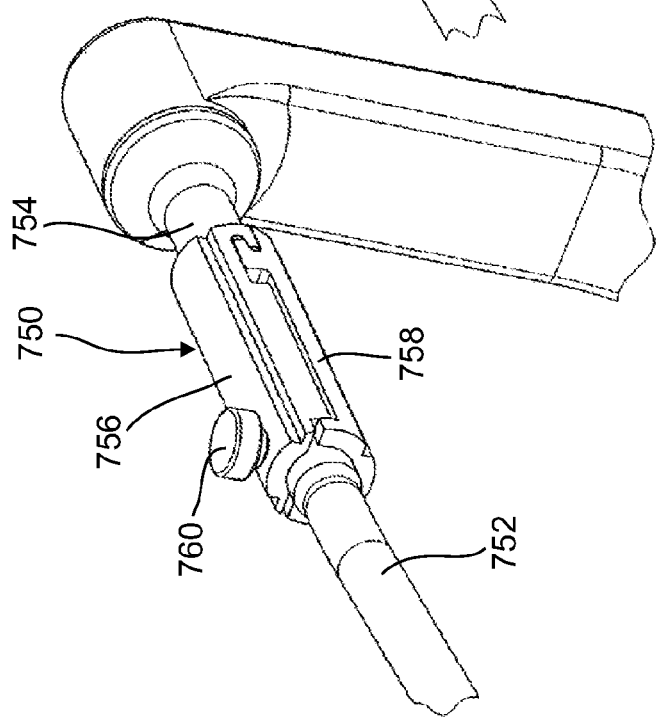

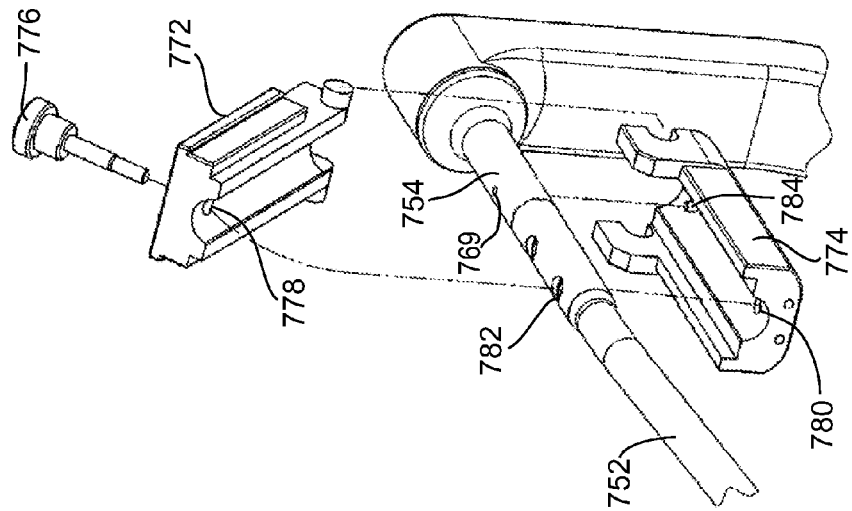
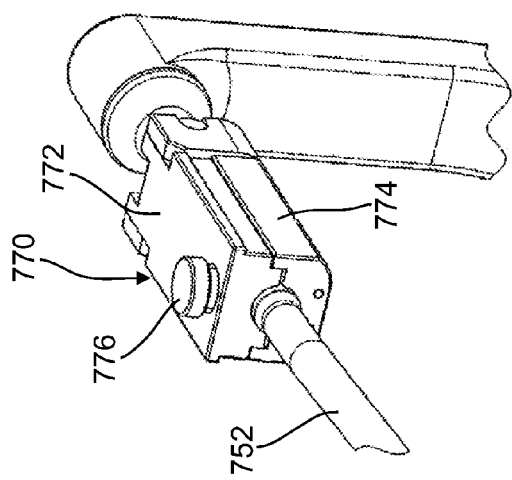

COMPOSITE MATERIAL BONE IMPLANT

RELATED APPLICATIONS

This Application is a National Phase of PCT Patent Application No. PCT/IB2011/052468 having International filing date of Jun. 7, 2011, which claims the benefit of priority under 35 USC §119(e) of U.S. Provisional Patent Application Nos. 61/344,182 of Beyar filed on Jun. 7, 2010, 61/443,308 of Beyar, et al. filed on Feb. 16, 2011 and 61/486,280 of Beyar et al. filed on May 15, 2011.

PCT Patent Application No. PCT/IB2011/052468 is also related to PCT Patent Application No. PCT/IB2010/050225 to Beyar, filed on Jan. 18, 2010.

The contents of the above applications are all incorporated by reference as if fully set forth herein in their entirety.

FIELD OF INVENTION

The present invention in some embodiments thereof, relates to composite material bone implant components, devices and systems, and/or to methods for manufacturing and using such components, devices, and systems, and to surgical instrumentation and procedures used during implantation. More particularly, but not exclusively, the invention relates to bone-supporting components such as bone nails and bone plates, to implant fixation components such as bone screws and pegs, formed of fiber-reinforced polymer matrix composites or self-reinforcing polymers, and to tools and accessories for performing surgery using such components.

As used herein, the term "bone implants" encompasses, but is not limited to, hip joints, knee joints, shoulder joints, bone screws, bone instruments, bone plates, pegs, and intramedullary nails, including proximal femur nails, typically including screw holes for receiving bone fixation screws, as well as dental bone implants.

BACKGROUND OF THE INVENTION

Bone-supporting components such as bone plates and intramedullary nails (bone nails) have become a treatment of choice for the fixation of bone fractures, especially fractures of long bones (e.g., the humerus, tibia and femur), and in non-broken bones to prevent fractures. Typically, bone nails are rod-shaped devices configured and constructed to be secured (interlocked) to a bone using one or more fixation components which anchor the bone nail into the bone in order to carry the loads until the bone fracture is cured.

Bone plates are generally (but not exclusively) used in cases that a bone nail can't be used, and are designed for implantation on the bone surface.

Implant fixation components include bone screws, rods and pegs. Bone screws are used for fixation at one or both ends of a nail or along a bone plate. Implant fixation components generally referred to as "pegs" are round unthreaded rods (or threaded at one end), conventionally formed of metal that are usually (but not exclusively) used to help anchor bone plates to a bone such as the proximal humerus or the distal radius for fracture fixation. The rod goes into a hole drilled into the bone.

In the art, the entire implant is generally constructed from metal, such as titanium, stainless steel, or a cobalt-chromium alloy. Although metallic implants provide numerous advantages, they also have a few drawbacks. Metal construction normally provides adequate bending strength, thus reducing problems associated with implant fracture. However, the rigid metal implant creates a relative high degree of stresses in certain regions of the bone, while, on the other hand, does not provide for sufficient load transfer resulting in stress shielding. Both high stress and stress shielding can cause bone deterioration and resorption, leading to areas of bone weakness and loss of bone support for the implant (e.g., intramedullary nails and stem components of joint replacement systems). In addition, metals may result in artifacts in CT and MR imaging. In addition metals can mask (i.e., block) radiation treatment in cancer cases. Furthermore, metals such as stainless steel and cobalt chromium may cause biocompatibility problems related to corrosion and sensitization reaction (mainly due to allergy to nickel).

Also, conventional metal fixation components, e.g., bone-supporting components (e.g., intramedullary nails and bone plates) and pegs and screws can mask the fracture and limit the ability of the surgeon to set the fracture correctly. Metal bone-supporting components and fixation components may also limit the ability to see the healing process in X-Rays.

Non-metal implants made of a lighter and more flexible material, yet having sufficient strength for load bearing, have been suggested in the past. In particular, composite material implants, for example formed of polymer reinforced with fibers, are disclosed in U.S. Pat. Nos. 4,750,905, 5,181,930, 5,397,358, 5,009,664, 5,064,439, 4,978,360, 7,419,714 the disclosures of which are incorporated herein by reference.

U.S. Pat. No. 5,009,664 describes a tubular, curved marrow nail, made of carbon fibers, which are preferably knit in a crisscross fashion, saturated in a hardenable plastic, with a conically tapered distal tip.

U.S. Pat. No. 5,181,930 describes an implant comprising an elongated core formed of continuous filament fibers embedded in thermoplastic polymer. The core is encased within a filler, made of a non-reinforced polymer which is molded around the core to proximate the final desired shape of the implant. A sheath, composed of reinforced fibers embedded in a polymer, is spiral wound around the filler, at angles (orientations) which may vary along the implant axis.

Although known composite material implant technology can provide several advantages, there are also some limitations. In contrast to metal, composite material implants are radiolucent, i.e., do not block most of the radiation coming from x-ray systems such as fluoroscopy, and hence their implantation and tracking during follow-up may be difficult. For bone nails or plates, accurate insertion of the screws into the holes in the nail/plate is crucial to the success of the operation, especially where no aiming device is used.

U.S. Pat. No. 7,419,714 describes a bone screw or plate formed of a composite of polymer or ceramic material.

Currently available bone implants, such as bone plates, include pre-drilled holes for the fixation devices which anchor the implant to the bone and optionally lock the implant in place and/or provide for bone fragments compression.

SUMMARY OF THE INVENTION

There is provided in accordance with an exemplary embodiment of the invention, a bone implant component comprising bone plate formed of a fiber-reinforced polymer composite in which the reinforcing fibers are along the length of the plate, wherein the bone plate is radiolucent.

In an exemplary embodiment of the invention, the component includes at least one radiopaque marker that delineates at least part of the contour of plate. Optionally the marker is comprised of a metal wire.

There is provided in accordance with an exemplary embodiment of the invention, a bone-supporting component formed of a fiber-reinforced polymer composite configured to be anchored by a plurality of fixation components received in passages therein, wherein at least some features of the component not preformed so that it may be reconfigured by the surgeon during the implantation procedure by forming the required features.

In an exemplary embodiment of the invention, the features are drilled and/or tapped passages, or cut or sawed portions.

Optionally or alternatively, the component is further including at least one built-in reconfiguration guide to facilitate formation of fixation component passages or for otherwise reconfiguring the bone-supporting component. Optionally, the reconfiguration guide includes one or more indentations in the surface of the component. Optionally, the indentations form blind holes, or blind slots, or elongated blind grooves, or cutting lines.

In an exemplary embodiment of the invention, the component is further including at least one pre-drilled passage for receiving a fixation component.

There is provided in accordance with an exemplary embodiment of the invention, a fixation component for a bone implant formed of a fiber-reinforced polymer composite having a body and a head at the proximal end of the body which is integrally formed with the body, wherein the body includes an elongated portion having longitudinal reinforcing fibers disposed along its length, and the head includes reinforcing fibers disposed mainly in a circular or spiral pattern.

There is provided in accordance with an exemplary embodiment of the invention, a bone implant component, formed mainly of fiber-reinforced polymer composite material comprising:

a core including elongated reinforcing fibers to resist mainly bending forces; and a sleeve enclosing the core that includes spirally wound fibers to resist mainly torsional forces. Optionally, the component is a bone screw.

In an exemplary embodiment of the invention, the body further includes chopped fibers of reinforcing material. Optionally, the chopped fibers are of different lengths and/or are non-uniformly oriented.

In an exemplary embodiment of the invention, the reinforcing fibers of the sleeve are oriented in a spirally wound layer oriented at 45 degrees relative to the core.

In an exemplary embodiment of the invention, the sleeve is formed of two or more spirally wound layers, with alternating layers oppositely wound at about ±45 degrees relative to the longitudinal axis of the core.

In an exemplary embodiment of the invention, the composite material is in the form of pre-impregnated (prepreg) tapes having the fibers running length-wise along the tape. Optionally, the cores are formed by layers of prepreg tape disposed one on top of the other. Optionally or alternatively, the sleeves are formed of prepreg tapes, wound spirally over the core.

There is provided in accordance with an exemplary embodiment of the invention, a composite implant having fibers having different mechanical properties disposed at different places in the implant. Optionally, at least 20% of the fibers used in the sleeve have different strength in tension and different modulus of elasticity from fibers are used in the cores.

There is provided in accordance with an exemplary embodiment of the invention, a composite bone implant component including at least one radio-opaque marker located at a distal end of the body, or extending most the length of the body. Optionally, the at least one marker is formed of metal wires embedded inside the components. Optionally or alternatively, the at least one marker is formed of a hollow tube.

There is provided in accordance with an exemplary embodiment of the invention, a bone implant kit comprising:

a bone-supporting component formed mainly of a fiber-reinforced polymer composite;

one or more fixation components for the bone-supporting component; and a radiolucent drill guide to facilitate drilling for insertion of the fixation components. Optionally, the bone-supporting component includes pre-drilled passages for the fixation components so that only the bone needs to be drilled during the implantation procedure. Optionally, the bone-supporting component is supplied undrilled, and both the bone and passages for the fixation components are drilled during the implantation procedure.

In an exemplary embodiment of the invention, the bone-supporting component is a radiolucent bone plate.

In an exemplary embodiment of the invention, the kit including an arrangement for removing drilling debris created by drilling for insertion of a bone implant comprising a suction element configured for connection to a source of suction and for disposal of a suction port on the suction element adjacent to a drill bit during drilling; and In an exemplary embodiment of the invention, the kit further includes an arrangement providing irrigation fluid to a drilling site comprising an irrigation element configured for connection to a source of irrigation fluid, wherein the irrigation element includes a fluid outlet port configured to be positioned adjacent to a drill bit during drilling.

There is provided in accordance with an exemplary embodiment of the invention, a fixation component for a bone-supporting component of a bone implant comprising:

a body including a core, a sleeve surrounding the core, and a head portion, wherein the body is formed of a fiber-reinforced polymer composite; and a further portion formed of a hard material to strengthen the implant and/or enhance the hardness of the implant and/or to impart surface properties.

In an exemplary embodiment of the invention, the further portion is a layer covering an elongate section of the body or the entire body. Optionally or alternatively, the further portion is a metal coating or a metal tape. Optionally, the fixation component is threaded at least in its distal region, and the metal coating or tape disposed over the threads. Optionally, the coating or tape is discontinuous, and does not cover the root portions of the threads.

In an exemplary embodiment of the invention, the coating or tape is continuous, and a portion covering the crown portions of adjacent threads extends into and overlaps in the root portions between the threads. Optionally, at least some overlapping portions are welded.

In an exemplary embodiment of the invention, the further portion is an insert at the distal end of the component.

There is provided in accordance with an exemplary embodiment of the invention, a bone implant formed of a fiber-reinforced polymer matrix composite comprising:

a bone-supporting component;

a fixation component configured to be received in passages in the bone-supporting component; and a locking element for attaching the fixation component to a bone-supporting component.

There is provided in accordance with an exemplary embodiment of the invention, a bone implant formed of a fiber-reinforced polymer matrix composite comprising:

a bone-supporting component;

a fixation component configured to be received in a passage in the bone-supporting component; and a sleeve between the fixation component and the passage. Optionally, the sleeve is configured to reduce friction between the fixation component and the passage. Optionally or alternatively, the sleeve is threaded.

There is provided in accordance with an exemplary embodiment of the invention, a method of treating a bone fracture comprising:

positioning a bone-supporting component at a desired position in relation to a fracture site, wherein the bone-supporting component is formed of a fiber-reinforced polymer composite manufactured without pre-drilled passages for receiving fixation components; and reconfiguring the bone-supporting component to provide passages for one or more fixation components or other desired features by removal of material from the bone-supporting component before or during implantation surgery. In an exemplary embodiment of the invention, bone fragments are manipulated while viewing through the component, for example, using an x-ray imager. Optionally, the bone-supporting component is reconfigured by one or more of drilling, or tapping, or cutting, or sawing. Optionally or alternatively, the reconfiguring is performed using a radiolucent drill.

In an exemplary embodiment of the invention, the reconfiguring is performed before or after the bone-supporting component is positioned at the fracture site.

There is provided in accordance with an exemplary embodiment of the invention, a method of manufacturing a fixation component for a bone implant comprising:

compression molding a core of relatively straight elongated fibers within a polymer matrix; and machining the core to form a thread. Optionally, the method includes forming at least one spirally wound layer over the core. Optionally or alternatively, the pitch of the spirally wound layer matches the thread pitch. Optionally or alternatively, the method includes forming a spirally wound profile layer having a cross section substantially matching said thread.

In an exemplary embodiment of the invention, the fixation component is formed of prepreg tapes of fiber-reinforced polymer composite. Optionally or alternatively, the method includes forming an external titanium layer on the fixation component.

There is provided in accordance with an exemplary embodiment of the invention, a bone implant component formed of a fiber-reinforced polymer composite having a body and a head at the proximal end of the body which is integrally formed with the body, wherein the body includes an elongated portion having longitudinal reinforcing fibers disposed along its length, and the head includes a coupling element for coupling the component to an insertion tool, and is formed with reinforcing fibers disposed circumferentially or spirally wound around the coupling element.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

BRIEF DESCRIPTION OF THE FIGURES

Some embodiments of the invention are herein described, by way of example only, with reference to the accompanying drawings. In this connection, it is stressed that particular features shown in these embodiments are by way of example and for purposes of illustrative discussion. Other embodiments may include other combinations of features as will be apparent to those skilled in the art from the drawings and the accompanying description.

In the drawings:

FIGS. 7A-7D, FIGS. 8A-8C and FIG. 9 illustrate composite material bone screws, in accordance with some embodiments of the invention;

FIG. 16A is a side view, and FIGS. 16B-16C is transverse sectional views that schematically illustrate options for radiopaque marking of a bone screw;

FIGS. 20A and 20B top and side perspective and vertical sectional views respectively that illustrate another drill sleeve 670 according to some embodiments of the invention;

FIGS. 22A and 22B are schematic top views that illustrate ways to provide for visualization of bone plates under fluoroscopy during implantation and/or at follow-up in some embodiments of the invention.

FIGS. 23A and 23B are assembled and partially exploded views of some embodiments of the invention which may be used to share the loads exerted on the nail-handle connection area during insertion of the nail into the bone;

FIGS. 24A and 24B are, respectively, assembled and partially exploded views similar to FIGS. 23A and 23B showing another nail installation device 770 according to some embodiments of the invention;

DETAILED DESCRIPTION OF SOME EMBODIMENTS OF THE INVENTION

Figure 1:
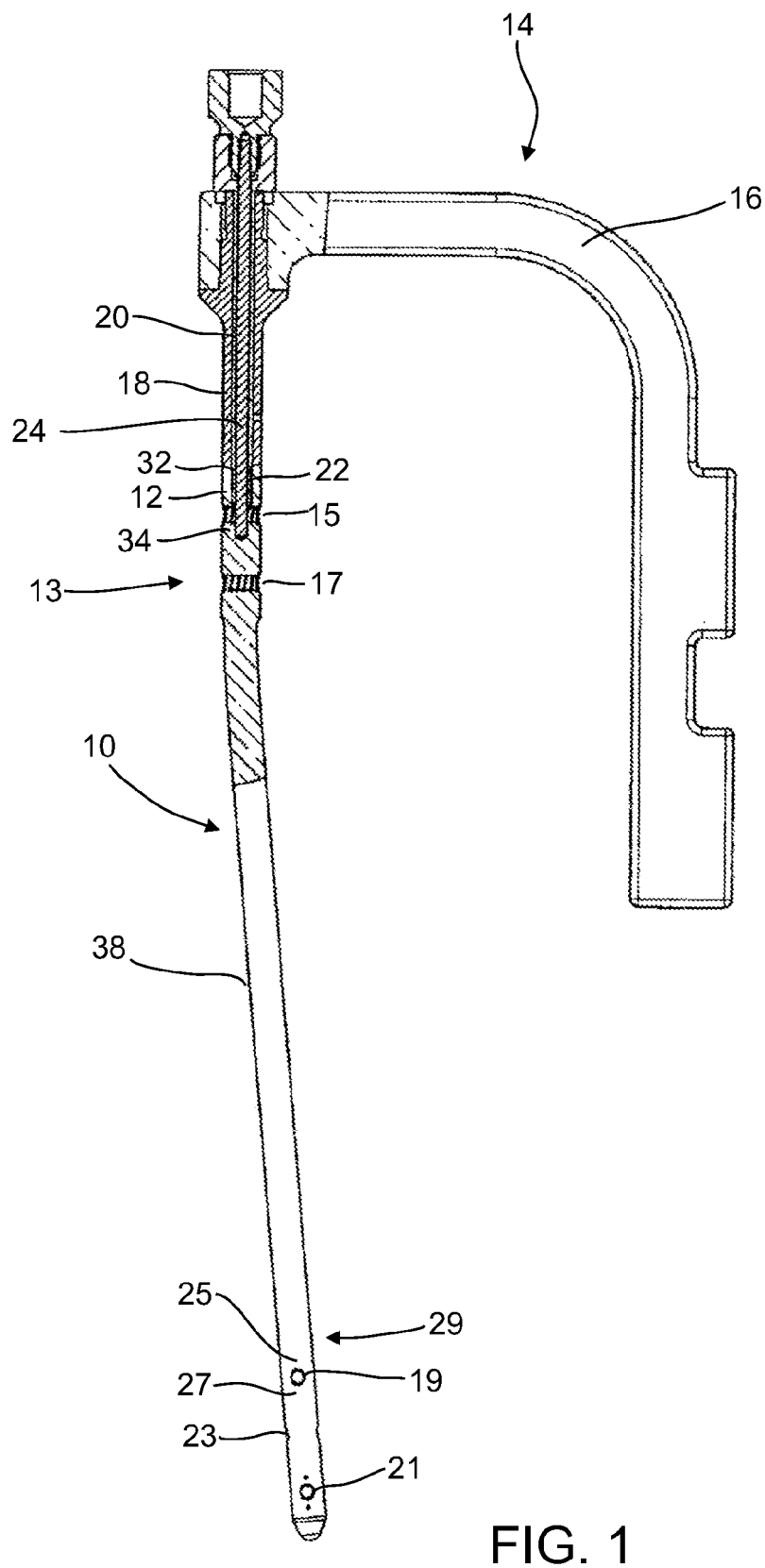
FIG. 1 illustrates a composite material intramedullary nail connected to an insertion handle, in accordance with some embodiments of the present invention.

Overview of Features of Some Embodiments of the Invention

The present invention in some embodiments thereof, relates to composite material bone implant components, devices and systems, and to methods for manufacturing and using such components, devices, and systems, as well as to surgical instrumentation and procedures used during implantation. More particularly, but not exclusively, the invention relates to bone-supporting components such as bone nails and bone plates, to implant fixation components such as bone screws and pegs formed of fiber-reinforced polymer matrix composites.

In the following overview, except as otherwise indicated, it is to be understood that the implants described are all formed mainly (e.g., at least 50%, 60%, 70%, 80% or intermediate amounts of the load bearing portions thereof) of a fiber-reinforced polymer composite.

An aspect of some embodiments of the invention pertains to a bone implant component, e.g., a bone nail, a bone screw, or a peg formed of a core including different fiber directions and/or types in different parts thereof. In one embodiment, the implant includes elongated reinforcing fibers to resist mainly bending forces, optionally in a core thereof. Optionally or alternatively, bone nails and screws or other fixation elements such as pegs may also have a sleeve enclosing the core that includes spirally wound fibers to resist mainly torsional forces.

In an exemplary embodiment of the invention, an elongate implant has a length to width ratio of at least 1:2, 1:3, 1:4 or more.

In an exemplary embodiment of the invention, the body includes chopped fibers of reinforcing material. Optionally, the chopped fibers are of different lengths and/or are non-uniformly oriented.

In an exemplary embodiment of the invention, the reinforcing fibers of the sleeve are oriented, for example, at about (e.g., within 5, 10, 20 or intermediate degrees of) 45 degrees relative to the longitudinal axis of the core. Optionally, the sleeve is formed of two or more spirally wound layers, with alternating layers oppositely wound at, for example, ±45 degrees relative to the longitudinal axis of the core.

An aspect of some embodiments of the invention pertains to implant components in which different types of fibers having different mechanical properties are used in different places in the implant. For example in a nail, longitudinal fibers having high elongation at break and low modulus of elasticity may be used in the core. In the sleeve, low elongation to break and high module of elasticity, may be preferable so the nail will be elastic for bending and rigid for torsion.

Optionally, the polymer forming the matrix in the various embodiments described above is polyetherketoneketone (PEKK), polyetheretherketone (PEEK), or any other suitable biocompatible polymer.

Optionally, the composite material forming the components in the embodiments described above is in the form of pre-impregnated (prepreg) tapes having the fibers running length-wise along the tape. Optionally the cores are formed by layers of prepreg tape disposed one on top of the other. In some embodiments of the invention, the sleeves are also formed of prepreg tapes, wound spirally over the core.

In some embodiments, all or part of the bone implant is coated with a material to improve the implant osteo-conductive and/or osteo-inductive properties, to enhance implant ability to integrate in the bone and to support bone ingrowth. Optionally, the coating is formed of porous titanium or hydroxyapatite (HA). Optionally, in some embodiments, one or more antibiotics to avoid infection, and/or bone morphogenetic proteins (BMP) may be added to the coating in the area of the fracture to promote bone regrowth.

Optionally, a polymer layer is a bioresorbable or biodegradable material. Optionally, the layer is formed of polydioxanone or polycarbonate. These may be used as a coating on the inside of the fixation component-receiving passages or on the entire implant to reduce wear of the composite material during implantation.

An aspect of some embodiments of the invention pertains to a bone-supporting component e.g., a bone nail or bone plate, configured to be processed during or right before surgery. In one example, the component is sawn. Optionally or alternatively, the component is drilled, cut, nibbled, tapped and/or notched or otherwise has material removed thereof during surgery or right before. Optionally, the processing is decided based on a CT, X-Ray, MRI or visual observation of a treated area. Optionally, the components is modified even after implantation, for example, to add a fixation element (e.g., a screw) therethrough.

In an exemplary embodiment of the invention, the component has a plurality of guide locations or pre-designated locations for processing, for example, in the form of thinned areas, missing areas and/or grooves.

In an exemplary embodiment of the invention, the implant is a plate or nail which is meant to be anchored by a plurality of fixation components received in passages therein, in which at least some passages are not predrilled, and the bone supporting component is configured so that at least some least some fixation device passages may be drilled by the surgeon during the implantation procedure. (For simplicity, these are collectively referred to as "undrilled".)

Optionally, undrilled components include at least one built-in reconfiguration guide to facilitate formation by the surgeon of fixation component passages or for otherwise reconfiguring the bone-supporting component. Optionally, the reconfiguration guide is an indentation in the surface the component defining blind holes, narrow-diameter holes, dimples, blind slots, elongated blind grooves and/or cutting lines. Optionally, one or more markers (e.g., visual and/or radio-opaque) are provided to indicate such desired processing locations. Optionally, markers are arranged as a grid, optionally rectangular.

In another example, a nail or other elongate implant is cut to length, for example, at one or both ends, to match a particular patient.

In an exemplary embodiment of the invention, the implant is drilled while inside the body. Optionally, suction and/or washing fluid are provided, for example, for removing debris and/or cooling.

In an exemplary embodiment of the invention, the implant includes at least one attachment location, for example, a hole, for attaching a drill guide or cutting tool guide thereto, during processing.

In an exemplary embodiment of the invention, instructions for processing are provided on or with the implant, for example, in a packaging. Optionally, one or more size markings are provided on the implant to indicate the effect of such processing.

An aspect of some embodiments of the invention pertains to a bone implant including a bone-supporting component, e.g., a bone nail or and a fixation component, e.g., a bone screw, each having a body and/or a head portion at the proximal end of the body which is integrally formed with the body. In such embodiments, the bodies include elongated portions having longitudinal reinforcing fibers disposed along their length, and the heads include reinforcing fibers disposed mainly in a different direction, for example, in a circular or spiral pattern.

An aspect of some embodiments of the invention pertains to combination of a bone implant including a bone-supporting component, one or more fixation components for the bone-supporting component; and a radiolucent drill guide to facilitate drilling for insertion of the fixation components.

Optionally, the bone-supporting component includes predrilled passages for the fixation components so that only the bone is drilled during the implantation procedure. Optionally, the bone-supporting component is supplied undrilled, and both the bone and passages for the fixation components are drilled during the implantation procedure.

In an exemplary embodiment of the invention, use is made of the fact that the composite implant is mainly transparent (e.g., blocks less than 5%, 10%, 30%, 50%, 90% or intermediate amounts of x-ray radiation, depending on the implementation) and bone can be viewed through it. This allows, for example, reduction of a fracture, drilling in bone and/or processing an implant while the implant is in the body and using x-ray (for example) to view the relative locations of bone fragments and the implant. Optionally, a plurality of implants are aligned, inside the body to each other and to bone, using such imaging after implantation. Optionally, non-radiolucent screws are used with such implants.

An aspect of some embodiments of the invention pertains to a fixation component for a bone-supporting component of a bone implant formed of a body optionally including a core, a sleeve surrounding the core, and a head portion, and a further element formed of a hard material to strengthen the implant and/or enhance the hardness of the implant and/or to impart other desired properties.

In an exemplary embodiment of the invention, the further element is a layer covering the head portion or the entire body. Optionally or alternatively, the fixation component is threaded at least in its distal region, and the layer is a metal coating or a metal tape wound over the threads. Optionally, the layer is discontinuous, and does not cover the root portions of the threads. Alternatively, the layer is continuous, and the portion covering the crown portions of adjacent threads extends into and overlaps in the root portions between the threads.

Optionally or alternatively, the layer is provided in a tool-engaging portion, such as an inner hex-shaped socket or screwdriver receptacle.

Optionally or alternatively, the layer is provided at an interface between a fixation component and a second composite or other material.

An aspect of some embodiments of the invention relates to a method of reducing wear, debris and/or damage in a composite implant or implant system. In an exemplary embodiment of the invention, locations prone to wear or damage are covered and/or provided with a metal or polymer layer or element which provides reduced friction, reduced wear and/or larger or small (e.g., as desired) wear particles. In an exemplary embodiment of the invention, the layer is part of a fixation element or a different implant. Optionally or alternatively, the layer is a separate component.

In an exemplary embodiment of the invention, fiber direction at a location of expected wear is oriented perpendicular to a wear direction, so as to reduce damage to an implant.

An aspect of some embodiments of the invention pertains to formation of a threaded bone screw by compression molding a rod, optionally from layered prepreg tapes, followed by machining to form the threads. Alternatively, over the molded core, there is formed a spiral winding, optionally formed of one or more prepreg tape layers, and optionally in which winding pitch matches the desired screw pitch. Optionally, when two or more layers are used they are wound in alternating clockwise and counterclockwise orientations.

Optionally, the screw is further machined to produce the desired configuration of the thread teeth. Optionally, a profile winding, for example that has a relatively triangular cross section is spirally wound around the core.

An aspect of some embodiments of the invention pertains to fixation components including a locking element for attaching the fixation component to a bone-supporting component. Optionally, the locking element is a spring constructed and configured to expand radially to engage within the passage. Optionally, the spring is a locking ring. Optionally the spring is an integral part of a metal portion of the fixation component. Optionally, the locking element is formed by a portion that is oversized relative to the passage. Such a locking element is compressed during installation, and re-expands after it exits the distal side of the passage. Optionally the fixation component is slightly larger than the passage in the supporting implant, and during insertion, is compressed locally the supporting implant and lock into it.

An aspect of some embodiments of the invention pertains to bone implant components that include radiopaque markers. Optionally, in the case of the fixation component or a bone nail, the marker is located at a distal end of the body, or extends most the length of the body.

In the case of the bone-supporting component such as a bone plate including a head portion, the radiopaque marker extends around at least part (e.g., 10%, 30%, 40%, 60% or intermediate or greater amounts) of the contour of the head portion or head portion (e.g., when viewed from a side of the implant). Optionally, the radiopaque marker extends around the entire contour of the bone plate. Optionally, the radiopaque marker is on the side of the bone plate facing outward after implantation. Optionally, the contour marker is within 1 mm or 0.5 mm, of the outer counter. Optionally, a marker indicating the projection of the implant is provided as well, for example, a circle or a square, or an arrangement of markers whose distortion indicates if the implant is viewed from a correct direction.

In some embodiments of the invention, the markers are formed of metal wires, for example, tantalum, gold, or platinum or similar embedded inside the components. For example a tantalum wire having diameter of 0.2-0.5 mm is suitable.

Optionally or alternatively, the marker comprises a plurality of markers, for example, beads or wire sections. Optionally, such markers are used to indicate pre-drilled holes or slots and/or locations for processing.

An aspect of some embodiments of the invention pertains to a bone-supporting component, in which opposite ends of fixation component passage include reinforcing fibers optionally having opposite U-shaped configurations to help reduce wear and/or breakage due to forces from a fixation device.

Alternatively, the cylindrical part of the body is coated with a material to reduce friction between the body and the passage. Optionally, the coating is a polymer, for example Teflon. Optionally, the coating is a ceramic material, for example alumina.

In some embodiments of the invention, there is a bearing, for example, a hollow cylinder or cylinders, between the passage and the portion of the fixation component body located in the passage when the device is implanted.

Optionally or additionally, the surface of the passage bears a metal coating to help reduce formation of debris during implantation.

An aspect of some embodiments of the invention relates to drilling and fixation component insertion accessories, optionally provided in kit form together with one or more implants and/or fixation devices. Such accessories are optionally configured to be temporarily attached to the implant components to assist a surgeon in properly positioning and anchoring the components.

In some embodiments, the accessories include one or more of a targeting device for drilling holes to anchor the head of a bone plate, a drill guide for holes to anchor bone nails, and fixation component insertion guides, or accessories that incorporate one or more of the described functions. Optionally, the accessories are formed of metal, or of a radiolucent material, for example, a polymer. Optionally, the polymer is fiber-reinforced.

In an exemplary embodiment of the invention, the accessories are configured to be disposable after a single use, for example, due to wear or difficulty in sterilization. Optionally, the accessories supplied pre assembled with the implant.

In some embodiments of the invention, a bone implantation system includes one or more fixation components, one or more bone-supporting components, and one or accessories, for example, as described above, and may also include a bone nail insertion support apparatus that is used to share the loads exerted on the nail-handle connection interface during insertion of the nail into the bone.

In an exemplary embodiment of the invention, the accessories include one or more radiolucent drill guide, optionally configured for attachment to the composite bone implant. Optionally, the drill guides are drilled during or before surgery, at a desired angle of access for the drill. Optionally or alternatively, the drill guides are formed, for example, using computer-controlled 3D prototyping tools, for example, based on one or more 3D CT images.

In some embodiments of the invention, the system also may include a radiolucent drill connector, one side of which is configured for connection to a power unit. The other side is configured for connection to a drilling tool. Optionally, the connector includes a clutch arrangement to assure the drill bit operates only when the surgeon holds the power unit and intentionally engages the clutch, e.g., by pushing the power unit toward it. Optionally, the connector (or a drill) is not straight, so that part of the connector (or drill) is not blocking the view of an x-ray imager.

In some embodiments of the invention, the radiolucent drill is a single use device, having in its proximal side, handle, electric motor, battery, switch and optionally gear, and in his distal radiolucent side, radiolucent drill bit connector, and optionally right angle gear such as bevel gear or worm gear. Optionally, a radiolucent shaft transmits the torque from the motor or the proximal gear, between the proximal and the distal sides of the device.

An aspect of some embodiments of the invention relates to drilling passages in the bone-supporting component and/or fractured bones during an implant procedure while applying suction to aid in removal of drilling debris and/or irrigating. Optionally, a drilling instrument or tool is contained within a tube that enables suction of the drilling debris. Optionally, the drilling tool is cannulated and suction is performed through the cannulation. Optionally, the suction is performed directly through the cannulation. Optionally, the suction is performed through a separate tube located in the cannulation.

In some embodiments of the invention, the drilling site is irrigated, e.g., with sterile saline solution during drilling. Optionally, with a cannulated drilling tool, the cannulation is used to provide the irrigation fluid, and an external tube provides the suction. Optionally, the cannulation is used to provide the suction, and an external tube provides the irrigation fluid. Optionally, the external tube surrounds the drilling tool. Optionally, the external tube is completely separate, and is positioned adjacent to the drilling tool.

In some embodiments of the invention, where the drilling tool is not cannulated, separate tubes, either surrounding the drilling tool, or adjacent to it are used to supply irrigation fluid and for suction.

In some embodiments of the invention, irrigation is not employed, and suction of drilling products is performed simultaneously from the drilling tool cannulation (with/without an internal suction tube) and from an external suction tube.

The irrigation can help cool the implant and surrounding tissue while drilling is being performed, for example, to reduce or avoid the risk of damage of patient tissue and/or devices.

In some embodiments of the invention, a bone implant device include fixation components and bone-supporting components having various combinations of features as described above, and as described in detail below.

In some embodiments of the invention, implant kits include fixation components and bone-supporting components and accessories having various combinations of features, also as described above, and as described in detail below.

Exemplary Bone Nail Embodiments:

FIG. 1 illustrates schematically in a side view, a bone-supporting component of an implant, intramedullary nail 10, for example a humeral nail, connected at its proximal end 12 to an insertion handle 14. Illustrated nail 10 is configured for use in treating humeral fractures. However, it should be understood that this and other embodiments are applicable to other intramedullary nails as well, such as nails for tibia bones, femur bones, or other bones. Typically nail 10 is between about 7 and about 12 mm in diameter. In some embodiments of the invention, the radiolucent drill is a single use device, for example, having in its proximal side, handle, optionally electric motor, optional battery, switch and optionally gear, and in his distal radiolucent side, radiolucent drill bit connector, and optionally right angle gear such as bevel gear or worm gear. Optionally, a radiolucent shaft transmits the torque from the motor or the proximal gear, between the proximal and the distal sides of the device.

The proximal region 13 of nail 10 includes two holes 15, 17 positioned in the same orientation for the insertion of screws that fix the nail to the bone. The distal end 29 of nail 10 includes three additional holes 19, 21, 23 for bone screws. Other configurations, numbers, and orientations of screw holes may alternatively be provided.

Radiopaque markers 25, 27, optionally made of tantalum or other suitable metal, are provided near each screw hole to assist in drilling and screw placement. These are illustrated as diametrically opposite dots, but can have other configurations, for example, circles around the holes. Suitable radiopaque materials include tantalum, gold, platinum, or other biocompatible metal.

As will be understood, nail 10 is configured to be inserted into the medullary canal by the surgeon during the implant procedure with the assistance of insertion handle 14.

Insertion handle 14 is an example of a suitable device for performing the actual insertion. Handle 14 comprises a curved portion 16 and a straight tube 18, which engages with the proximal end 12 of nail 10. Curved portion 16 is optionally formed of metal but is preferably formed of composite material to reduce interference with radiographic visualization during implantation.

The process of insertion of nail 10 into the bone may involve manipulation of the nail-handle assembly and thus may impose bending and torsional forces on the nail. Therefore, an inner rod 24, optionally formed of metal, for example, surgical grade stainless steel is temporarily installed between nail 10 and handle 14, to strengthen the connection area for bending. Rod 24 is introduced via a cannulated nail adapter 20 which may be part of handle 14, or a separate element.

Figure 2:
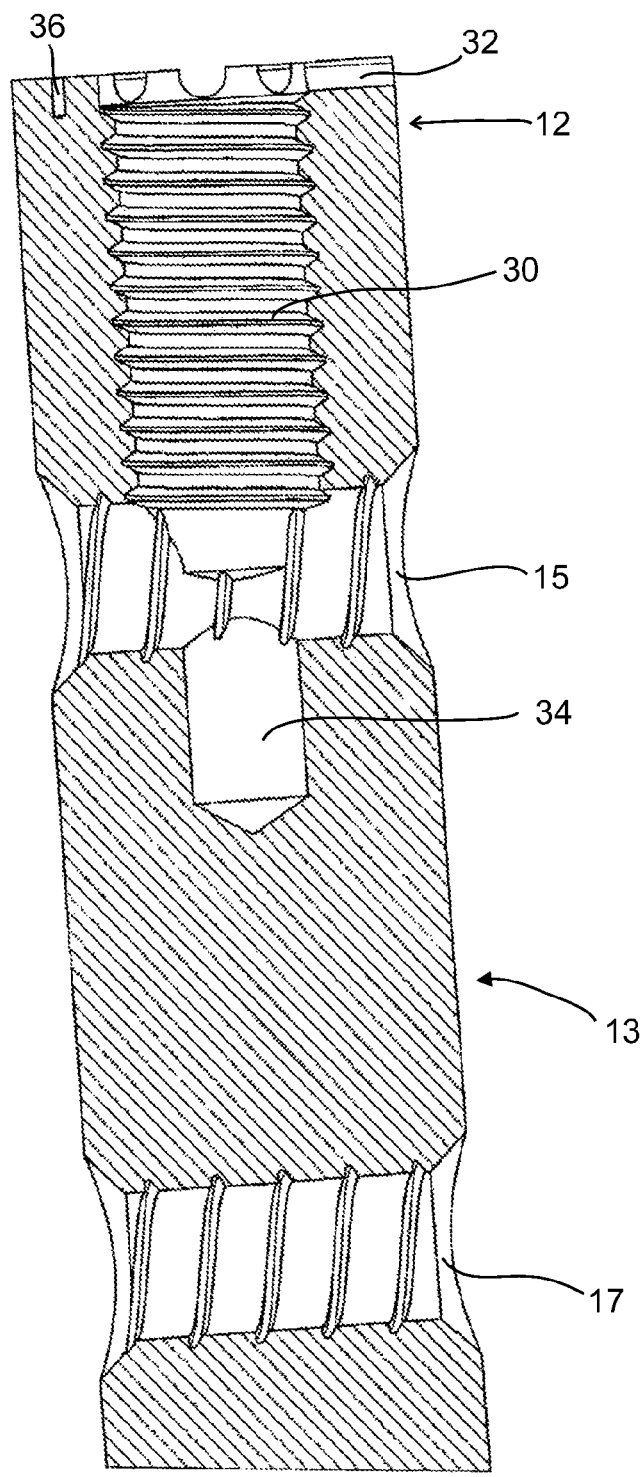
FIG. 2 is a cross-sectional view of the proximal region of the nail shown in FIG. 1.

As shown in FIG. 2, rod 24 is configured to penetrate into a bore 34 at the proximal end of the nail. Optionally the diameter of the bore 34 is in the range of 2 to 5 mm Optionally, rod 24 extends beyond the proximal hole 15 in the nail. Following nail introduction part way into the bone, the inner rod 24 is removed.

According to bench testing performed by the inventors, inner rod 24 improved the bending properties of the nail-handle connection area.

Figure 3:
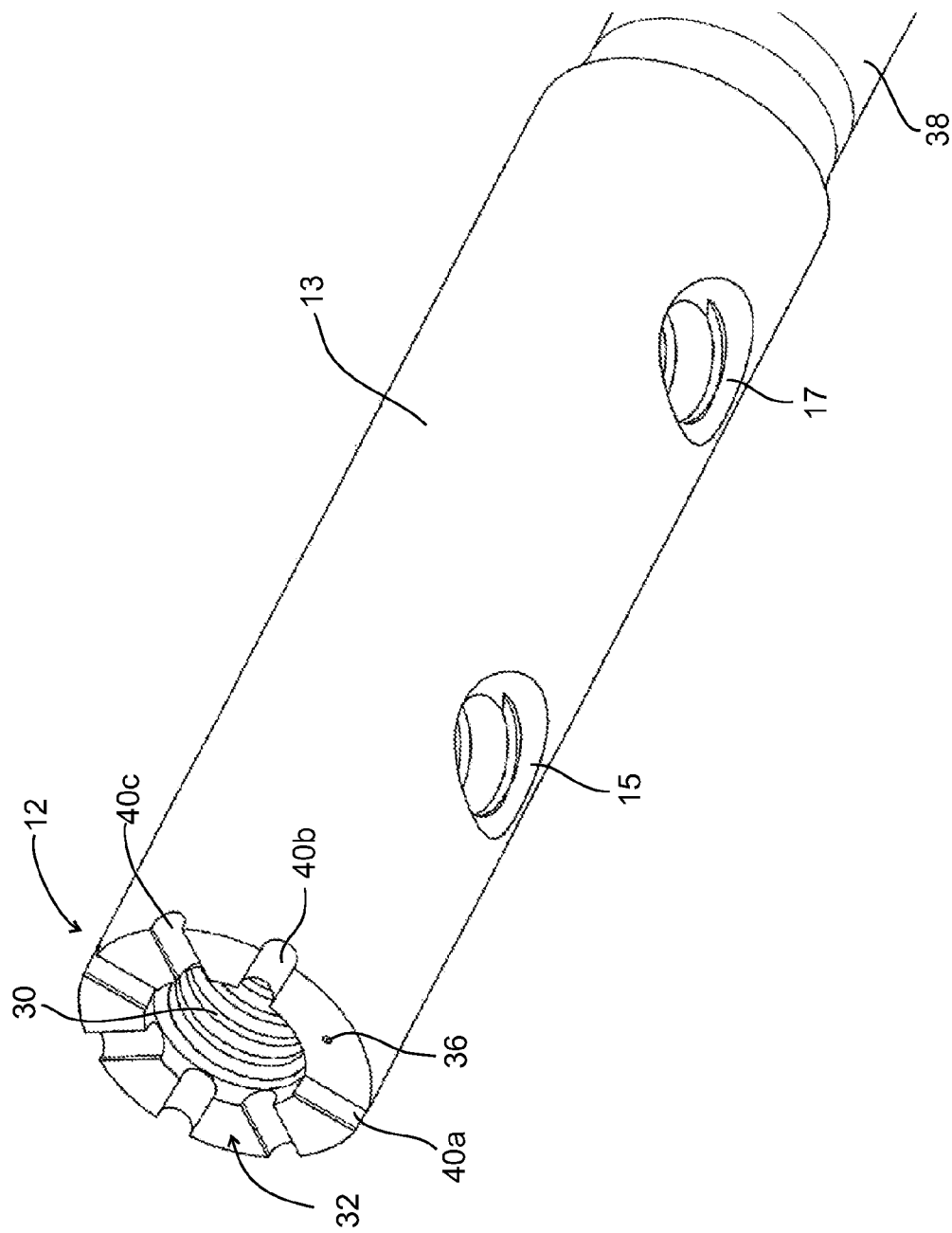
FIG. 3 is an enlarged perspective view of the proximal region of the nail of FIGS. 1 and 2.

FIGS. 2 and 3 are respectively enlarged sectional and perspective views of the proximal region 13 of the nail 10 illustrated in FIG. 1. As shown in FIGS. 2 and 3, the nail includes a threaded end-portion 30, to which the nail adapter 20 is connected, and a connection detail 32 at proximal end 12 having slots 40 configured to engage matching protrusions at the end of insertion tube handle tube 18 when it is connected to the nail 10 (see also FIG. 3).

One or more radial slots and complementary teeth may be provided. However, according to bench testing performed by the inventors, increasing the number of the slots in the connection detail (and the complementary teeth at the handle end), leads to improved torque transfer.

By way of example, as shown in FIG. 3, connection detail 32 includes seven radial slots 40a, 40b, 40c, etc., although other numbers and shape of slots are also feasible. Optionally, the slots 40 are positioned so that the distance between at least two adjacent slots 40a and 40b is different than the distance between other adjacent slots, thus providing only a single orientation of connecting the nail to handle 14, and helps assure introduction of the nail into the bone in the correct orientation.

The connection detail 32 (shown enlarged in FIGS. 2 and 3) may optionally be produced by machining or during the compression molding process by which the composite nail is formed. Forming connection detail 32 by compression molding may be advantageous in terms of cost reduction.

FIG. 3 also illustrates the proximal end 12 of a composite material humeral nail 10. By way of example, the diameter of nail proximal region 13 may be in the range of about 10 to 12 mm for a nail shaft 38 having a diameter in the range of about 7 to 9 mm. The nail is connected to its insertion handle via a thread (not shown) at its proximal end.

FIGS. 2 and 3 also show screw holes 15, 17. Holes 15, 17 may be threaded, or optionally, they may be unthreaded. A radiopaque marker 36 is also shown at the proximal end of the nail.

Following nail implantation, a nail cap (not shown) may be introduced (e.g., screwed) into the threaded bore 30 at nail proximal end, in order to prevent bone growth into bore 30.

Pre-Drilled and Undrilled Bone-Supporting Component Configurations:

In FIGS. 1-3, bone nail 10 is shown with the passages for the bone screws pre-drilled during manufacture. In some embodiments of the invention, however, the bone nail, and also bone plates as described below, are supplied undrilled, or optionally, with a few screw holes or other passageways, for example, for initial anchoring. The reconfiguration guides facilitate formation during the implantation procedure of passages in the bone-supporting component for the fixation components or for otherwise shaping the bone-supporting component at the optimum locations and orientations for the particular fracture and patient anatomy. In addition, especially where small implants are involved, the option of not having unnecessary screw holes may contribute to the strength of the bone-supporting components.

Optionally, undrilled bone-supporting components include built-in reconfiguration guide areas e.g., indentations or depressions in the component surface that form blind grooves or slots, or blind holes or cutting lines. These built-in reconfiguration guides help prevent sliding of the drilling tool, particularly as a hole is started. Optionally, the implant is provided with several such reconfiguration guides located at positions in the implant that would not compromise the required implant biomechanical properties following drilling, for example, along the center line of the nail shaft or bone plate.

Exemplary built-in reconfiguration guides are described further below.

Exemplary Composite Materials:

In some embodiments of the invention, bone-supporting components and fixation components as described herein are formed of fiber reinforced polymer matrix composites. As an example, the composite material may be a fiber-reinforced polymer matrix, in which the polymer matrix is formed of polyetherketoneketone (PEKK), polyetheretherketone (PEEK), or other suitable polymers).

The reinforcing fibers may alternatively be formed, for example, of carbon or of a ceramic material, such as glass. The fibers may be of a diameter in the range of about 5 to about 10 microns for carbon fibers. Optionally, the carbon fibers are AS4, IM7, or IM10 Made by Hexcel Inc. Stamford Conn., U.S.A. Carbon fibers may optionally constitute about 60% to about 70% by volume of the composite.

Elongated components such as pegs, screws, and bone nails are optionally formed with a core in which the reinforcing fibers run longitudinally to resist mainly bending loads, and a sleeve enclosing the core, formed of one or more spirally wound layers for resisting mainly torsional loads. The core diameter is selected according the specific application of a particular implant.

Optionally, the sleeve is formed of two or more oppositely wound helical layers, for example, in which adjacent layers are wound at ±45 degrees relative to the core longitudinal axis. Winding over the core at ±45 degrees provides for maximal torsional stiffness (compared to other degrees of winding), as the fiber strain in those configurations is maximal per torsional angle of the nail.

Optionally, an additional outer layer is provided, as described below.

According to some embodiments, the core and the sleeve are constructed from pre-impregnated (prepreg) tapes of carbon fiber-reinforced polymer, preferably a thermoplastic polymer such as PEEK.

The prepreg tapes are available in the form of straight layers, during winding of each prepreg tape, the radius of curvature of the tape changes to conform to the winding diameter of the core. During winding, the filaments at the inner portion of the tape (i.e., with the smallest radius) become slightly folded. Thus, upon application of torsion, the filaments at the outer portion of the tape are stretched and can resist the torsional moment, while the inner filaments are not yet stretched. The inner filaments are only under tension upon exertion of higher torsional moments. In an embodiment of the invention, reducing the thickness (height) of the prepreg tape results in winding in which substantially more fibers are stretched earlier (i.e., upon application of lower torsional moment), and thus more efficient torsional stiffness is achieved. Optionally the thickness of the prepreg for winding is in the range of 0.05 to 0.2 mm, preferably 0.1 mm or less.

In an embodiment, the entire thickness of the winding (sleeve) remains substantially the same, while the thickness of each wound tape is decreased and the number of wound tapes is increased. Alternatively, decreasing the tape thickness, and thus improving the torsional stiffness, enables reducing the thickness of the winding sleeve on one hand, and increasing the diameter of the bone implant device longitudinal core (without increasing the diameter of the entire device), on the other hand. Therefore, this feature may contribute not only to the torsional stiffness of the device, but also to its bending performance.

The tapes intended for winding over a component core may also be manufactured as a helix, with the same (or approximate) radius of curvature of the required final winding radius.

Further exemplary details concerning the nature and use of prepreg tapes may be found in International Application PCT/IB2010/050225 which is incorporated herein by reference.

In some embodiments of the invention, at least some of the individual reinforcing fibers are at least partially coated. Such a coating can improve the strength of the implant, and/or may improve adherence of the polymer to the reinforcing fiber element. In an exemplary embodiment of the invention, a metal coating, for example, a titanium coating is used. In another exemplary embodiment of the invention, carbon with different crystalline properties (e.g., diamond, graphite, amorphous carbon, etc.), is used to coat the reinforcing fibers within the polymer matrix and/or the entire implant (for example, a diamond-like carbon coating). In an exemplary embodiment of the invention, the coating layer thickness is, for instance, less than 0.1 micron. In an embodiment, the coating totals in a relatively small amount of material, which does not adversely affect the implant properties under MR/CT imaging.

In some embodiments of the invention, different types of carbon fibers may be placed in different places in the implant to get advantage of different properties and/or different cost of the fibers. For example, fiber IM10 is stronger in tension 6,964 MPa compared to fiber AS4: 4,500 MPa but fiber IM10 is also less flexible having tensile module of 303 GPa relative to 231 GPa of fiber AS4. Accordingly in implant such as but not limited to nail, screw or plate, to get more flexibility for bending fiber type AS4 may be used in the core, and to get more torsional stiffness, IM10 will be used for the winding.

Typically, the polymer matrix is the weakest element in the composite. Optionally, the matrix may therefore include chopped fibers of carbon or other reinforcing material, which may improve bending performance. Optionally, the chopped fibers have different orientations in the matrix. Optionally, the chopped fibers are of various lengths within a range of about 0.1 to about 3 mm, and may constitute between about 1% and about 10% of the composite volume. The chopped fibers may be embedded into the prepreg tape, during manufacturing of the prepreg.

Alternatively chopped fibers may be added between the layers of the prepreg. Optionally, polymer material may be removed from the prepreg tape by heat and pressure.

Prepreg tapes are normally available in thickness not smaller than 0.2 mm. When calculating the strain required to initiate tension in the filaments at the inner portion of a tape with thickness of 0.2 mm which is helically wound (at 45 degrees) over a longitudinal core having a diameter of 8.5 mm, the strain is 2.3%. The strain at failure for a carbon fiber such as HEXCEL IM7 is about 1.9%. This means that for a tape of 0.2 mm thickness, the fibers in the outer surface of the tape are torn while the inner layer of the tape has not yet straightened and thus has not yet participated in the winding resistance to torsion.

Similar calculation for tape thicknesses of 0.1 mm and 0.05 mm results in strain values of 1.1% and 0.58%, respectively. In an embodiment of the invention, the ratio between the diameter of the device longitudinal core and the thickness of the helical tape is larger than 40, optionally larger than 70, optionally larger than 100 or 150. Strain at failure is the strain at which the fiber breaks. Using small thickness prepreg tape, and more windings, will share the stress along all the cross section area of the tape, and add torsional strength.

Figure 4:
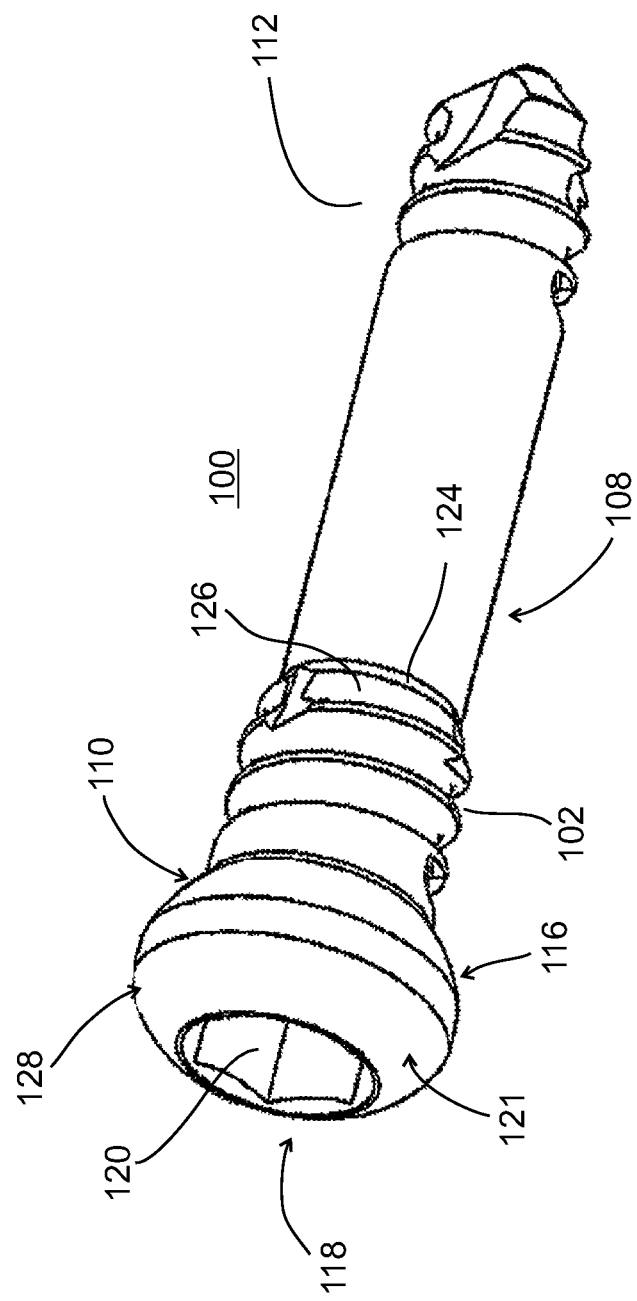
FIG. 4 is a side perspective view of a fixation component according to some embodiments of the present invention.

Exemplary Bone Screw and/or Peg Embodiments:

FIG. 4 is a generally side perspective view that illustrates an example of a fixation component 100 which may be used as a peg or screw to anchor a bone-supporting component such as a bone plate, or as a bone screw for a bone nail. One or more pegs or screws 100 are configured to extend through passages in a bone plate, and into holes drilled in the bone under the plate, as described below.

Bone screws and pegs are optionally formed of the same materials as the bone nails described in connection with FIGS. 1-3, and/or by a similar compression molding process, except that pegs do not need a sleeve to resist torsional forces.

Optionally, the composite material bone screw also comprises material that reduces the friction with the bone. Examples of such material are SiO2, PTFE, etc. The material may be added as powder, particles and/or other forms. Metal particles, such as titanium, may also be added to increase the device strength and to provide visualization under imaging (e.g., fluoroscopy).

Figure 5:
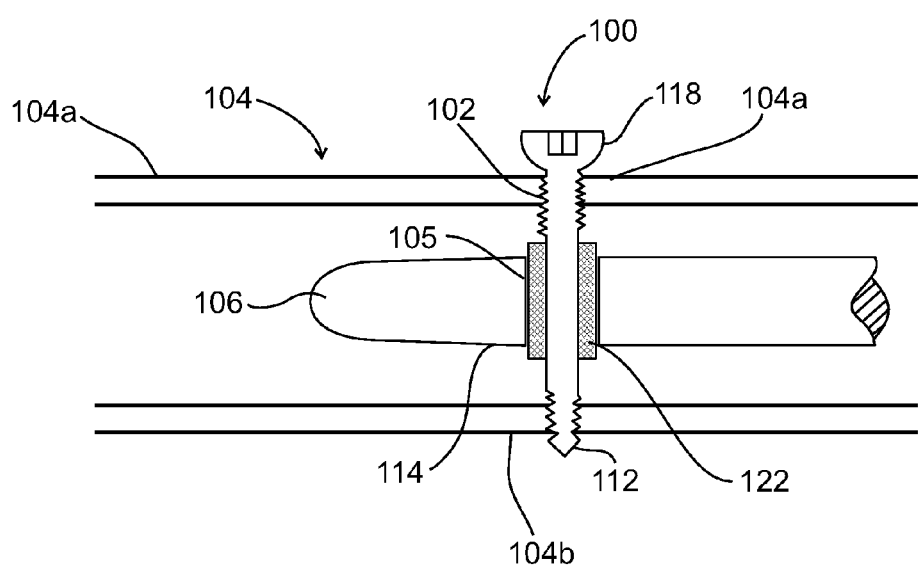
FIG. 5 is a cross-sectional view showing schematically a distal section of a bone nail anchored by a bone screw as illustrated in FIG. 4, according to some embodiments of the invention.

FIG. 5 illustrates in a schematic sectional view use of component 100 specifically as a bone screw for an intramedullary nail 106. Bone screw 100 is configured to attach to a bone 104 on a proximal side 104a, to extend through a passage 105 in a bone nail 106, and to attach to the bone at 104b on the side opposite to the bone nail. The passage 105 may be round as shown in FIGS. 1-3, or one or more passages may also be formed as longitudinal slots (no shown) to facilitate longitudinal positioning, for example, of a bone nail, which is then optionally firmly anchored by screws in round holes.

Referring still to FIGS. 4 and 5, fixation component 100 includes an attachment element, e.g., a threaded proximal end 102, configured to engage with the outer surface of a bone plate, or the proximal side 104a of a bone 104 in which a bone nail 106 has been implanted.

As further illustrated in FIGS. 4 and 5, the distal end 112 of body 108 is also optionally threaded. In the case of a bone screw, threads 112 engage with bone 104 on the distal side 114 of bone nail 106 at 104b (see FIG. 5) to immobilize bone nail 106 in the desired location and orientation, which are determined by the surgeon when the bone is drilled. Optionally, in the case of a bone peg, distal end 112 may be unthreaded. Optionally, threaded proximal end 102 may be replaced or supplemented by a locking element on body 108 that engages with the passages in the bone nail.

At the proximal end 116 of fixation component 100, a coupling element 118 is provided for engaging an insertion tool. Coupling element 118 is shown as a hexagonal recess 120 in a screw head 121, but any other suitable and desired shape, for example, Phillips head, axial crown, slotted, hexalobe, etc. may alternatively be provided. Recess 120 may alternatively be internally and/or externally threaded. As will be understood, the configuration of recess 120 optionally matches the connation end of the insertion tool.

Referring still to FIGS. 4 and 5, the head 121 and body 108 may be an integral structure formed, for example, by compression molding of the fiber-reinforced polymer composite material. Alternatively, head 121 may be formed a suitable biocompatible metal such as stainless steel or titanium into which composite body 108 is molded.

Friction forces associated with body loads can sometimes lead to abrasion at interfaces between the bone nail and the bone screw which produces polymer and/or fiber debris. To minimize or avoid this, the fixation components are advantageously constructed to reduce friction between the fixation components and the passages in the bone-supporting components. Alternatively or additionally, the components may be fabricated to have sufficient strength to resist the forces at the interface.

One way to accomplish this is shown in FIG. 5, in which one or more sleeves 122 are fitted into passage 105 in bone nail 106. Sleeve 122 may be used to change the type of friction in the interface from sliding friction to rolling friction. This arrangement is particularly, but not exclusively, suitable for bone nails and bone screws, where the bone screws are anchored at one or both ends in the bone.

Additionally, or in the case of pegs, alternatively, resilient locking elements may be provided. These are coupled to the body, and configured to engage the passages only over a small area and thereby reduce wear and creation of debris.

Locking elements may take various forms, among which are spring elements coupled to the fixation component, and constructed and configured to expand radially to engage with the passage upon insertion.

One suitable arrangement is shown in FIG. 4. As illustrated, at the distal end of proximal threaded portion 102, there is a groove 124 in which a resilient split ring element 126 is positioned. This can be formed of any suitably strong and resilient material, including but not limited to a reinforced polymer composite material. As will be understood, split ring 126 is compressed in the passage in the bone-supporting component so that the restoring force anchors the fixation component.

Figure 6A:
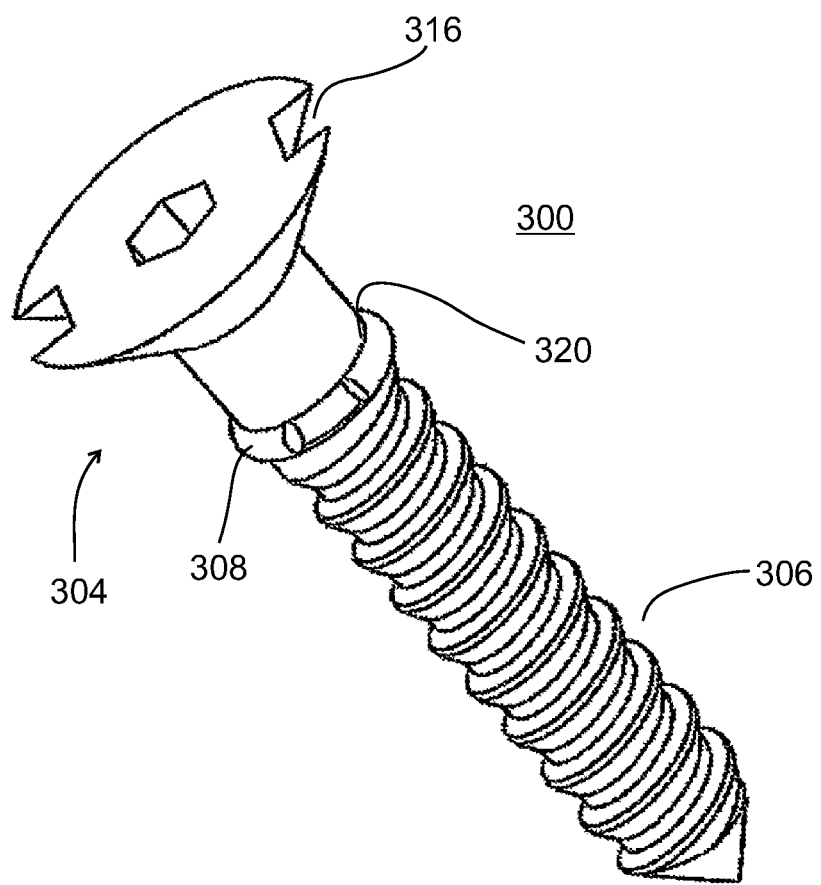
FIG. 6A is a generally side perspective view of a fixation component with a portion that is oversized relative to a passage in a bone supporting component.

Another suitable arrangement is shown in FIG. 6A. Here, fixation component 300 is free of threads in its proximal region 304 and is threaded only at its distal region 306. Locking element 308, also in the form of a resilient split ring, is fitted in a groove 320 at the proximal end of the threaded portion 306.

Figure 6B:
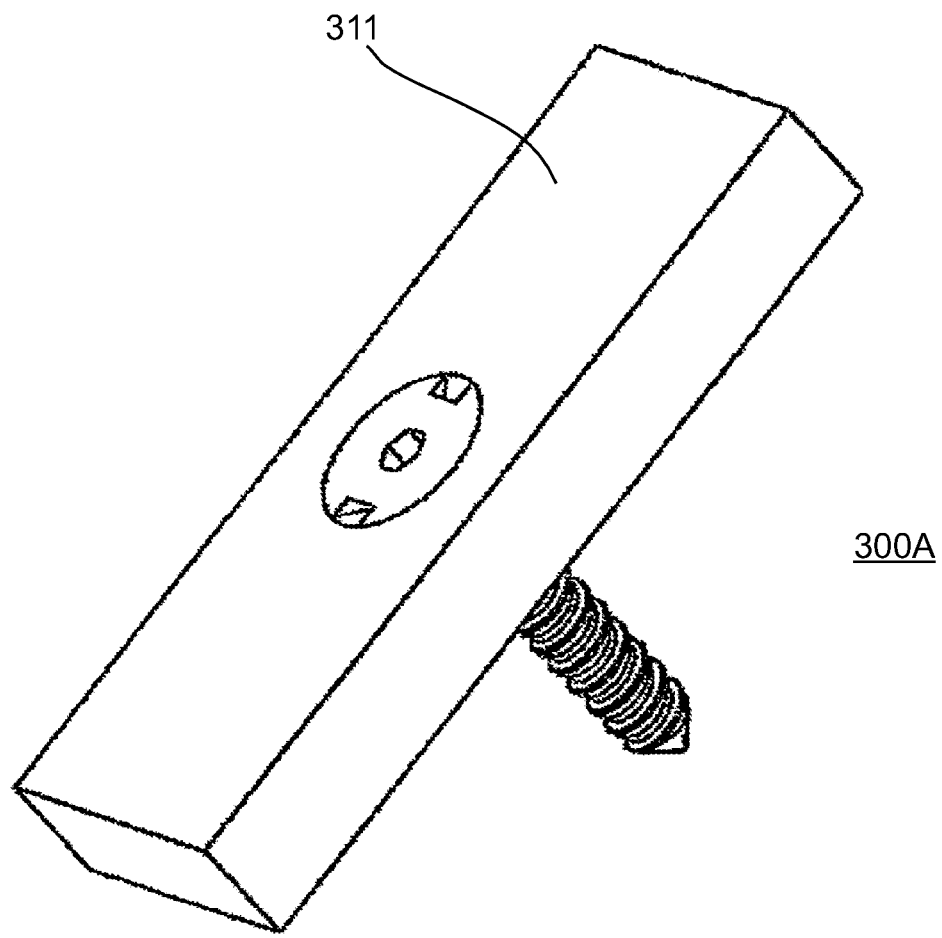
FIG. 6B is a perspective view showing schematically the component of FIG. 6A installed in a bone-supporting component.
Figure 6C:
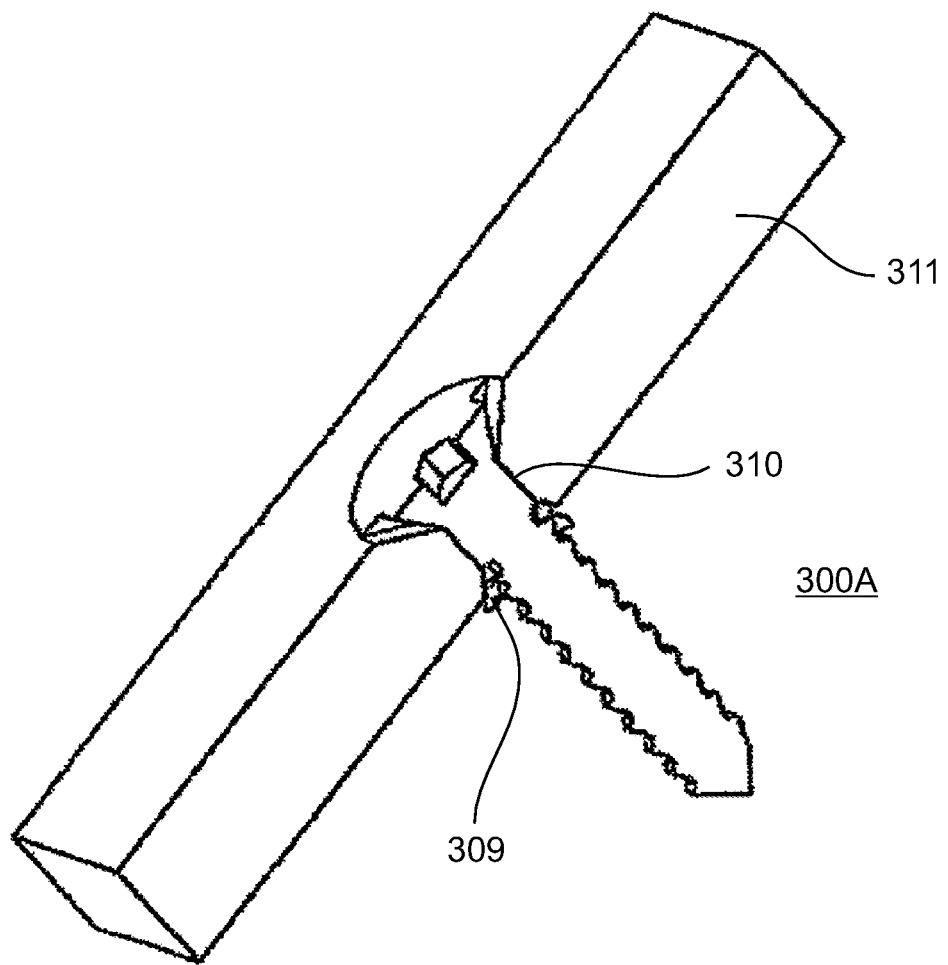
FIG. 6C is a cut-away view of FIG. 6B.
Figure 6D:
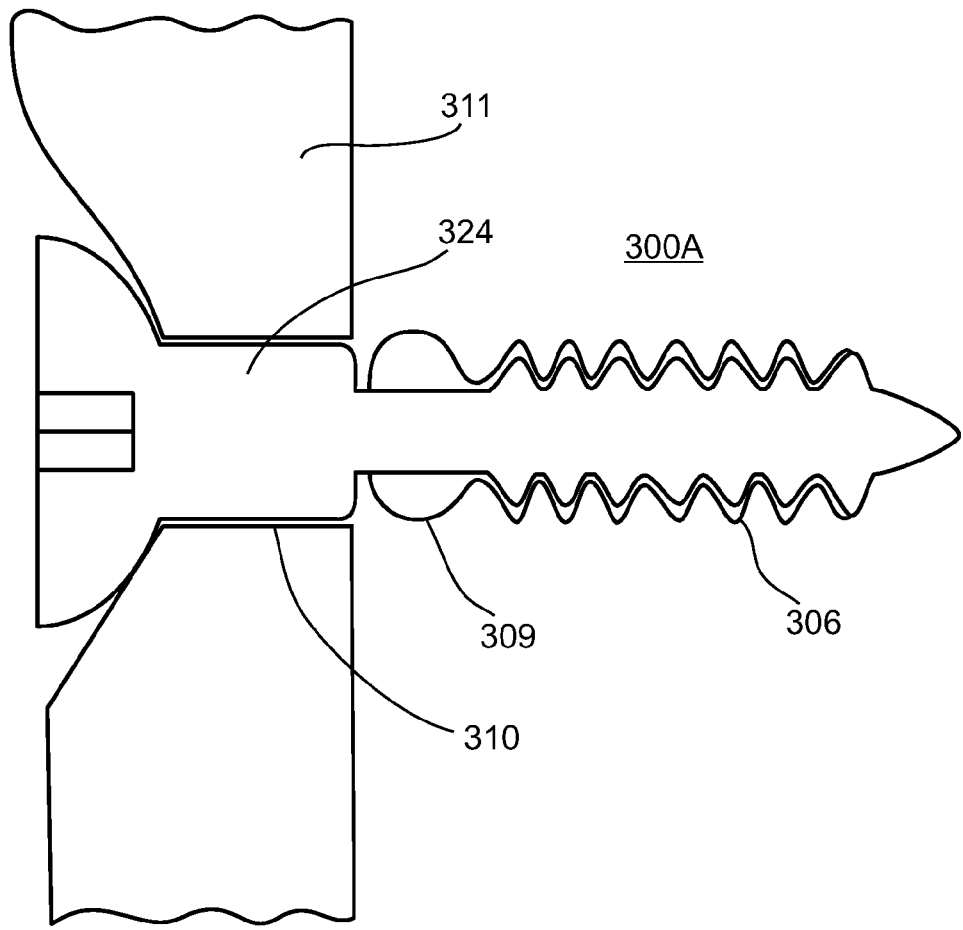
FIG. 6D is an enlarged side-sectional view of the fixation component of FIG. 6C.

Another locking arrangement for use with pegs and/or bone screws is illustrated in FIGS. 6B-6D. In contrast to fixation components 100 and 300 shown in FIGS. 4 and 6A, fixation component 300A includes an enlarged thread 309 installed in bone-supporting component schematically illustrated at 311. FIG. 6C is a cut-away view of FIG. 6B, and FIG. 6D is an enlarged sectional view of FIG. 6C.

As illustrated in FIG. 6D, a thread 309 at the proximal end of threaded portion 306 is made oversize relative to the other threads and relative to the passage 310 in bone-supporting components 311 so that the composite material of the enlarged thread(s) must compress as it is installed through passage 310.

In some other embodiments, a bone screw may be metal-coated, or coated with a polymer such as a bioresorbable or biodegradable material to reduce wear during implantation, or for other purposes, as in the case of bone nails, and employing the same coating materials.

For example, coating may be provided to strengthen and/or improve the hardness of the implant. In an exemplary embodiment of the invention, the screw is coated with one of the following materials: titanium nitride (TiN) [E. Lugscheider, S. Barwulf, M. Riester, H. Hilgers, Magnetron sputtered titanium nitride thin films on thermoplastic polymers, Surface and Coatings Technology 116-119 (1999) 1172-1178; and H. S. Kim, H. J. Jung Kim, Detorque force of TiN-coated abutment screw with various coating thickness after repeated closing and opening, J Korean Acad Prosthodont: Volume 45, Number 6, 2007], titanium aluminum nitride (Ti—Al—N), diamond like carbon (DLC), ceramic material or other suitable material. In an embodiment of the invention, the coating is performed using physical vapor deposition (PVD) technique [Rahamathunnisa Muhammad Azam, Mari Tanttari, Tommi Kääriäinen, David Cameron, Coatings on Composites, Lappeenranta University of Technology, Faculty of Technology, Department of Mechanical Engineering, Research Report No. 74, ISBN 978-952-214-504-8, ISSN 1459-2932, Mikkeli 2007], optionally following preparation of the surface of the implant (e.g., grid blast, bombardment of argon ionized ions, etc.). In an embodiment of the invention, more than one material is used for the coating, for example a first coating layer of titanium and a second coating layer of ceramic material. In an exemplary embodiment of the invention, the thickness of the coating layer is in the range of a few microns. In an embodiment of the invention, coating of the bone implant is conducted in order to improve the implant osteo-conductive and/or osteo-inductive properties, thus to enhance implant ability to integrate in the bone and to support bone ingrowth. Such coating may be, for example, porous titanium or hydroxyapatite (HA). In an embodiment, the coating is added using a vacuum plasma spray (VPS) technique, optionally following preparation of the surface of the implant [as described, for example, in S. W. Ha, A. Gisep, J. Mayer, E. Wintermantel, H. Gruner, M. Wieland, Topographical characterization and microstructural interface analysis of vacuum-plasma-sprayed titanium and hydroxyapatite coatings on carbon fibre-reinforced poly (etheretherketone), Journal of Materials Science Materials In Medicine 8 (1997) 891-896; and S. Beauvais, O. Decaux, Plasma Sprayed Biocompatible Coatings on PEEK Implants].

With any of the spring locking arrangements described, and the arrangement of FIGS. 6A-6D, a mechanism is optionally provided for removing the fixation component if necessary. One suitable way is shown in FIG. 6A. Here, head 314 includes a plurality of notches 316 at the proximal end 318 of head 314 in which a removal tool may be engaged.

Figure 7A:
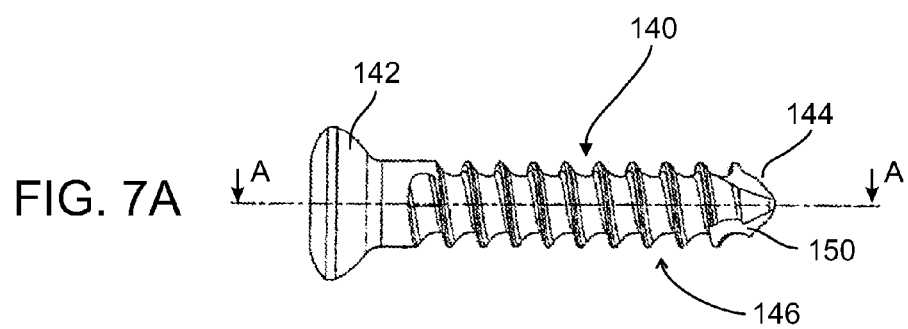
Figure 7B:
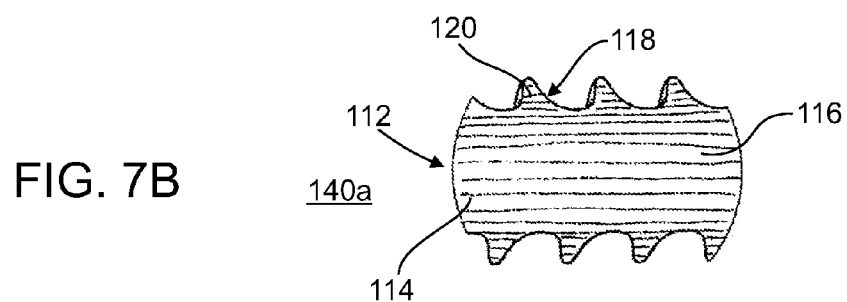
Figure 7C:
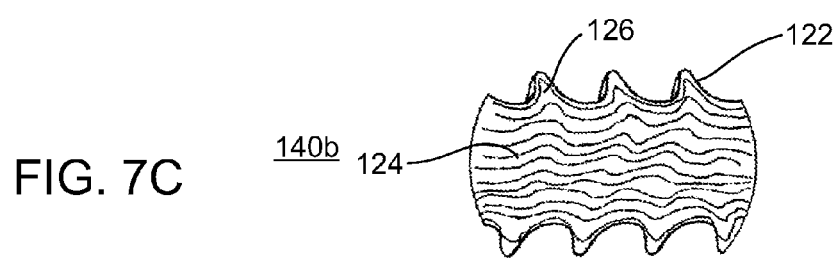
Figure 7D:
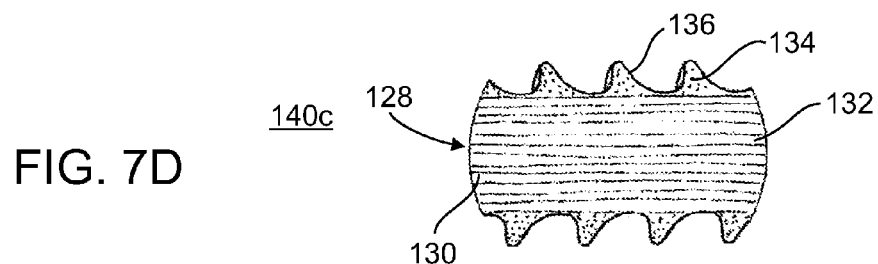

FIGS. 7A-7D illustrate other exemplary embodiments of composite material bone screws. FIG. 7A shows a side elevation of a bone screw 140; FIG. 7B is a proximal end perspective view of FIG. 7A. FIGS. 7C-7D are schematic sectional views of the distal region 141 of bone screw 140.

Screw 140 comprises a head 142 at its proximal end, with connection means to engage with insertion/removal instruments (not shown). Connection means may be of any conventional shape, for example, an internally or externally threaded hexagon, Phillips head, axial crown, slotted, hexalobe, etc. The hexalobe configuration may be advantageous in resisting damage due to application of torsion by the insertion device.

The distal end 144 of screw 140 is tapered 144 and comprises cutting edges 150 to provide for self-tapping. The screw 140 also comprises thread 146 at a desired pitch along its length. The screw 140 is made, for example, from a fiber reinforced polymer, a material that is radiolucent under imaging such as fluoroscopy, as described in more detail below.

FIG. 7B illustrates a screw that comprises a core 112 made of relatively straight elongated fibers 114 within polymer matrix 116. In an exemplary embodiment of the invention, the screw is manufacture in two main steps—compression molding, during which a composite material rod is generated, and machining, during which the screw thread 118 is created. As can be seen in the figure, the fibers in the thread 120 are cut due to the machining process. Having only straight longitudinal reinforcing filaments at its core contributes to the screw bending properties. On the other hand, the short, non-sequential fibers at the screw thread compromise the thread resistance to shear forces. Therefore, this combination of screw features may be beneficial for screw applications that mainly require bending strength, such as screw intended to interlock an intramedullary nail.

FIG. 7C illustrates a screw that is entirely (i.e., including its thread 122) produced by compression molding. In some embodiments, a fiber reinforced polymer material, for example in the form a rod, is pressed (under heat and pressure) into a mold that forces the material to fold at and into designated areas (e.g., the thread areas), thus creating a thread 122. This optionally results in a composite material screw that comprises folds of the elongate fibers 124 and fibers 126. This screw configuration may be beneficial for applications that require high pullout strength forces but less bending strength, for example, screws used with bone plates, as described below.

FIG. 7D illustrates a screw that comprises a core 128 made of relatively straight elongated fibers 130 within polymer matrix 132, produced, for example, by compression molding. Over core 128, a helically winding 134 in one direction of fiber reinforced polymer is added, optionally in a manner in which winding pitch is equivalent with the desired screw pitch. Optionally, the helical winding 134 is made of prepreg tape/s of fiber-reinforced polymer, so that tape width is compatible with the desired width of the screw teeth. Optionally, the screw is further machined to produce the desired configuration of the thread teeth 136. Optionally, a profile winding 134, for example that has a relatively triangular cross section is helically wound around the core 128. Such a thread may be advantageous, for instance, upon threading of the screw into the cortical bone.

Optionally, in embodiments illustrated in FIG. 7D, two helically wound tapes may be employed. Optionally, one is wound clockwise and the other counterclockwise for example, at ±45 degrees relative to the longitudinal axis of the core.

When assessing the above-described screw designs, it is expected that a screw which comprises a core of straight longitudinal reinforcing filaments and machined thread, may be beneficial for applications requiring mainly bending strength, such as for screws intended to lock intramedullary nails to the bone.

The screw produced by axially pressing comprises folded reinforcing fibers in its core, and thus may have lower bending performance, however, the resistance of its thread to shear forces may be enhanced (as the reinforcing fibers at the thread are not damaged during manufacturing, and therefore may be preferred when high pullout strength is required). This screw design may be preferred, for example, for screws intended to lock plates to the bone (where screw pullout from the bone is the failure mode).

The screw thread created with profile winding is expected to be advantageous during threading of the screw into the cortical bone, as the orientation of the fibers in the thread component in this screw design matches the thread pitch, and thus provides for a strengthened thread with potential for less wear upon screw threading.

Reference is now made to FIGS. 8A-8C, which schematically illustrate a bone screw 160 having a separate distal end component 162 made of a material that is harder than body 164 of the screw 160 and optionally harder than cortical bone. FIG. 8A illustrates assembled bone screw 160, while FIGS. 8B and 8C illustrate the bone screw components 164 and 162, respectively, prior to their assembly.

The distal end component 162 may optionally be made of ceramic material, such as zirconia which also does not interfere during MRI, or a metal such as titanium. Screw body 164 is formed from fiber-reinforced composite material as described above. Optionally, the body is formed using the distal end as a mould.

Enhanced distal-end hardness may be useful to improve self-tapping capability, and/or to reduce the possibility of damage to the distal end during screw introduction into the bone.

As shown in FIGS. 8B and 8C, the interface 166 between the distal end component 162 and the screw body 164 is optionally configured to provide for torsion transferring while preventing the distal end component 162 from tearing off the screw body 164. Interface 166 is shown as hexagonal, but optionally, other non-circular geometric shapes may be employed.

Optionally or additionally, distal end component 162 includes undercut portion in the internal side of this bore to help assure firm connection of the distal end component 162 to the screw body 164. By melting the composite into the undercut, 162 will be axially locked into 164.

Figure 9:
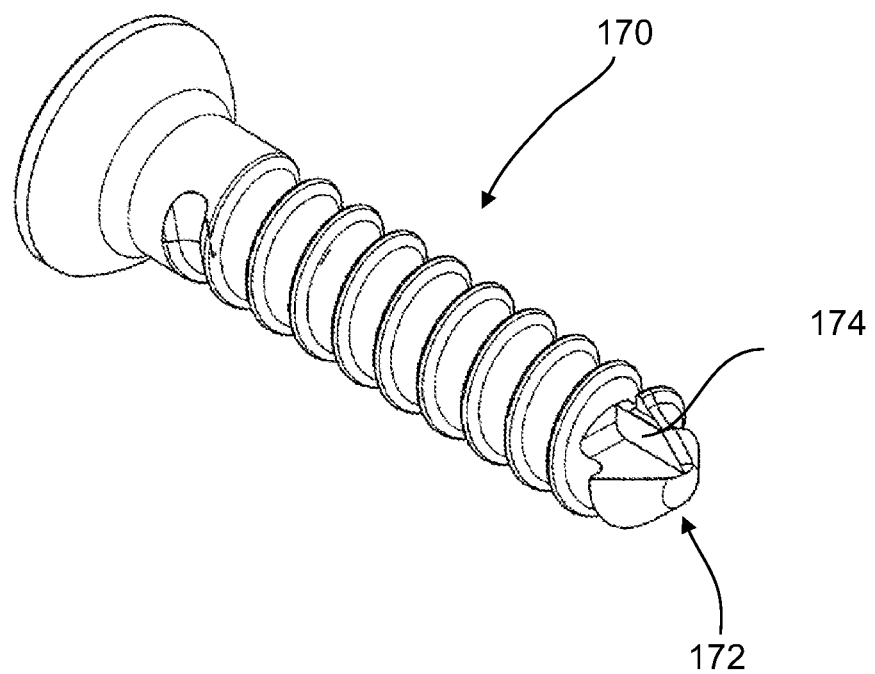

FIG. 9 illustrates another embodiment of a bone screw 170 in which a distal end 172 exhibits enhanced hardness and self-tapping capability. Here, distal end 172 includes one or more inserts, one of which is shown at 174, that serve as the thread-cutting tool. Insert(s) 174 are made of material with higher hardness than that of the rest of the screw and than that of the cortical bone, for example ceramic or metal material. Connection of the insert to the screw is achieved using adhesion means and/or (optionally) a non-circular geometric connection that prevents tear-off of the insert from the screw.

Figure 10A:
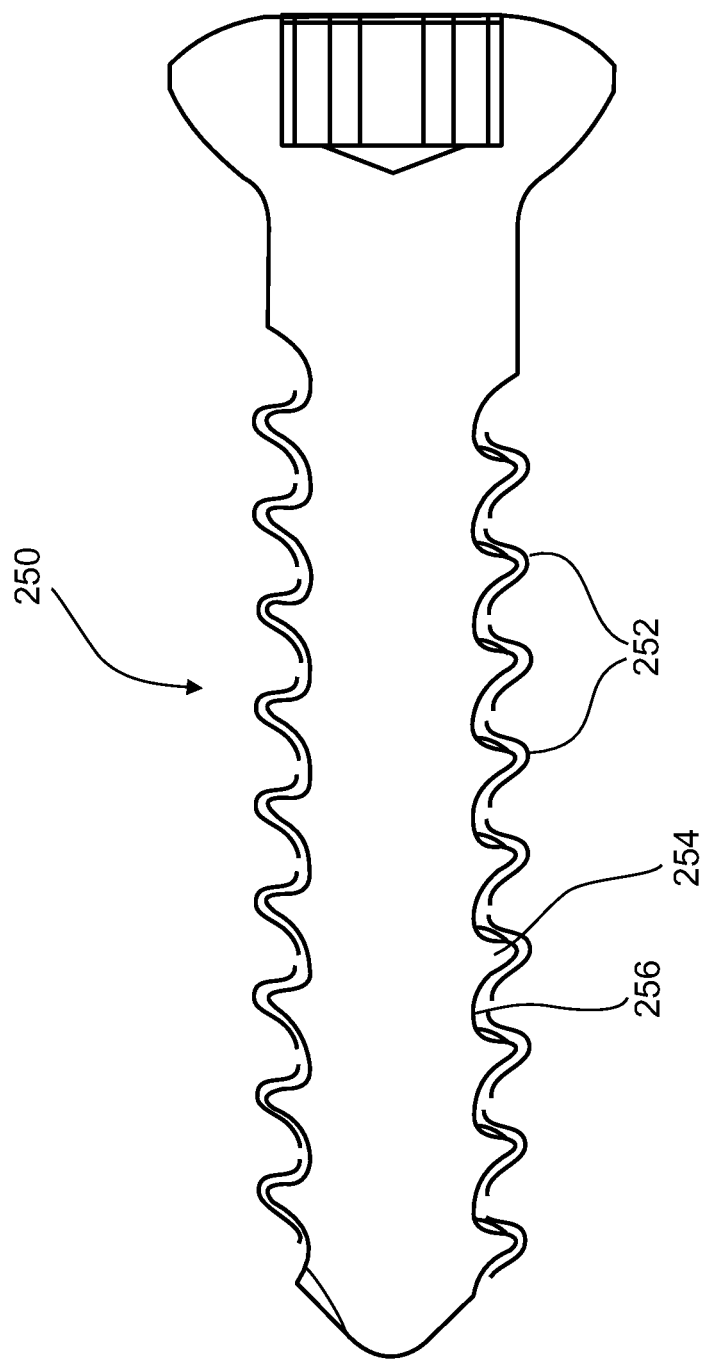
FIGS. 10A-10D illustrates composite material bone screws having an external coating according to some embodiments of the invention.

FIGS. 10A-10D schematically illustrate other embodiments of a composite material screw exhibiting enhanced hardness. FIG. 10A is a schematic longitudinal cross-section of one such embodiment. Optionally, as shown in FIG. 10A, in cases where the coating material has a limited elongation before break, the coating over screw 250 is not continuous, but rather limited to the crown portions of threaded teeth 254, i.e., the thread portions that penetrate into the bone, while the root areas 256 between the teeth are not coated.

Discontinuous coating may be also applicable to other portions of a composite implant.

Figure 10D:
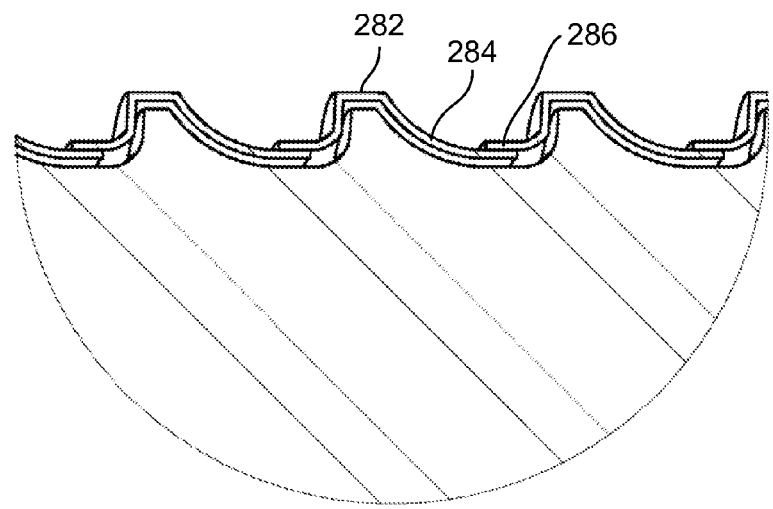
Figure 10C:
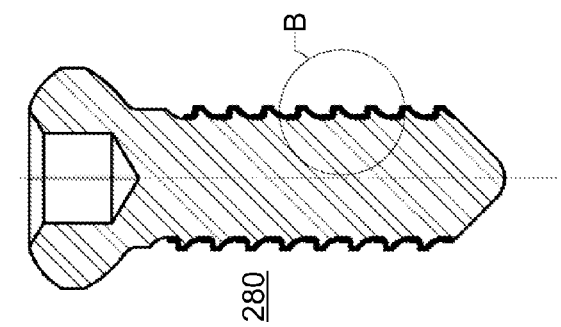
Figure 10B:
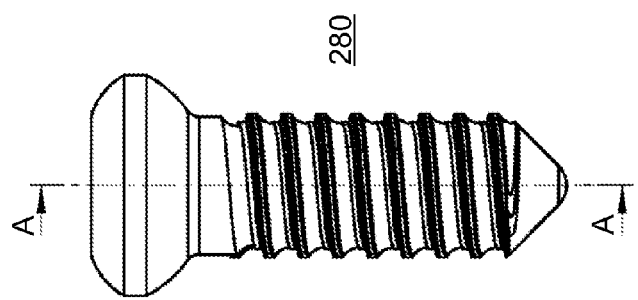

FIG. 10B is a side elevation view of a screw that is a variation of the screw of FIG. 10A, generally labeled 280. FIG. 10C is a cross-section of a FIG. 10B taken along line A-A. FIG. 10D is an enlarged view of area B in FIG. 10C.

Screw 280 differs from screw 250 in that the entire length of screw 280 is covered by a coating 282. This may be desirable to increase the hardness of all the screw parts that may be in contact with bone. Optionally, the coatings of root portions 284 between the threads are overlapped, as indicated at 286, for example, by extensions of the coatings of the adjacent crown portions of the thread, or by overlapping the tape as it is wound over the threads. Optionally after winding the metal tape with overlap 286, the internal and external side of the overlap may be welded at least partially along the spiral overlap. Optionally the tape is welded using a pulsed laser or a continuous laser beam.

Figure 11:
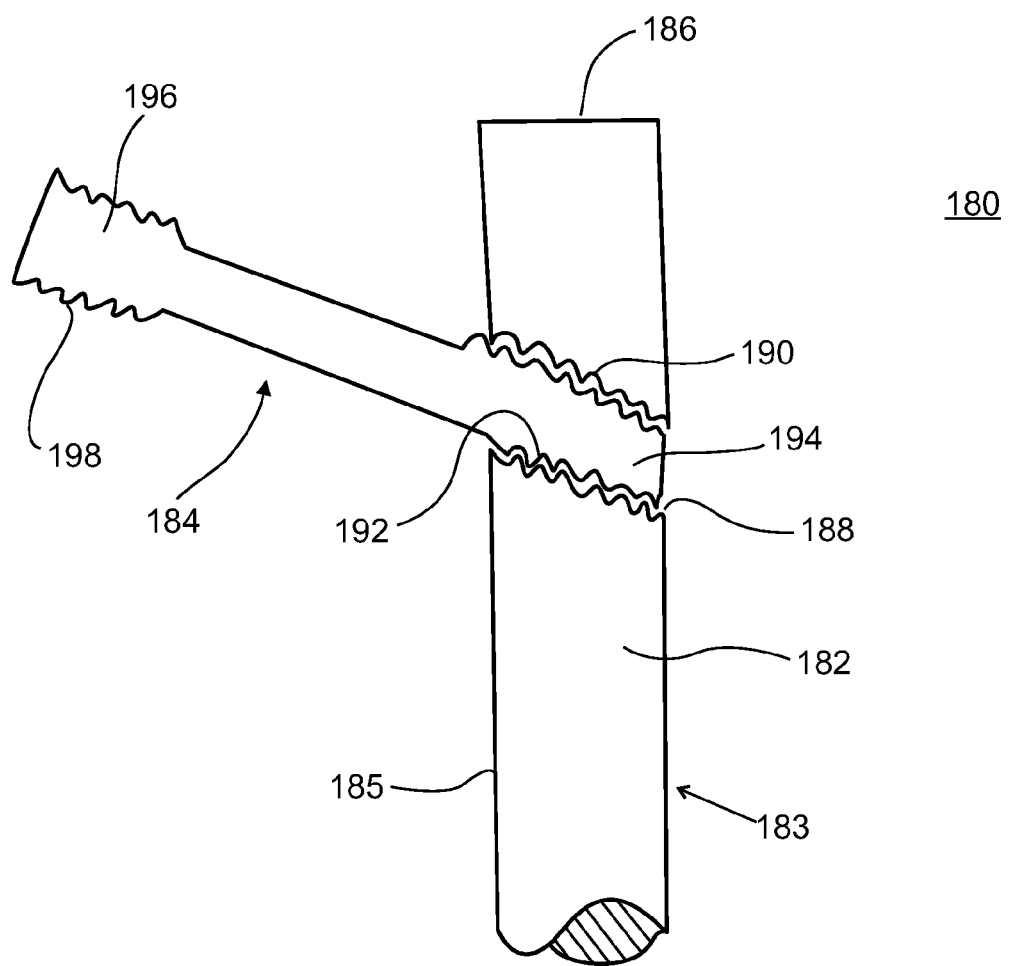
FIG. 11, FIGS. 12A-12B and FIGS. 13A-13B illustrate different composite material proximal femur nail and leg screw configurations, in accordance with some embodiments of the invention.

FIG. 11 schematically illustrates a portion of a proximal femur implant 180, including the stem 182 of an intramedullary femoral nail 183, and a leg screw 184. The nail 182 is inserted into the medullary canal of the femoral bone, and the leg screw 184 is introduced, via a passage 188 in the nail 182, into the femoral neck and head of the bone. The proximal femur implant 180 is intended to treat or help prevent fractures in the proximal area of a femoral bone. The components of implant 180 are made of a fiber reinforced polymer composite material, optionally including other materials, such as metal (for example, titanium), and/or are coated with a non-composite material as described above.

At its proximal end 186, nail 183 comprises a connector, e.g., an internally threaded portion, configured to engage with an insertion tool, and, after insertion, to receive an end cap to seal the proximal end and prevent bone ingrowth.

Along its distal region 185, nail stem 182 may be tapered. In its proximal region, in addition to passage 188 for bone screw 194, there may be provided one or more additional passages for additional bone screws or bone pins. These may be oriented transversely relative to nail stem 182, and function to lock the nail to the bone and/or to provide additional rotational stability.

Passage 188 is threaded, along at least part of its length, shown at 190, which is configured to engage a complementary thread 192 at the proximal end 194 of the leg screw 184. The distal end 196 of the leg screw 184, which is inserted into the femoral head, is threaded at 198, to allow firm fixation within the cancellous femoral head. The thread 198 may be self-tapping. Optionally, the distal thread 198 and the proximal thread 192 of the leg screw 184 have the same pitch. The leg screw 184 may be cannulated (not shown in the figure), to allow its introduction into the bone over a guide wire. At proximal end 194, the leg screw 184 comprises a connector (not shown in the figure), configured to engage with the screw insertion tool. Optionally thread 198 may be coated with metal.

The different threads of the implant 180 may be produced using various processes, such as machining, axial pressing, and/or profile winding, as in previously described embodiments.

FIGS. 12A and 12B are side elevation and longitudinal cross-section views, respectively, representative of some embodiments of a composite material proximal femur implant, generally illustrated at 200. Implant 200 comprises an intramedullary femoral nail 202, and leg screw 204 which is inserted into the femoral neck and head through a passage 212. Implant 200 also includes a sleeve 206, located in passage 212 between nail 202 and leg screw 204.

At its proximal end 208, nail 202 includes a coupling element 210 element similar to the one described in FIG. 3 configured to engage an insertion tool. In some embodiments, proximal end 208 is internally threaded to receive an end nail cap as in the embodiments described in connection with FIG. 11.

Along its distal region, nail 202 may be tapered as in FIG. 11. Passage 212, at least along part of its length optionally includes a threaded portion 214 configured to engage a matching thread on the outer surface of the sleeve 206. Sleeve 206 enables sliding of the leg screw 204 in relation to the nail 202. This arrangement is intended to prevent a phenomenon called cut-out, referring to the subsidence of the femoral head and protrusion of the leg screw out of the femoral head.

The sliding of the leg screw 204 in sleeve may optionally be limited, for instance by a tool inserted from nail proximal end 208 and engages a locking element 216 that limits the leg screw 204 movement to a pre-defined travel. Locking screw 216 is passing through a window in sleeve 206, and enters a slot in the leg screw 204. The length of the slot limits the sliding.

Reference is now made to FIGS. 13A and 13B, which are side elevation and longitudinal cross-sectional views, respectively, of a composite material proximal femur implant 230. The implant 230 comprises an intramedullary femoral nail 232, a leg screw 234 and a sleeve 236, located between the nail 232 and the leg screw 234. Implant 230 is generally similar to implant 200 described in connection with FIGS. 12A and 12B, and the details will not be repeated in the interest of brevity.

Implant 230 differs from implant 200 mainly in that sleeve 236 is longer than nail passage 242. Optionally, the sleeve 236 protrudes from both ends of the nail passage 242. Having a longer sleeve may be advantageous in some embodiments, as the leg screw 234 experiences lower bending moment in this configuration.

Various embodiments of implants 180, 200, and 230 share several features. For example, one or more of the following features may be provided in the implants described herein or in other composite implants:

a) leg screws 184, 204, and 234 may be cannulated, to allow introduction into the bone over a guide wire;

b) at their respective proximal ends, the leg screws include connectors configured to engage with screw insertion tools;

c) implants 180, 200, and 230 are made of a composite material, as detailed above, and may optionally include metal components and/or may be partially or completely coated with metal or other non-composite material;

d) sleeves 216 and 236 may be made of metal such as titanium, ceramic material, or composite material with reinforcing fibers oriented and/or configured to carry the load exerted on the bone, as described in connection with FIGS. 12A and 12B.

e) nails 183, 202, and 232 may include additional passages (not shown), configured to accept anti-rotational pins. These may, for example, be of smaller diameter than the passages for the bone screws, and may be located parallel to and above the respective leg screw passages.

f) the longitudinal stem of the nail may be expanded following its introduction into the medullary bone canal, in a manner that allows abutment of at least part of nail outer surface to the inner wall of the bone canal for example, in a similar manner to that described in WO 0154598 (U.S. Pat. No. 6,127,597).

g) the implants may include at least one radiopaque marker e.g., a tantalum thread, ring, dot, pin, etc. (not shown), as discussed hereinafter. Optionally, a passageway, for example, for a guide wire is made or includes a radiolucent material, for example, in the form of a wire or hollow tube.

Figure 12:
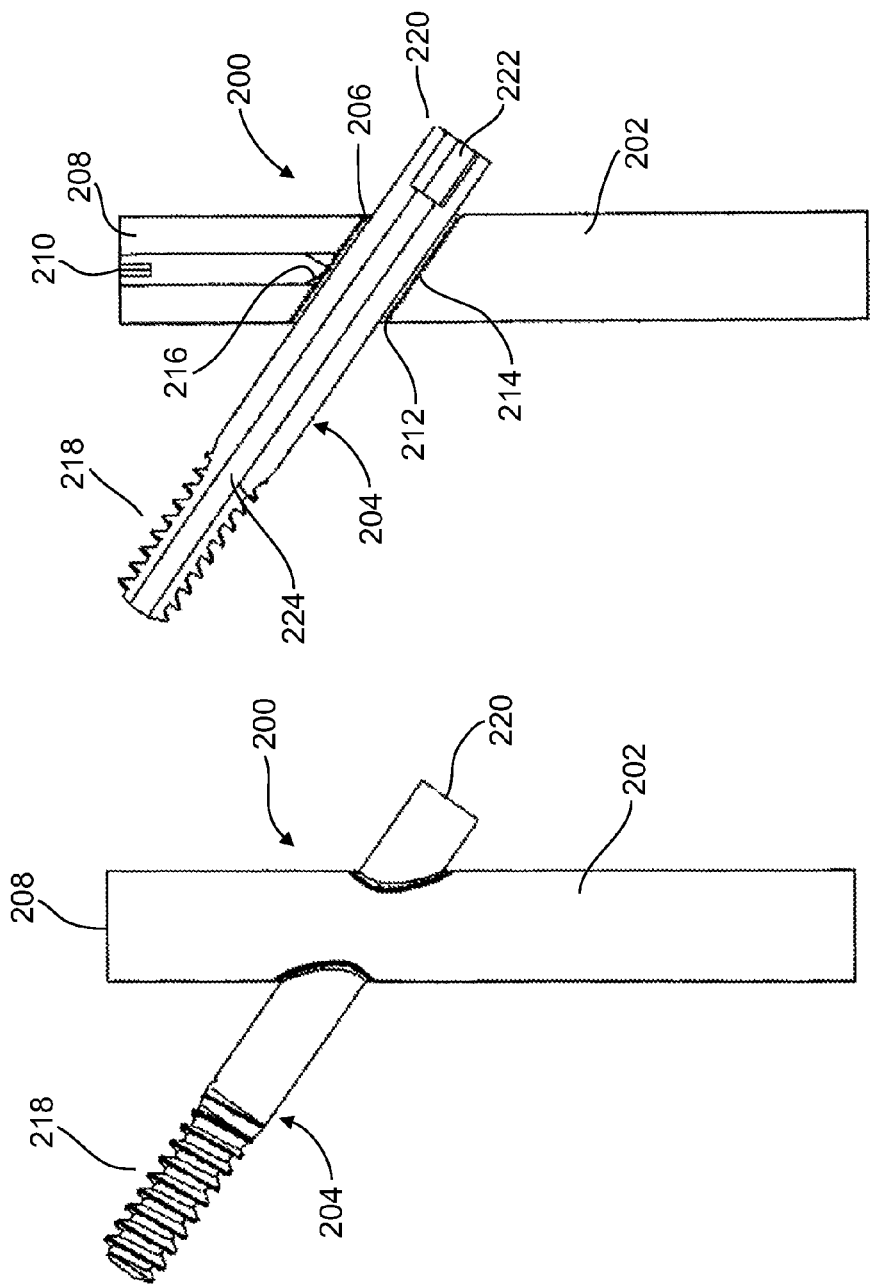
Figure 13:
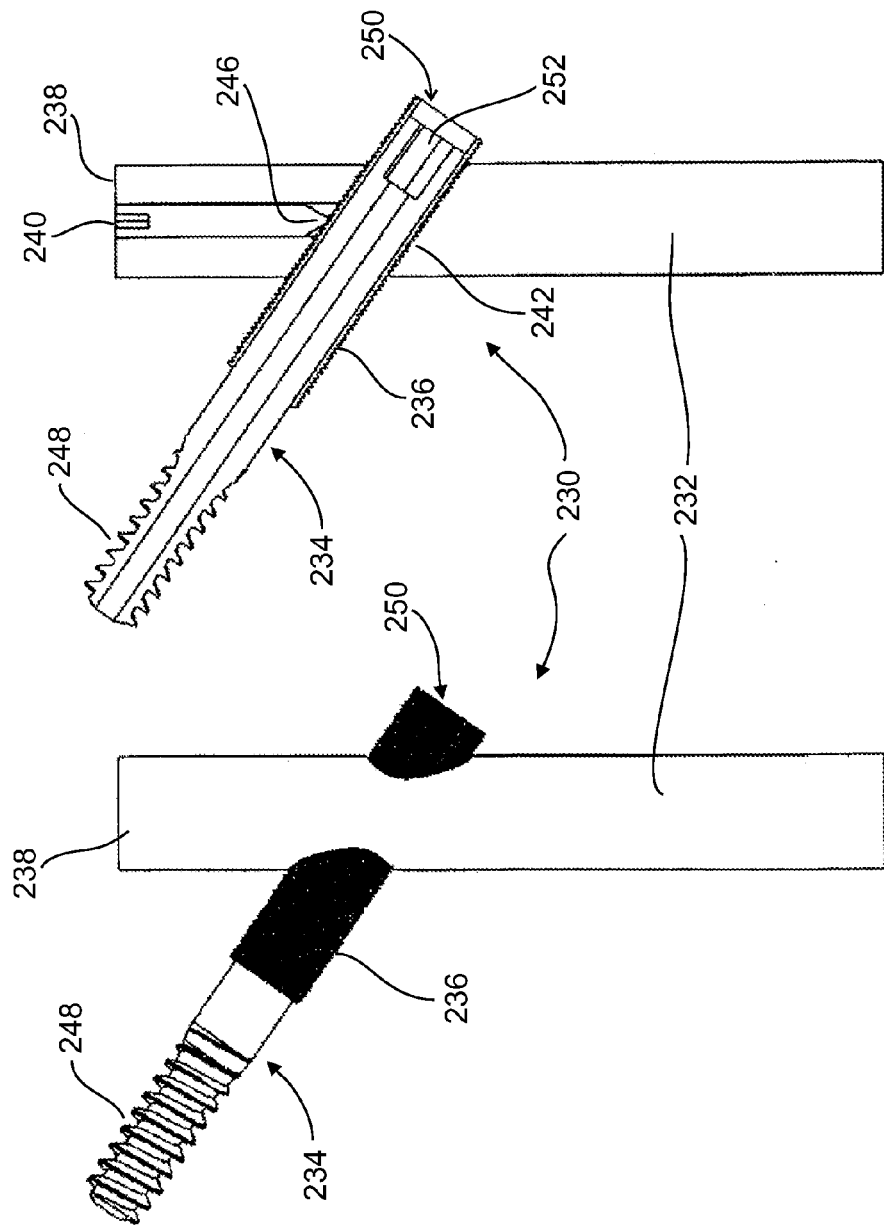
Figure 14:
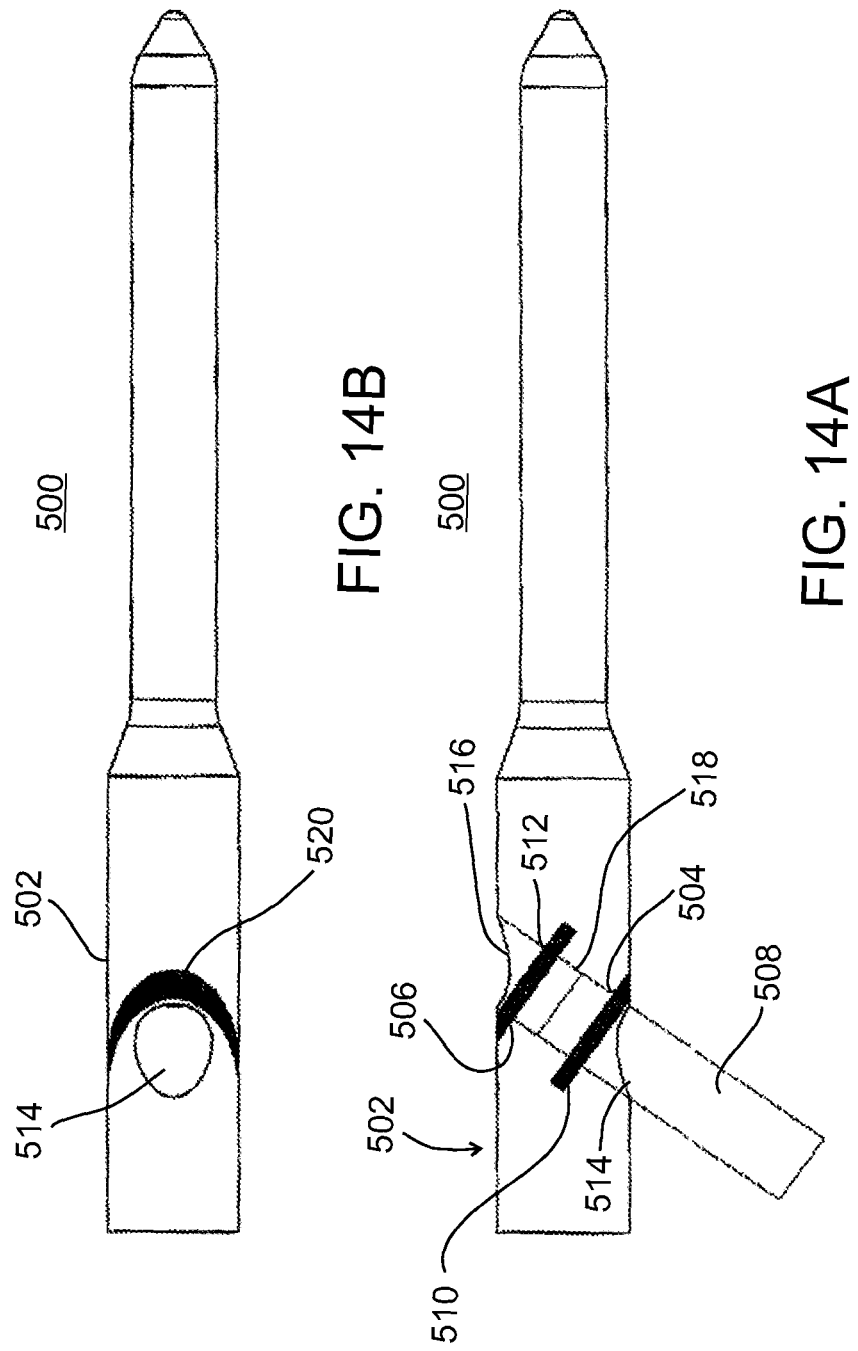
FIG. 14A is a side elevation view of a bone nail that provides reinforcement at the interface with a bone screw.
FIG. 14B shows a side view of FIG. 14A, rotated 90 degrees.

FIGS. 14A and B illustrate a possible solution to a reinforcement problem that may exist due to high local stresses causing deformation for example, in the stem of a proximal femur nail in applications such as illustrated in FIGS. 11-13. FIG. 14A shows a sectional view of the proximal end 502 of nail 500. FIG. 14B shows a side view of FIG. 14A, i.e., rotated 90 degrees.

Stress can be especially severe in the edges of the leg screw hole of the stem, due to the high moment applied by the leg screw on the hole. Orienting the reinforcing fibers longitudinally or helically does not eliminate the deformation.

According to some embodiments of the invention the problem is alleviated by orienting the reinforcing fibers in a way that converts the compression reaction into tension of the fibers in the stem. FIG. 14A shows the points of greatest stress 504 and 506 due to bending of bone screw 508. At these locations, the reinforcing elements 510 and 512 are configured in a U-shape and an opposed U-shape at ends 514 and 516, respectively, of passage 518. Reinforcing elements 510 and 512 are oriented preferably in planes perpendicular to the main axis of the screw 508, where leg screw 508 bears most forcefully in passage 518. In this way, the compression reaction due to the leg screw 508 load is converted into tension of the fibers.

Figure 15:
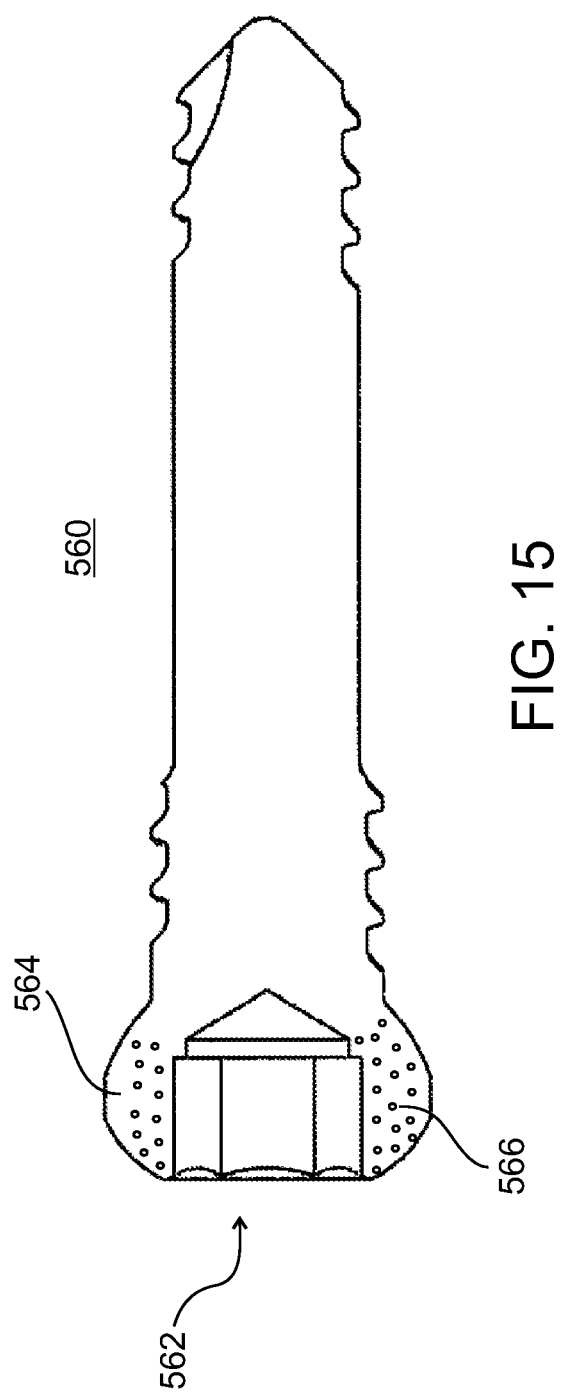
FIG. 15 is a side view, including a portion in schematic partial section, showing the orientation of reinforcing fibers in the head of a fixation component formed of a fiber-reinforced polymer composite according to some embodiments of the invention.

FIG. 15 is a schematic side view of a fixation component 560 that illustrates a solution to another reinforcement problem that may exist due torsional stresses of a fiber-reinforced head 562 of a bone screw. The torsional forces resulting during insertion are supported by adding a ring 564 of circumferentially or spirally wound reinforcing fibers 566.

FIG. 16A is a side elevation view, and FIGS. 16B and 16C are longitudinal cross-sectional views taken along line A-A in FIG. 16A, that illustrate two options for radiopaque marking of a radiolucent fixation component such as a bone screw generally denoted at 440 in FIG. 16A. To provide for visualization of the screw under fluoroscopy during the implantation procedure, and/or post-operative follow-up, a metal wire 452 is incorporated into the screw along its longitudinal axis (see FIG. 16B). Optionally, the wire is made of tantalum.

Alternatively, as illustrated in FIG. 16C, two radiopaque wires or pins 454 and 456, are provided only at the proximal and distal ends, respectively, of screw 440. These, too, may optionally be formed of tantalum.

It is to be understood that other shapes, e.g., dots or rings, and different sizes, locations and materials may be applicable for marking the radiolucent bone screw.

It should be noted that if some of the reinforcing filaments of the bone implant are at least partially coated, adding a radiopaque marker to provide visualization of the radiolucent implant under fluoroscopy during insertion may not be necessary. It may be desirable, however, to limit the coating so that it does not interfere with post-operative visualization.

Figures 17A, 17B:
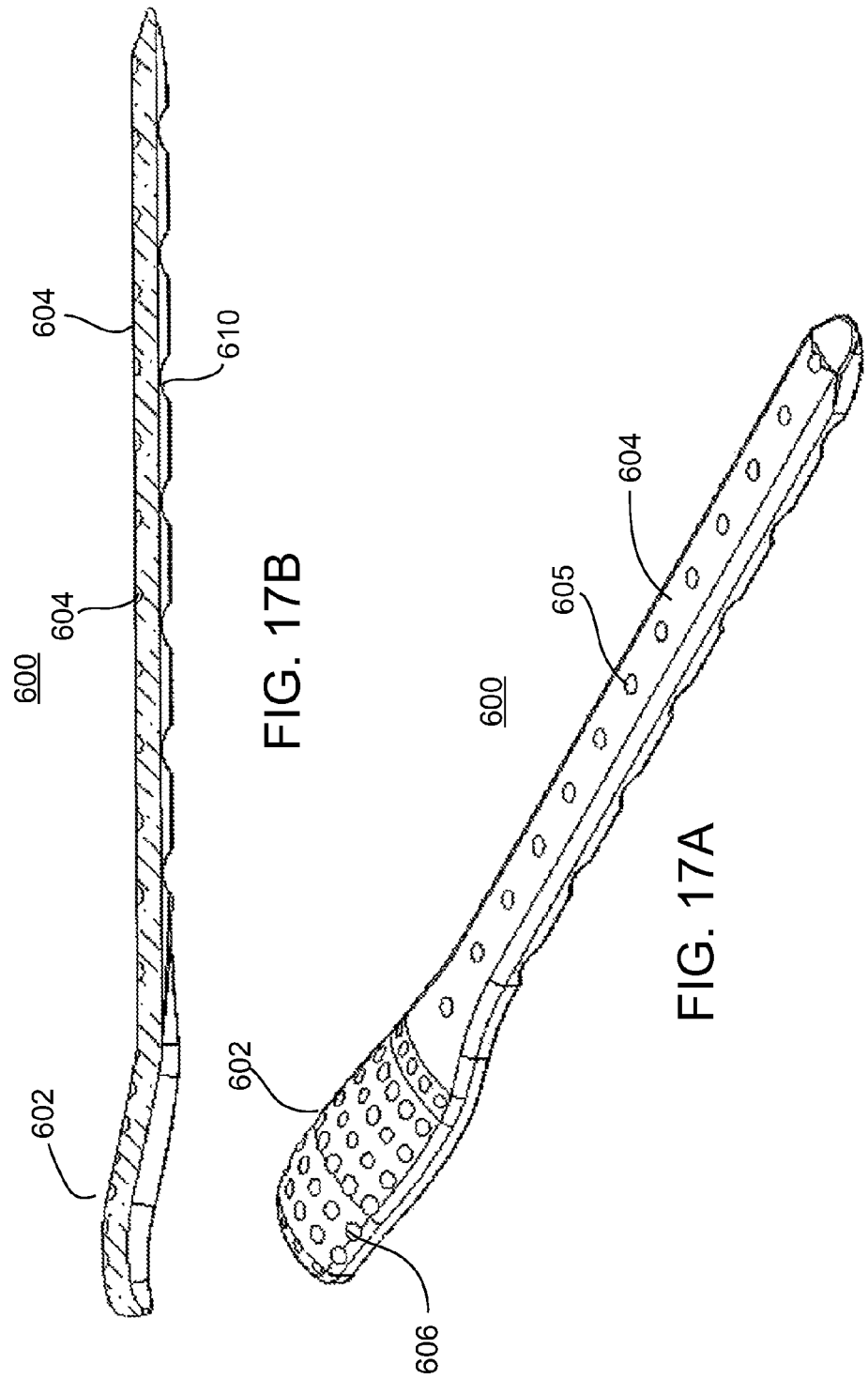
FIGS. 17A and 17B are top perspective and longitudinal cross-sectional views respectively of a bone-supporting implant component including one or more blind bores or grooves.

FIGS. 17A and B respectively illustrate top perspective and side sectional views of a bone plate 600 demonstrating several features, one or more of which may be provided in one or more embodiments of bone-supporting components, i.e., bone nails and bone plates.

Bone plate 600 includes a head portion 602 and a stem or shaft portion 604, both of which are configured and sized according to the particular bone for which plate 600 will be used. In the Figure, a proximal Humerus plate is shown. Head portion 602 includes an array of bores 606 and stem portion 604 includes a line of bores 608 spaced longitudinally along a midline of the stem. These are configured to receive the fixation components. The number and spacing of bores 606 and 608 are optionally determined, for example, like the size and configuration of the plate itself, according to the particular bone for which the plate will be used.

Stem portion 604 optionally includes a line of transversely extending depressions 610. The purpose of depressions 610 is to reduce the area of contact between the bone and the plate. Reduction of the contact area may also assist in maintaining the integrity of the fixation. In some embodiments, this may also be achieved by the spacing and size of the depressions.

According to some embodiments of the invention, bone-supporting components, including bone nails and bone plates, are manufactured and provided to the user without some or all screw holes. Instead, the holes are formed by the surgeon during the implantation. As shown in FIGS. 17A and 17B, implant 600 may include one or more blind bores or grooves or other indentation and/or protrusions in the stem, which do not penetrate the entire implant thickness. For example, they may extend 10 to 20% of the thickness of the plate stem. Alternatively, they may extend more, for example, 50%, 70% or more, for example, being narrow-diameter holes.

The blind grooves cooperate with drilling tool and fixation component insertion accessories as described below, and help to position and grip the drilling device while the surgeon drills holes through the grooves. This allows the surgeon to insert the fixation components devices in the optimal locations and directions/angles. Since these may vary from case to case, the surgeon has the flexibility to address the need of each case individually and to provide for more efficient and safe fixation. In addition, where small implants are involved, the option to have only the number of screw holes for the particular application may contribute to the strength of the implant. Optionally, an attachment location, for example, a notch or hole is provided for attaching an adjustable tool guide to help guide a tool during reconfiguration of the implant (e.g., by drilling or cutting).

In FIGS. 17A and 17B, the blind bores in stem 604 are represented schematically at 606 as circular, but in some embodiments, there may be provided a different shape that can keep the drill bit in place during drilling.

Optionally, the implant is provided with several such grooves, which are located at positions and/or in directions of the implant that do would not compromise the required implant biomechanical properties following drilling.

Optionally, the bone implants are manufactured and provided to the user with at least one screw hole, while the other required screw holes are created during the surgery.

In some embodiments of the invention, bone nails are also manufactured with a longitudinally extending row or other suitable arrangement of blind grooves, either round or elongated as described above in connection with FIGS. 17A and 17B. It is also to be understood that both bone nails and plates may be provided with pre-drilled through-holes (as in the embodiments described in connection with FIGS. 2 and 3) in some embodiments of the invention.

Also in some embodiments, through-holes may be threaded (not shown) for attachment of accessories used during drilling and fixation-component insertion, and/or for locking the fixation component head to the bone-supporting component as now to be described.

Figure 18:
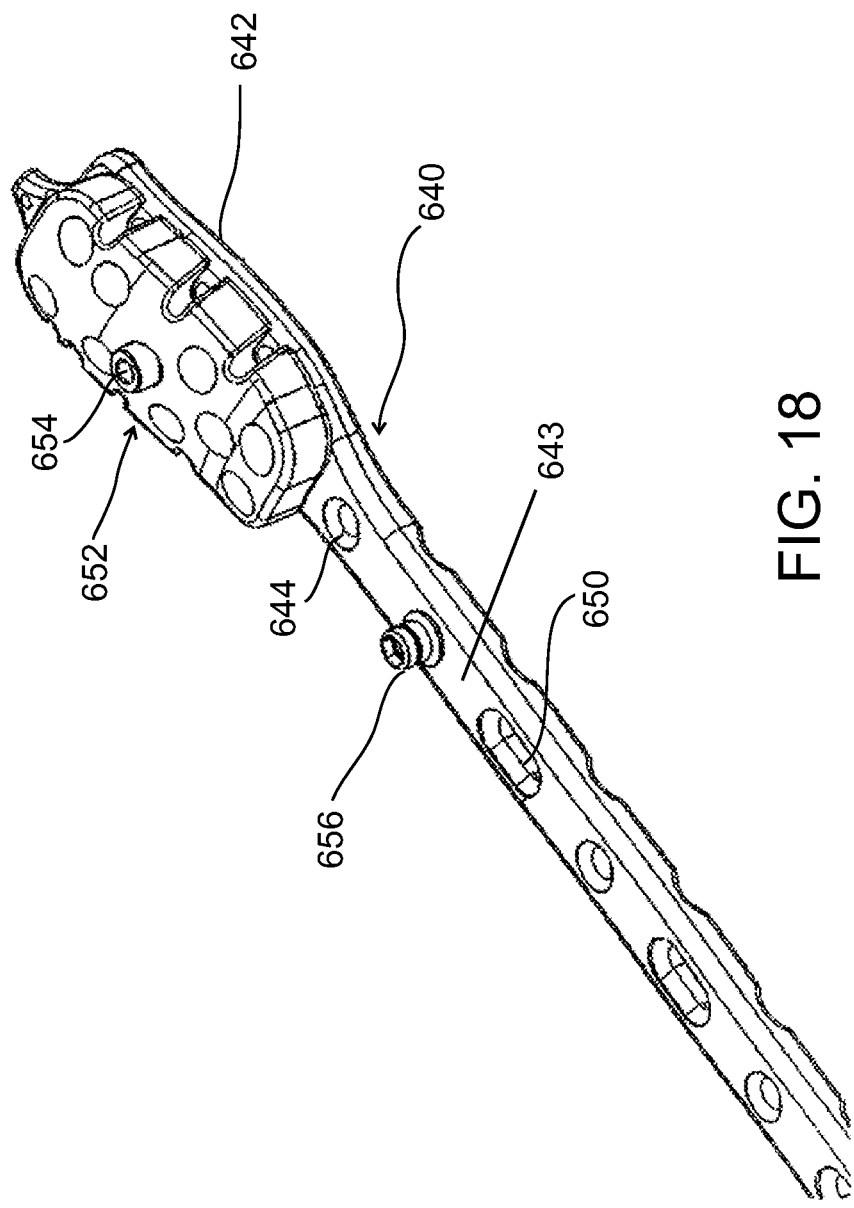
FIG. 18 is a side and top perspective view of a bone plate in which the shaft includes round bores and elongated slots, and a targeting guide which may be used to help drill holes in the bone plate head and/or the underlying bone.

Referring now to FIG. 18, there is shown a bone plate 640, including a head, 642, and a stem or shaft 643. The figure also illustrates a targeting guide 652, and a drill sleeve 656. Stem 643 of bone plate 640 includes round bores 644 and elongated slots 650. These may be blind, or extend though the plate as previously described.

Targeting guide 652 is a drilling accessory which may be used to help drill holes in head 642 and/or the underlying bone for receiving one or more fixation devices. Targeting guide 652 includes an array of holes, some of which may be oriented obliquely to bone head 642. Targeting guide 652 is attached to head 642 by one or more targeting screws 654, which are held in place by threads (not shown), Optionally the targeting guide 652 has one pin (not shown), that enter into a hole in the implant, in addition to the screw 654.

By using targeting guide 652 made of polymer, with implant made of composite material, during the surgery it is possible to see under fluoroscopy very clear view of the fracture, and reduce it more accurately, and place the screw more accurately. Optionally targeting guide 652 made of polymer such as PEEK. Optionally targeting guide 652 is supplied pre-assembled on the implant. Optionally targeting guide 652 is intended for single use.

Figure 19:
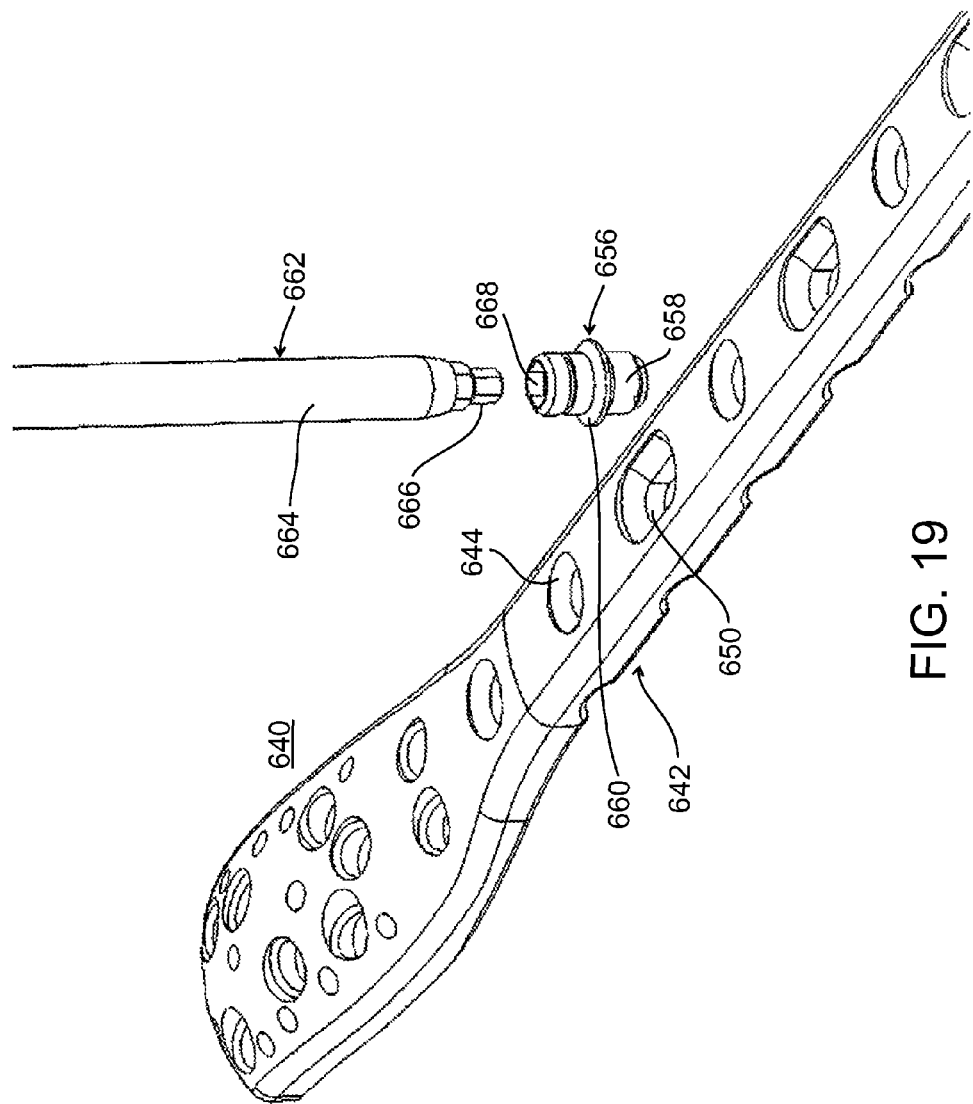
FIG. 19 is a top and side perspective view of a bone plate and a drill sleeve for use in drilling holes for fixation components, and a drill sleeve holder to assist in insertion and removal of the drill sleeve.

FIG. 19 shows further details of drill sleeve 656. This is an accessory for use in drilling holes for fixation components to be inserted in the stem 642 of a bone plate 640. Drill sleeve includes a lower portion 658 configured to be received in one of the bores 644 and 650 in bone plate stem 642. This may optionally be threaded to match complementary threads in one of the circular bores 644, or may be dimensioned for a friction fit.

Drill sleeve 656 also includes a skirt or shoulder portion 660 that limits insertion depth into the bore.

FIG. 19 also shows a drill sleeve holder 662 to assist in insertion and removal of drill sleeve 656. This includes a handle 664, the distal end of which includes a fitting 666 configured to engage a complementary bore 668 in drill sleeve 656.

Figure 20A:
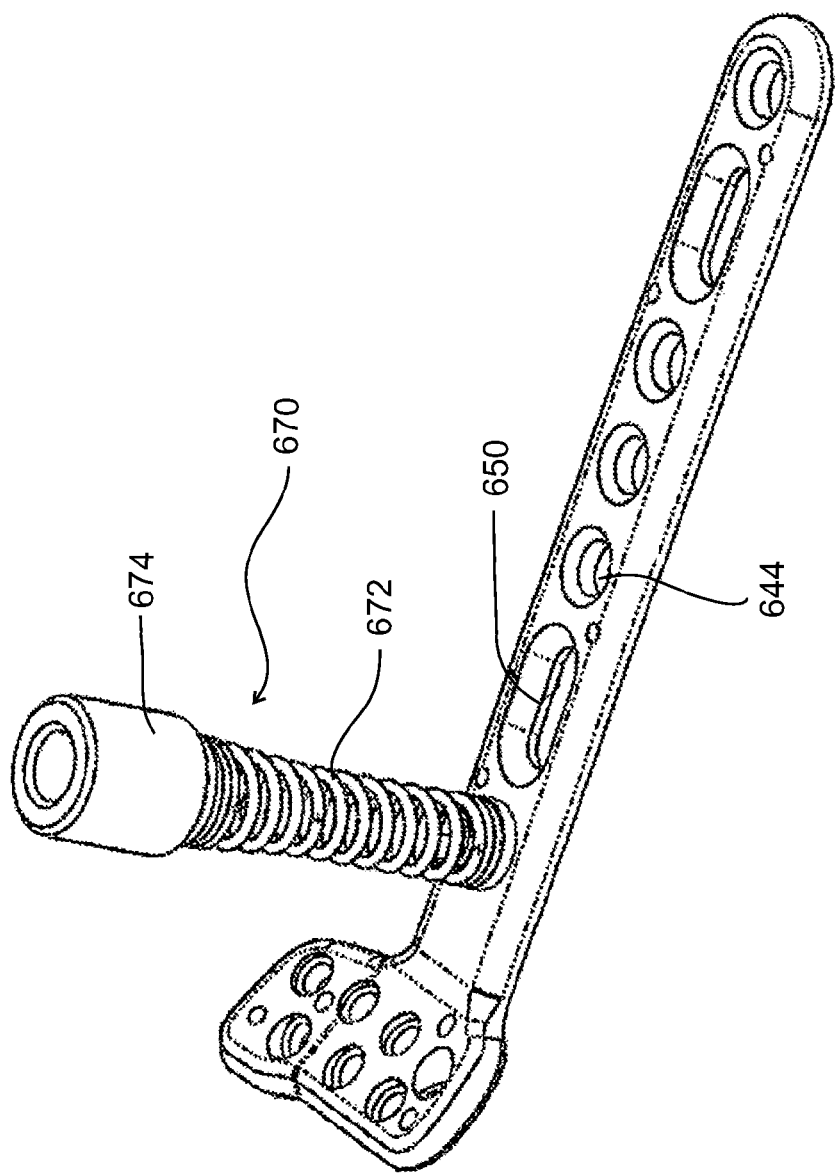
Figure 20B:
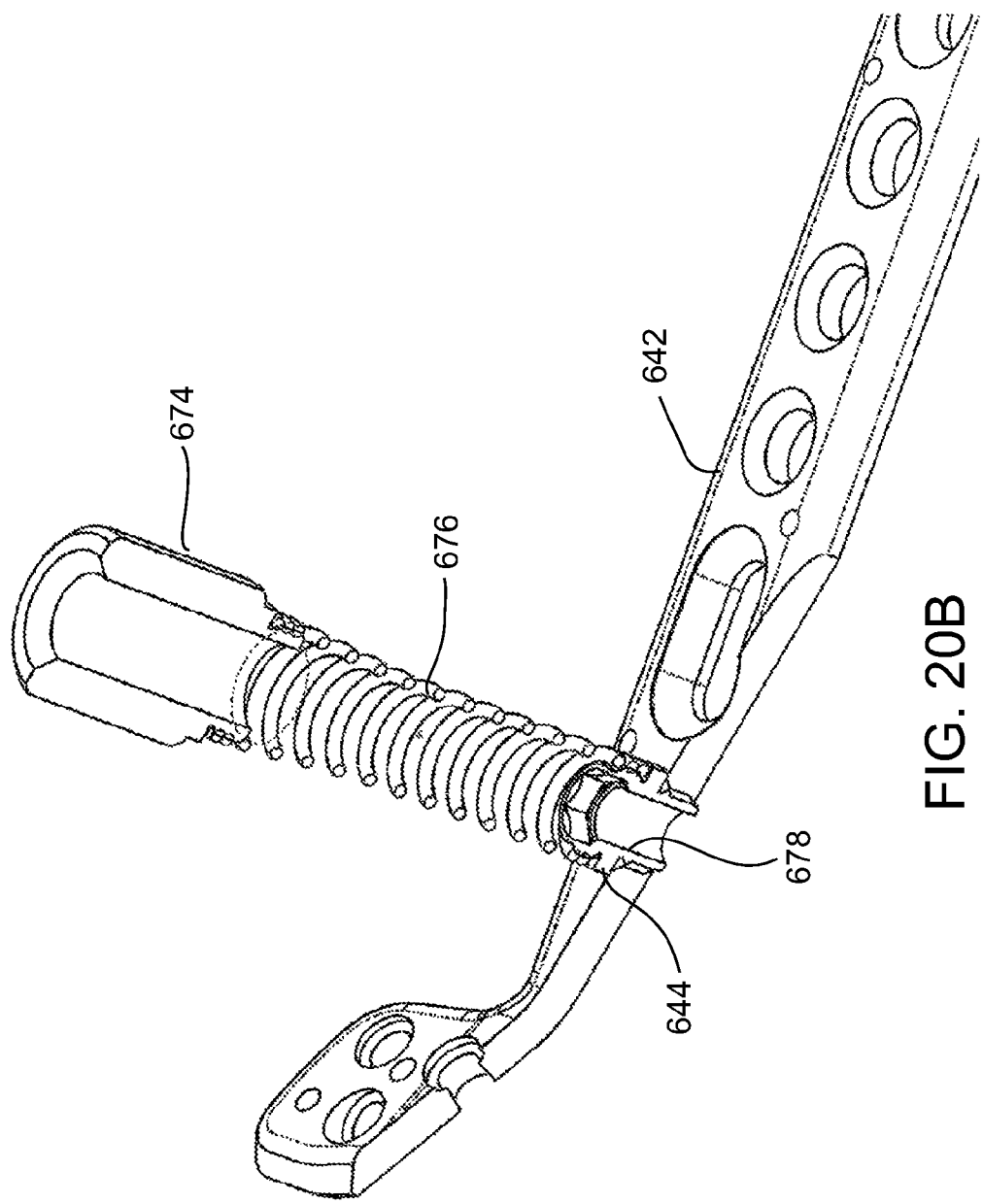

FIGS. 20A and 20B illustrate another drill sleeve 670. According to some embodiments of the invention. These are top perspective and vertical sectional views respectively. Drill sleeve 670 differs from drill sleeve 656 of FIG. 19 in that it includes an elongated portion 672 and a knob 674 at its proximal end to facilitate handling the device. The distal end 678 of elongated portion 672 (see FIG. 20B) is threaded to engage complementary threads (not shown) in one of the bores 644 in bone plate stem 642.

Elongated portion 672 may take various forms in embodiments of the invention. The form illustrated in FIGS. 20A and 20B is a spiral spring 676 which allows torque transfer from the knob 674 to screw and unscrew distal part 678, while preventing transfer of bending forces, thus reducing the chance of damage to the bores or the internal threads.

Optionally, elongated portion 672 may be formed of oppositely wound concentric springs, i.e., one spiraled clockwise, and the other spiraled counterclockwise.

Figure 21:
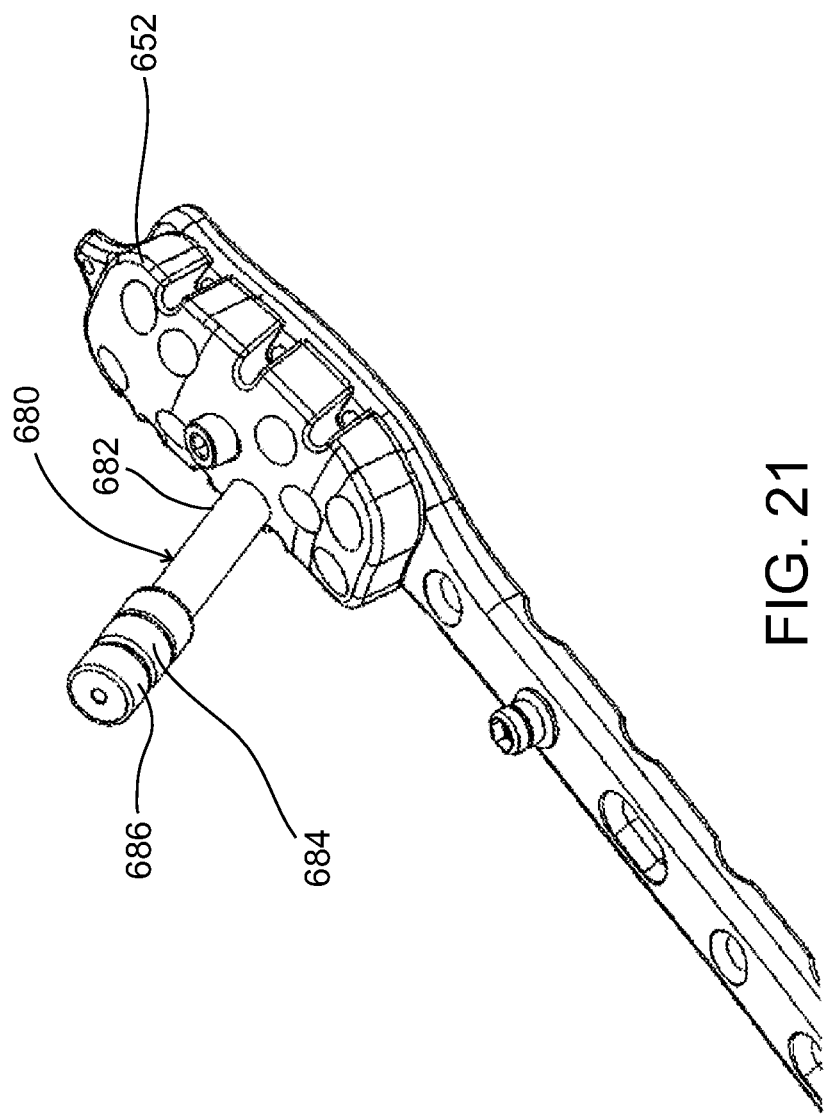
FIG. 21 is a top and side perspective view illustrating a combined drill targeting guide and fixation device insertion accessory according to some embodiments of the invention.

FIG. 21 illustrates a combined targeting guide and fixation device insertion accessory 680. This includes three components: an insertion guide 682 for insertion of a fixation-component, a drill guide sleeve 684, and a K-wire sleeve 686. A K-wire is optionally used before drilling, to get idea about the drilling direction.

In use, accessory 680 is assembled with insertion guide 682 and drill guide 684 connected together and inserted into a hole in a targeting device 652.

All the accessories described in connection with FIGS. 18-21 may be formed of metal or of a polymer, optionally a fiber-reinforced polymer composite.

It should also be understood that other configurations of drill and fixation-device insertion guide accessories, including such accessories that are configured for disposal after a single use, are also within the scope of the invention. It should also be understood that, in some embodiments of the invention, implantation may be done without using the drill sleeve as described above.

FIGS. 22A and 22B are schematic top views that illustrate ways to provide for visualization of bone plates under fluoroscopy during implantation and/or at follow-up in some embodiments of the invention. In FIG. 22A, a bone plate 700 is shown that includes a head 702 and an elongated stem portion 704. A radiopaque marker shown here as a series of short marginal wire sections 706 extends around the edges of head 702 and the distal end 708 of stem portion 704.

FIG. 22B shows a variation in which the wire sections 710 extend along the entire contour of bone plate 700.

The markings may take optionally various forms, for example, two longitudinally continuous wire sections formed of tantalum or other suitable metal in the embodiment of FIG. 22A, or a single continuous marginal wire in the case of the embodiment of FIG. 22B. For example, tantalum wire having diameter of about 0.2 to about 0.5 mm may be used, and located about 1 mm from the implant edge. Use of a radiolucent bone plate allows an advantageous method of assisting the surgeon in positioning of bone fragments for optimum healing, and following the progress of post-operative healing.

FIGS. 23A and 23B are assembled and partially exploded perspective views of some embodiments of the invention illustrating a design for a bone nail insertion support apparatus 750 which may be used to share the loads exerted on the nail-handle connection area during insertion of the nail into the bone.

In FIG. 23A, insertion apparatus 750 is shown enclosing the connection interface between a bone nail 752 and a handle tube 754. Insertion apparatus 750 includes a housing comprised of two complementary parts 756 and 758 that cover the connection interface. These are optionally connected to each other by a screw 760 (refer also to FIG. 23B), that is received in holes 762, 764 in parts 756 and 758, respectively, as well through the lower hole 766 at the proximal end of nail 752. Hole 764 has a thread and screw 760 is inserted through hole 762, and nail hole 766 and threaded into hole 764. The latter will also be used for insertion of a fixation-component. Optionally, the screw 760 is provided already connected to one of the parts 756. A pin 768 in the other part 758 is configured to be inserted into a hole in the handle tube 769. Torque is transmitted through pin 768 to part 758, and then to the screw 760 and nail 752. In this manner, part of the torque is transmitted from the handle to the nail.

Optionally, insertion apparatus 750 may also be configured to enable the use of one insertion apparatus with nails of different diameters.

During operation, the nail 752 is connected to the handle tube 754 via the nail adapter (not shown in the figure), and then apparatus 750 is assembled over the nail-handle connection area. Following introduction of most of the nail into the bone, the insertion apparatus is disconnected and removed to allow introduction of the rest of the nail into the bone.

FIGS. 24A and 24B are, respectively, assembled and partially exploded views of some embodiments of another nail installation device 770. As shown, installation device 770 is similar to insertion device 750, except that the complementary parts 772 and 774 configured to enclose the connection area between the nail 752 and the handle 754 is generally rectangular rather than cylindrical. Because of the similarity to device 750, further description will be omitted in the interest of brevity.

Figure 25B:
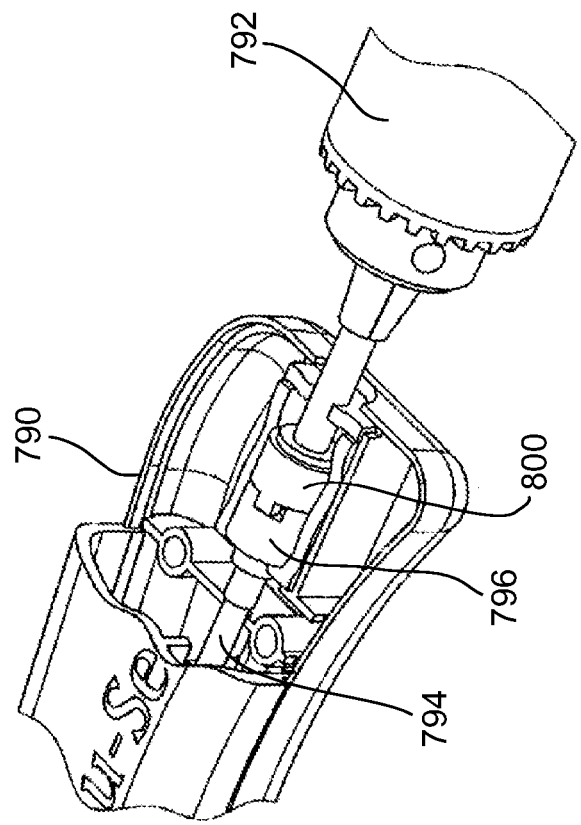
FIGS. 25A and 25B are partial cut-away views illustrating a portion of a radiolucent connector 790, coupled to a drill power unit 792.
Figure 25A:
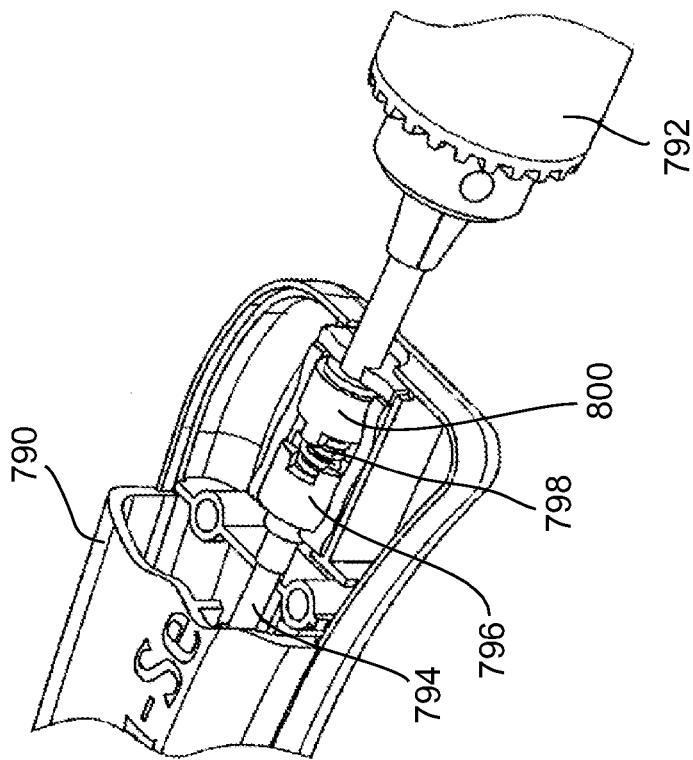

Reference is now made to FIGS. 25A and 25B, which are partial cut-away views illustrating a portion of the radiolucent connector 790, connected to a drill power unit 792 (only partially shown). In use, the opposite end of connector 790 is attached to a drill bit (not shown in the figure), optionally at an angle of 90 degrees. Connector 790 includes a flexible cable 794, configured to transmit the torque and speed from the power unit 792 to the drill bit. The cable 794 is connected to a coupler 796, which is attached to a spring 798. This, in turn, is attached at its other end to additional coupler 800, which is configured for connection to power unit 792.

In FIG. 25A, a non-activated configuration of apparatus 790 is illustrated. In this configuration, the two couplers 796 and 800 at the ends of spring 798 do not engage with each other, and thus even if the power unit 792 is operated, the torque is not transferred and the drill bit shall not rotate.

FIG. 25B illustrates the "activated" configuration of the drilling assembly. Upon holding component 790, the surgeon must push power unit 792 to engage coupler 800, so that the later advances, presses against spring 798, and engages with the second coupler 796. This clutch mechanism helps prevent accidental operation of the drill.

In an exemplary embodiment of the invention, the actual drilling tool is made of material that provides for both suitable biocompatibility and biomechanical properties (e.g., hardness). In an exemplary embodiment of the invention, the drilling tool is a standard drill bit used for intra-operatively drilling of holes in the bone. Optionally, the drill bit is made of stainless steel. Optionally, the drill bit is made of high-speed steel or other materials, such as cobalt steel alloys, which hold their hardness at higher temperatures and thus may be used to drill hard materials.

Other hard materials for constructing the drill tool may be tungsten carbide and other carbides, and polycrystalline diamond (PCD). Optionally, the drilling tool may be coated with material that provides for additional characteristics, such as heat resistance and/or corrosion resistance and/or hardness. Coating materials that may be used are, for example, black oxide, titanium nitride (TiN), titanium aluminum nitride (TiAlN), titanium carbon nitride (TiCN), diamond powder and zirconium nitride. In another exemplary embodiment of the invention, instead of a drill bit a whole saw or other cutting implement may be used. In an exemplary embodiment of the invention, the drill bit is allowed to be made of less hard materials as it is used only a small number of times and/or is used for drilling a composite material.

Figure 26A:
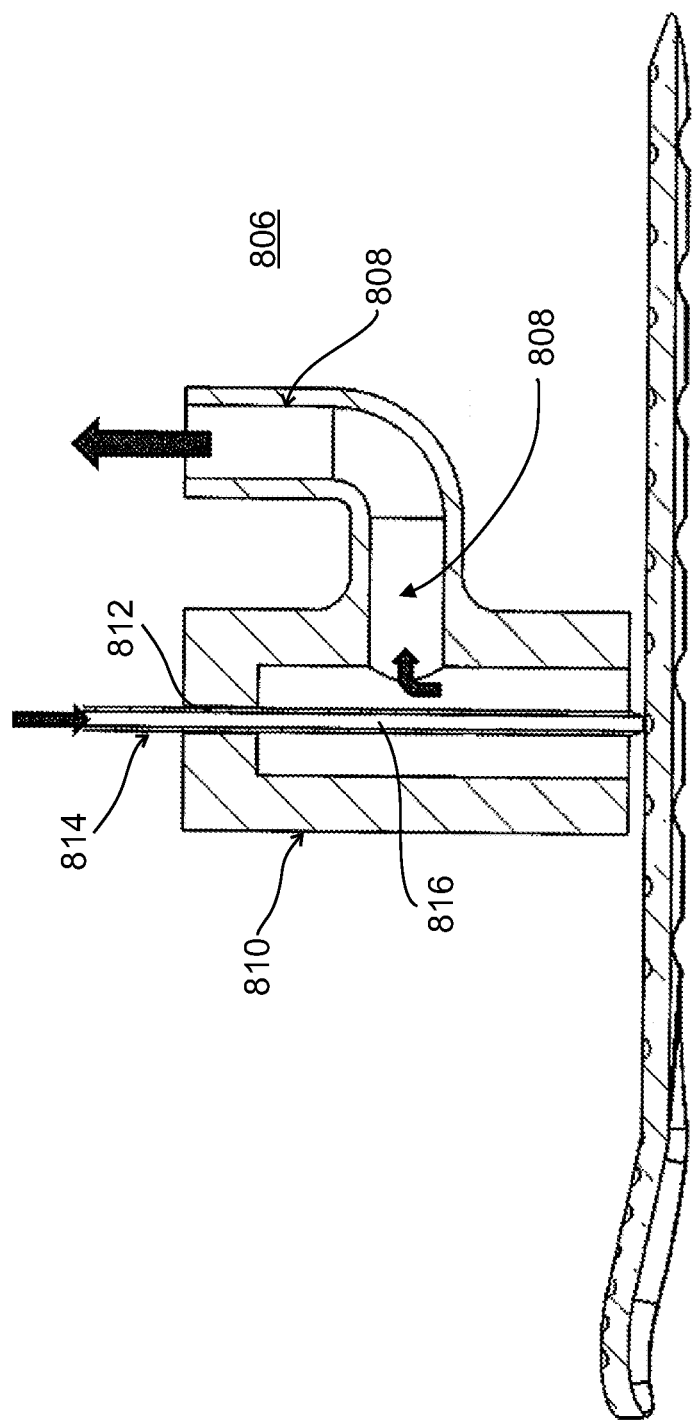
FIGS. 26A and 26B are schematic sectional views that illustrate embodiments of the invention in which provision is made for removal of drilling debris.
Figure 26B:
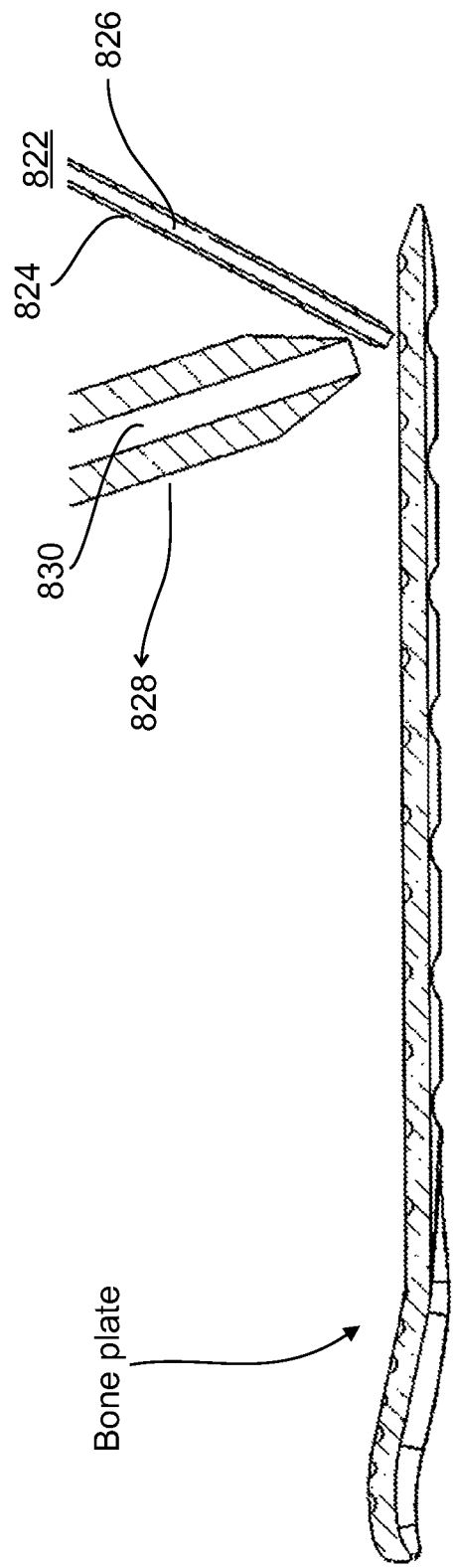
Figure 27:
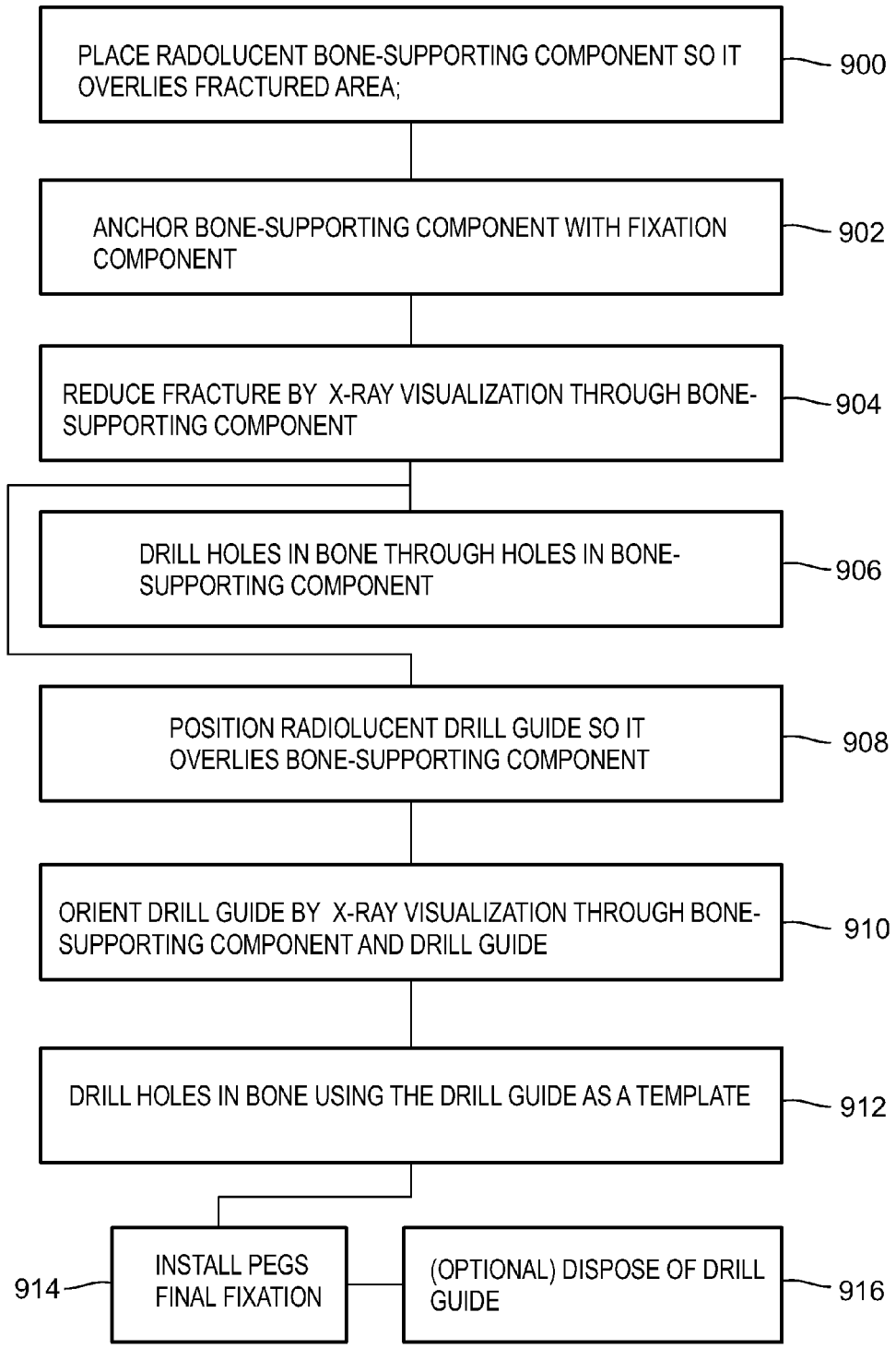
FIG. 27 shows in flow-chart form, an example of how methods according to some embodiments of the invention may be performed.

FIGS. 26A-26B illustrate embodiments of the invention in which provision is made for removal of drilling debris. A device 806 according to such embodiments includes a suction tube 808 the interior 820 of which is configured to be attached to a vacuum source (not shown) and a drill-receiving portion 810 have a hole 812 through which a drill bit 814 projects to the drilling site.

Additionally and/or alternatively, drill 814 may be cannulated at 816. Optionally, a suction tube (not shown) is located within cannulation 816. Alternatively, there is no suction tube, and the suction is performed directly from the cannulation or using a separate suction tube. Optionally, suction of drilling products may be performed simultaneously from the drill bit cannulation (with or without a separate suction tube) and from a suction tube 808 as illustrated. The suction tube may be made of various materials, such as, but not limited to, metals and polymers. In some embodiments, the suction tube is made of a rigid material. In some embodiments, the suction tube is flexible.

In an exemplary embodiment of the invention, the drill is powered by suction and/or air-flow provided in a surgery, e.g., from a wall mounted centralized source, and such suction is also used for suction of debris in addition to or instead of powering the drill.

In some embodiments, the suction process is accompanied by irrigation, for example by sterile saline solution. In such embodiments, during drilling, saline is delivered through drill bit cannulation 816, while suction of the drilling material is achieved using tube 808. Alternatively, irrigation fluid is introduced through tube 808 and the drilling products are sucked from an inner tube inside the drill bit cannulation. Optionally, drill bit is not cannulated, and both tubes (for liquid flushing and for suction) are positioned outside the drill bit, one over the other.

Irrigation as described enables cooling of the implant and surrounding tissue while drilling is being performed, to avoid damage of tissue and/or devices, as well as debris removal.

FIG. 26A illustrates another debris removal and irrigation device 822 according to some embodiments. Here, device 822 includes a drill 824, which may be cannulated at 826 for irrigation and a separate tube 828 for suction which may be placed in proximity to each other during drilling by the surgeon. Alternatively, the functions of tube 826 and cannulation 826 may be reversed, or both cannulation 826 and tube 828 may be used for suction.

Experiments have been conducted to assess the effectiveness of drilling a bone implant together with evacuation of the drilling material. During the test, a composite material bone plate, made of carbon fibers-reinforced PEEK, was drilled using a drill bit, which was contained within a polymeric tube. The later was attached to the plate while its other end was connected to a vacuum pump to allow suction of the drilling products. Upon drilling, the drilling products were sucked into the tube and removed from the plate and its surrounding. Following drilling, the plate and the area outside the tube were inspected. The test results indicated that only an insignificant amount of residues was detected.

In some embodiments of the invention, the drill bit is used to create a perpendicular round hole. Additionally and/or alternatively, the drill bit creates an oblique hole.

Materials and/or coating for the drilling tool may be one or more of those described above.

In another exemplary embodiment of the invention, the drill bit is a hole saw.

The drill bit may be of conventional form, or optionally may also comprise a tap (thread cutting), to create a thread, at least at part of the plate screw hole, so that the screws may be locked to the plate. Alternatively, a separate tap may be used. Additionally and/or alternatively, while screwing the screw into the bone through the plate or nail hole, the screw itself serves as a tap of the plate, and its threaded part is locked to the plate or nail.

Exemplary Component Fabrication Methods:

In an exemplary method of fabrication, the core and the sleeve are constructed from pre-impregnated (prepreg) tapes of carbon fiber-reinforced polymer, preferably thermoplastic polymer such as PEEK. In some embodiments of the invention, the core is formed by compression molding. Before molding, the prepreg tapes are pre cut to the size and shape of the mold cavity, and inserted into the mold in accurate total weight.

Where the bone-supporting components are supplied pre-drilled, the passages are optionally created during the compression molding process (and not by drilling) Alternatively, passages are created during the compression molding process and drilling is used following molding to achieve the final desired shape and dimensions of the passages).

The sleeve is then build over the core by spirally winding tape of the prepreg composite, optionally at a pitch of 45 degrees relative to the longitudinal axis of the core. When more than one tape is used to build up the sleeve, the adjacent tapes are alternatingly spirally wound clockwise and counterclockwise optionally having a pitch of +/−45 deg relative to the longitudinal axis of the core.

The winding tool for the sleeve optionally includes a heater to heat the tape before the winding, preferably also preheating the core, and a pressing wheel to create consolidation of the winding tape into the core. In some embodiments, to strengthen the implant, the process of compression molding is performed under high pressure. For example, the pressure may be higher than 100 Atm., optionally higher than 400 Atm., optionally higher than 700 Atm., optionally higher than 1,000 Atm.

According to some embodiments of the invention, the prepreg tapes are heated during winding. The heating is optionally provided by a laser. Alternatively and/or additionally, an Infra Red source is used for heating the tape during winding. Alternatively and/or additionally, the tape is heated using hot gas such as air.

In some embodiments, a composite material bone implant, for example an intramedullary nail, is produced from a core of longitudinal tapes of fiber-reinforced polymer, formed by compression molding, followed by winding of tapes of fiber-reinforced polymer over the core, together with laser heating. Use of this technique for the manufacturing of a bone implant component may eliminate the need of a final compression molding (i.e., for the core with the helically wound tapes).

According to some embodiments of the invention, the process of manufacturing a composite material bone implant also comprises the step of slightly expanding the winding, for example, using heat and internal pressure. In an exemplary embodiment of the invention, an intramedullary nail is produced in compression molding followed by tape winding, and then a rod is axially pushed into the heated mold, to slightly push outwardly the core and the winding.

According to some embodiments of the invention, production of a composite material bone implant involves separate compression molding for two or more portions of the implant, where portions are later connected, to form the core of the implant. Intramedullary nails often include a cannulation of about 2-3.5 mm diameter along their longitudinal axis, to enable introduction of the nail into the bone over a guide wire. In addition, many of the nails include a few degrees bent or a radius, to comply with the anatomy of the bone.

Production of a bent and cannulated nail in standard compression molding is possible but generally considered technically difficult. In an exemplary embodiment of the invention, in order to achieve proper production of such a nail, two moulds are used, each for a half of the nail that comprises "half cannulation". Following the production of the two halves, they can be molded together with mandrel inside, to get hollow core, or alternatively winding is performed around the attached two halves (e.g., tapes are helically wound at ±45 degrees), and the entire construct is then compressed, with a wire in the mold designed to keep the cannulation along the nail axis.

Optionally, to shorten the time required for the winding process and to reduce costs, winding over the longitudinal core is performed so that one or more tape is placed over another tape, and each tape is tensioned separately during winding.

For screws such as 250 in FIG. 10A that include an outer layer 252 of a hard material, this may be applied as a coating or by winding metal tape over the screw, optionally by using bending wheels. Alternatively the tape may be wound over a screw mandrel, unscrewed from the mandrel, and then screwed over the composite screw.

Exemplary Methods of Use:

FIG. 28 shows in flow-chart form, an example of how methods according to some embodiments of the invention may be performed.

At 900, after appropriate preparation, a radiolucent (X-ray transparent) bone-supporting component, for example, a bone plate as described above, formed of a fiber-reinforced polymer matrix composite is positioned in proximity to the fracture site so it overlies the fractured area. At 902, the bone plate (optionally, the head) is optionally anchored using at least one fixation component, for example, a bone screw or peg. Optionally, the targeting guide described herein is used for this.

At 904, taking advantage of the radiolucency of the bone plate, the surgeon optionally reduces the fracture by positioning the bone fragments optimally for good healing.

At 906, for example, in embodiments in which a drill sleeve is not used, the surgeon optionally drills through the pre-drilled holes or built-in drilling guides in the bone plate to accommodate a desired number of bone pegs or screws.

The method then proceeds to 914 where the pegs or screws are installed, for example, using a screw guide as in FIG. 21, to provide final fixation.

In embodiments in which a drill guide and/or other accessories for example as described in connection with FIGS. 18-21 are optionally used, the method proceeds from 904 to 908, where the radiolucent drill guide and accessories are positioned and optionally attached to the bone plate. At 910, the drill is oriented and positioned by the surgeon as required, for example, by inspecting the fractured area visually or under X-ray through the bone plate and the drill guide. This is again made possible by the radiolucency of the bone plate and the drilling accessories formed, and helps assure that the fixation components are optimally oriented for best support.

At 912, with the drill guide and accessories properly oriented, holes are drilled in the bone. At 914, the fixation components are installed, optionally using the screw guide.

In embodiments in which the bores in the bone plate are blind, both the bone supporting component and the bone may be drilled at 912. Optionally, during the drilling, debris disposal is provided.

Finally, optionally, at 916, the drill guide and other accessories are discarded after a single use.

Exemplary Dental Implants;

Some embodiments of the invention pertain to dental implants formed of a composite material, according to embodiments already described for other bone implants. Optionally, the dental implant is composed of a single component forming a crown or cap, a screw that goes into the bone, and an abutment intermediate the crown and the screw. Optionally, it comprises more than one component. Optionally, the abutment and the bone screw are one composite material component. Optionally, the different components are made of more than one material, including of a non-composite material.

In some embodiments, the implant is configured so that its strength and elasticity are compatible with the loads exerting on the tooth and/or bone. In an embodiment, the composite material dental implant is coated, for example with material that improves the ability of the implant to integrate in the bone and enhances bone ingrowth. Such coating may be, for example, porous titanium or hydroxyapatite (HA). In an embodiment, the coating is added using a vacuum plasma spray (VPS) technique. In an exemplary embodiment of the invention, the thickness of the coating is in the range of 50-70 µm.

In some embodiments, a coating is added following implant surface treating, for instance grid blast or bombardment of argon ionized ions. Optionally, particles of the coating material (e.g., titanium) are inserted into the implant surface prior to performing the coating itself, in order to improve the adhesion of the coating to implant surface. In an embodiment, the composite material bone implant is heated and the particles are forced/introduced so that they penetrate into the implant outer layer. In an embodiment, particles of coating material are not limited to the outer layer of the implant, but rather are incorporated into the entire implant, optionally during the production of the implant construct.

In some embodiments, the area of the dental implant that contacts soft tissue comprises smooth surface, in order to prevent infection at the region of the implant. Optionally, the smooth surface does not comprise the coating. Alternatively, the smooth surface comprises smooth, non-porous, coating.

It is expected that during the life of a patent maturing from this application many relevant ultrasound transducers will be developed and the scope of the term transducer is intended to include all such new technologies a priori.

As used herein the term "about" refers to ±10%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A bone implant kit comprising:
 a bone-supporting component formed mainly of a fiber-reinforced polymer composite, in the form of a radiolucent bone plate with a plurality of locations designated for attaching a fixation component therethrough;
 one or more fixation components for the bone-supporting component; and
 a radiolucent drill guide defining an array of holes, said drill guide configured to be directly mounted on said bone plate such that said array of holes is aligned with and adjacent to said plurality of locations of said bone plate to facilitate drilling for insertion of the fixation components;
 wherein said bone-supporting component and said drill guide, when mounted on said bone-supporting component to form an assembly, are radiolucent enough to allow imaging of the bone through said assembly using x-rays.

2. A bone implant kit according to claim 1, wherein the bone-supporting component includes pre-drilled passages for the fixation components so that only the bone needs to be drilled during the implantation procedure.

3. A bone implant kit combination according to claim 2, wherein the bone-supporting component is supplied with at least one undrilled hole, and both the bone and passages for the fixation components are drilled during the implantation procedure.

4. A bone implant kit according to claim 1, further including an arrangement for removing drilling debris created by drilling for insertion of a bone implant comprising a suction element configured for connection to a source of suction and for disposal of a suction port on the suction element adjacent to a drill bit during drilling.

5. A bone implant kit according to claim 1, further including an arrangement providing irrigation fluid to a drilling site comprising an irrigation element configured for connection to a source of irrigation fluid,
wherein the irrigation element includes a fluid outlet port configured to be positioned adjacent to a drill bit during drilling.

6. A kit according to claim 1, comprising a screw for attaching said drill guide to a hole in said plate.

7. A kit according to claim 1, wherein said drill guide comprises a pin which mounts in a hole in said plate.

8. A kit according to claim 1, wherein said drill guide is provided in kit form pre-attached on said plate.

9. A kit according to claim 1, wherein said bone plate has a head and a stem and wherein said drill guide is configured for guiding drilling into holes in said head.

10. A kit according to claim 1, wherein said drill guide defines at least one hole that is oblique to said plate.

11. A kit according to claim 1, comprising at least one drill sleeve adapted to mount on any of a plurality of holes in said plate or in any of a plurality of holes in said drill guide.

12. A kit according to claim 11, wherein said drill sleeve includes a shoulder which prevents over penetration thereof into said plate.

13. A kit according to claim 11, wherein said drill sleeve is dimensioned to friction fit in a holes of said plate or a hole of said drill guide.

14. A kit according to claim 11, comprising a k-wire sleeve.

15. A kit according to claim 11, comprising an insertion sleeve for guiding the insertion of a fixation device into said hole.

16. A kit according to claim 15, wherein said insertion sleeve and said drill sleeve are adapted to be connected together.

17. A kit according to claim 1, wherein said locations comprise unthreaded holes.

18. A method of treating a bone fracture comprising:
positioning a bone-supporting component in the form of a bone plate at a desired position in relation to a fracture site,
wherein the bone-supporting component is formed of a fiber-reinforced polymer composite manufactured with pre-drilled passages for receiving fixation components;
providing a radiolucent drill guide with an array of holes directly mounted on said bone plate such that said array of holes is aligned with and adjacent to said passageways;
imaging the bone through said bone supporting component and said drill guide using x-rays; and
aiming, using said x-rays so acquired, a k-wire or drilling through said drill guide and said bone.

19. A method according to claim 18, wherein the drilling is performed using a radiolucent drill.

20. A method according to claim 18, comprising manipulating bone fragments after said positioning while viewing said bone fragments through said component.

21. A method according to claim 18, wherein said drilling comprises drilling through a sleeve attached to said plate or said drill guide.

22. A method according to claim 18, comprising guiding a fixation component to said bone a sleeve attached to said plate or said drill guide.

23. A method according to claim 18, comprising assembling a plurality of guide sleeves together and mounting on said drill guide.

24. A kit according to claim 6, wherein said screw is held in place by a thread.

25. A kit according to claim 1, wherein a contour of said drill guide matches a contour of said bone plate to provide for introducing said drill guide and bone plate into the body together.

26. A method according to claim 18, wherein said providing a radiolucent drill guide comprises introducing said drill guide into the body to the fracture site.

* * * * *